US012790362B2

(12) United States Patent
Johnson et al.

(10) Patent No.: US 12,790,362 B2
(45) Date of Patent: Nov. 10, 2026

(54) OSCILLATING FLUIDIZED BED OLIGONUCLEOTIDE SYNTHESIZER

(71) Applicant: Eli Lilly and Company, Indianapolis, IN (US)

(72) Inventors: Martin D. Johnson, Westfield, IN (US); Luke P. Webster, Indianapolis, IN (US); Jessica Ann Zelinski, Indianapolis, IN (US); Wei-Ming Sun, Carmel, IN (US); Timothy Michael Braden, Greenwood, IN (US); Yufei Wei, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 644 days.

(21) Appl. No.: 18/317,282

(22) Filed: May 15, 2023

(65) Prior Publication Data

US 2023/0340007 A1 Oct. 26, 2023

Related U.S. Application Data

(63) Continuation of application No. PCT/US2021/063185, filed on Dec. 14, 2021.

(60) Provisional application No. 63/127,269, filed on Dec. 18, 2020.

(51) Int. Cl.

*C07H 21/00* (2006.01)
*B01J 8/18* (2006.01)
*B01J 8/22* (2006.01)

(52) U.S. Cl.

CPC ............ *C07H 21/00* (2013.01); *B01J 8/1872* (2013.01); *B01J 8/226* (2013.01)

(58) Field of Classification Search

CPC ......... C07H 21/00; B01J 8/1872; B01J 8/226; B01J 8/1809; B01J 4/008; B01J 4/02

See application file for complete search history.

(56) References Cited

U.S. PATENT DOCUMENTS

| | | | |
|---|---|---|---|
| 4,415,732 | A | 11/1983 | Caruthers et al. |
| 6,069,243 | A | 5/2000 | Scozzari |
| 6,087,491 | A | 7/2000 | Tang et al. |
| 2006/0014176 | A1 | 1/2006 | Iyer et al. |
| 2006/0014716 | A1 | 1/2006 | Frey et al. |
| 2020/0391175 | A1 | 12/2020 | Nguyen et al. |
| 2025/0145660 | A1 | 5/2025 | Berglund |

FOREIGN PATENT DOCUMENTS

| | | | |
|---|---|---|---|
| CA | 3218505 | A1 | 11/2022 |
| CN | 1479745 | A | 3/2004 |
| CN | 1747963 | A | 3/2006 |
| JP | H08239397 | A | 9/1996 |
| JP | 2006-512411 | A | 4/2006 |
| KR | 2019-0022726 | A | 6/2019 |
| KR | 2020-0052369 | A | 5/2020 |
| WO | WO 1997/007126 | A1 | 2/1997 |
| WO | 2004/055036 | A1 | 7/2004 |

(Continued)

OTHER PUBLICATIONS

Sinha N.D., from Agrawal. S., ed., Methods in Molecular Biology, vol. 20, Protocols for Oligonucleotides and Analogs, 1993, Humana Press Inc., p. 437-463. (Year: 1993).*

Kaplan, Bruce Emil. "The automated synthesis of oligodeoxyribonucleotides." Trends in Biotechnology 3.10 (1985): 253-256.

Beaucage, Serge L. "Solid-phase synthesis of siRNA oligonucleotides." Current Opinion in Drug Discovery and Development 11, No. 2 (2008): 203.

Tavoulareas, E. Stratos. "Fluidized-bed combustion technology." Annual review of energy and the environment 16, No. 1 (1991): 25-57.

International Search Report and Written Opinion in International Application No. PCT/US2021/063185, dated Jul. 2, 2021, 6 pages.

(Continued)

*Primary Examiner* — Jonathan S Lau

(74) *Attorney, Agent, or Firm* — Wolf, Greenfield & Sacks, P.C.

(57) ABSTRACT

A method and device for building an oligonucleotide on a solid phase resin within a filter reactor, wherein the method and device as used as a solid phase synthesis system. As part of the solid phase synthesis process, a protecting group will be removed from the 5' position of an oligonucleotide that is attached to the solid phase resin and then an activated amidite (phosphoamidite) solution is added. The activated amidite solution flows up and down, or fluidizes and mixes with the resin beads within the bed reactor and reacts at the 5' position of the oligonucleotide, wherein the phosphorous linkage found within the amidite comprises a P atom that is in an oxidation state of III. Once the activated amidite solution has been reacted, the P atom is converted from an oxidation state of III to an oxidation state of V. Any of the reactions including deblocking, coupling, oxidation, sulfurization, or capping can be fluidized or mixed to get complete contacting between the reagents and the resin. Reagents drain from the reactor out the filter bottom before washing. The resin bed is flat and channel free because of the fluidization or mixing prior to the washes and can be re-fluidized during any of the washes. A spray cone or other distributor evenly spreads reagents or wash solvents onto the top of the resin bed without disrupting the flat even spread of resin in the radial direction. Washing after any given reaction can be divided into several individual segments. The cleaner portion of washes after a particular reaction in one cycle, can be collected in a holding vessel and used as the first washes after reaction in the next cycle. In-process integrated multi-pass washing can be used to enable more efficient use of the wash solvent. Excess reagent solution used for deblocking reaction is recycled and reused from one phosphoramidite cycle to the next, making the use of deblocking more efficient.

32 Claims, 26 Drawing Sheets

(56) References Cited

FOREIGN PATENT DOCUMENTS

| | | | |
|---|---|---|---|
| WO | WO 2013/179412 | A1 | 12/2013 |
| WO | WO 2020/256828 | A1 | 12/2020 |
| WO | WO 2021/158444 | A2 | 8/2021 |
| WO | WO 2022/132681 | A1 | 6/2022 |
| WO | WO 2023/021427 | A1 | 2/2023 |
| WO | WO 2025/128958 | A1 | 6/2025 |
| WO | WO 2026/090370 | A1 | 4/2026 |
| WO | WO 2026/090376 | A1 | 4/2026 |
| WO | WO 2026/090391 | A1 | 4/2026 |
| WO | WO 2026/090395 | A1 | 4/2026 |

OTHER PUBLICATIONS

International Preliminary Report on Patentability, mailed Jun. 29, 2023, for Application No. PCT/US2021/063185.

International Search Report and Written Opinion, mailed Apr. 28, 2025, for Application No. PCT/US2024/059975.

Invitation to Pay Additional Fees, mailed Mar. 5, 2025, for Application No. PCT/US2024/059975.

International Search Report and Written Opinion, mailed Mar. 3, 2026, for Application No. PCT/US2025/052196.

International Search Report and Written Opinion, mailed Feb. 24, 2026, for Application No. PCT/US2025/052225.

International Search Report and Written Opinion, mailed Mar. 4, 2026, for Application No. PCT/US2025/052232.

Invitation to Pay Additional Fees, mailed Feb. 25, 2026, for Application No. PCT/US2025/052206.

International Search Report and Written Opinion, mailed Jun. 2, 2023, for Application No. PCT/US2023/012870.

International Preliminary Report on Patentability, mailed Aug. 29, 2024, for Application No. PCT/US2023/012870.

International Search Report and Written Opinion, mailed Apr. 15, 2026, for Application No. PCT/US2025/052206.

[No Author Listed] Models 392 and 394 DNA/RNA Synthesizers, Applied Biosystems (May 1, 1991) [online], [retrieved from internet on Mar. 18, 2026]. <URL: https://documents.thermofisher.com/TFS-Assets/LSG/manuals/cms_095578.pdf>, Figure p. 4-5.

* cited by examiner

| Feed | x (feed num) | y (pump num) | z (channel num) | Tubing size OD |
|---|---|---|---|---|
| AM1 | 7101 | P1 | 1 | 1/16" |
| AM2 | 7102 | P1 | 2 | 1/16" |
| AM3 | 7103 | P1 | 3 | 1/16" |
| AM4 | 7104 | P2 | 1 | 1/16" |
| AM5 | 7105 | P2 | 2 | 1/16" |
| AM6 | 7106 | P2 | 3 | 1/16" |
| AM7 | 7107 | P3 | 1 | 1/16" |
| AM8 | 7108 | P3 | 2 | 1/16" |
| ACT | 7110 | P3 | 3 | 1/16" |
| Cap A | 7201 | P4 | 1 | 1/16" |
| Cap B | 7202 | P4 | 2 | 1/16" |
| OX | 7203 | P4 | 3 | 1/16" |
| SULF | 7204 | P5 | 1 | 1/16" |
| DCA | 7205 | P5 | 2 | 1/16" |
| ACN | | P6 | 1 | 1/16" |
| WASTE | | P7 | 1 | 1/16" |

| x (feed num) | il (cross num) | Tubing size OD |
|---|---|---|
| 7101 | 1 | 1/16" |
| 7102 | 1 | 1/16" |
| 7103 | 1 | 1/16" |
| 7104 | 2 | 1/16" |
| 7105 | 2 | 1/16" |
| 7106 | 2 | 1/16" |
| 7107 | 3 | 1/16" |
| 7108 | 3 | 1/16" |
| 7110 | 3 | 1/16" |

FIG. 7 CONT.

5' MeMOP*fG*fU*fAfUmAfAmCmCfUmUmCmCfAmUmUmUmUmGmA*mG*mG3'

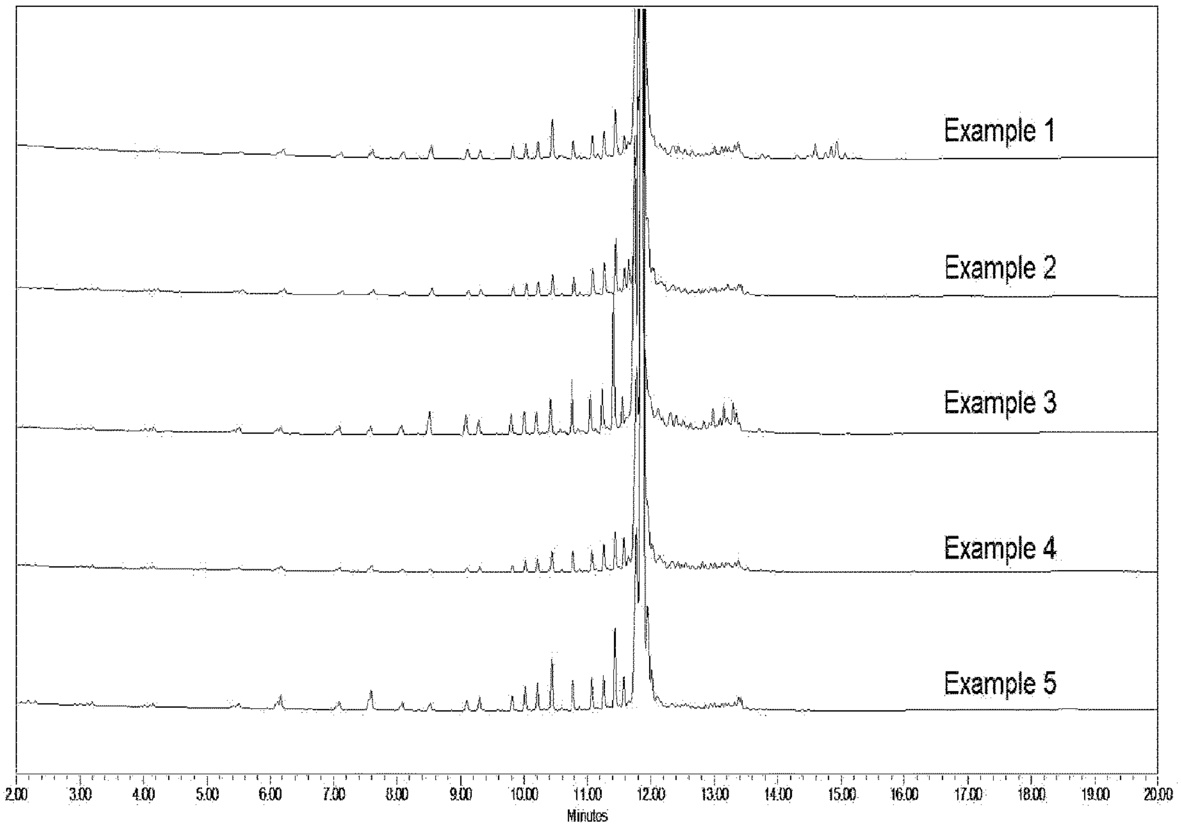
Figure 14. UPLC chromatogram overlays for examples 1-5, as listed in Table 13.

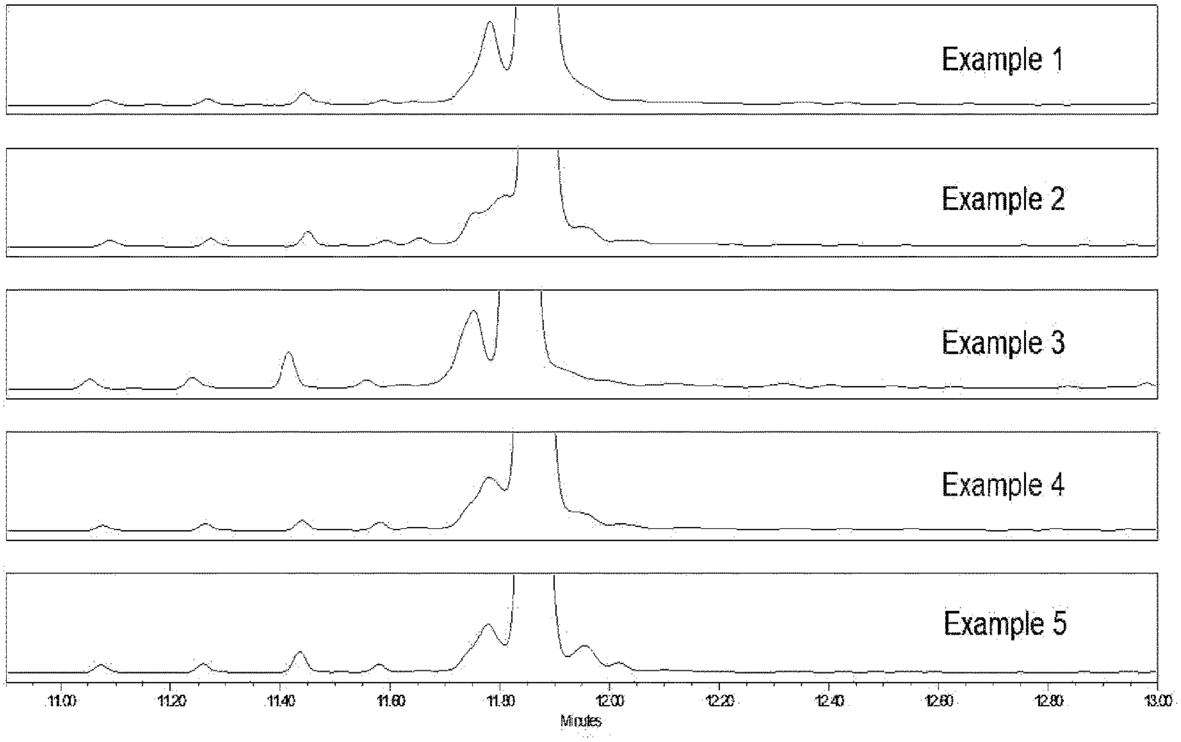
Figure 15. UPLC chromatogram overlays for examples 1-5, as listed in Table 13, zoomed in around the main peak.

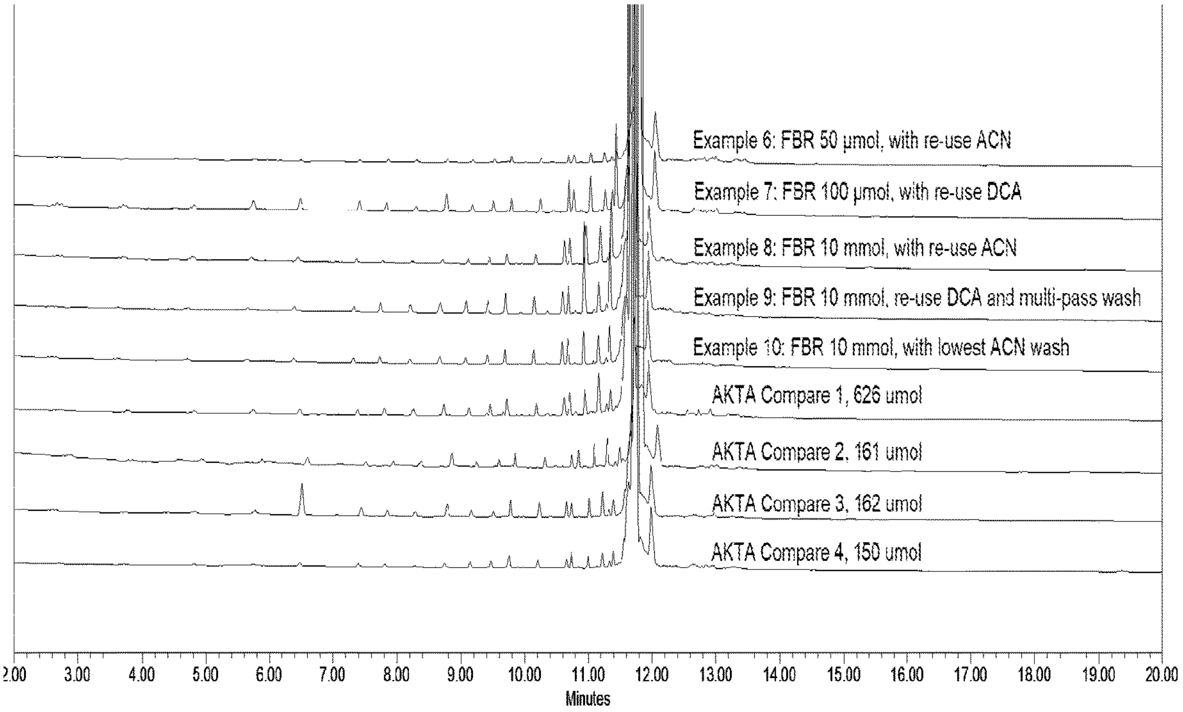
Figure 16. UPLC chromatogram overlays for examples 6-10, and “AKTA compare” 1-4, as listed in Table 17.

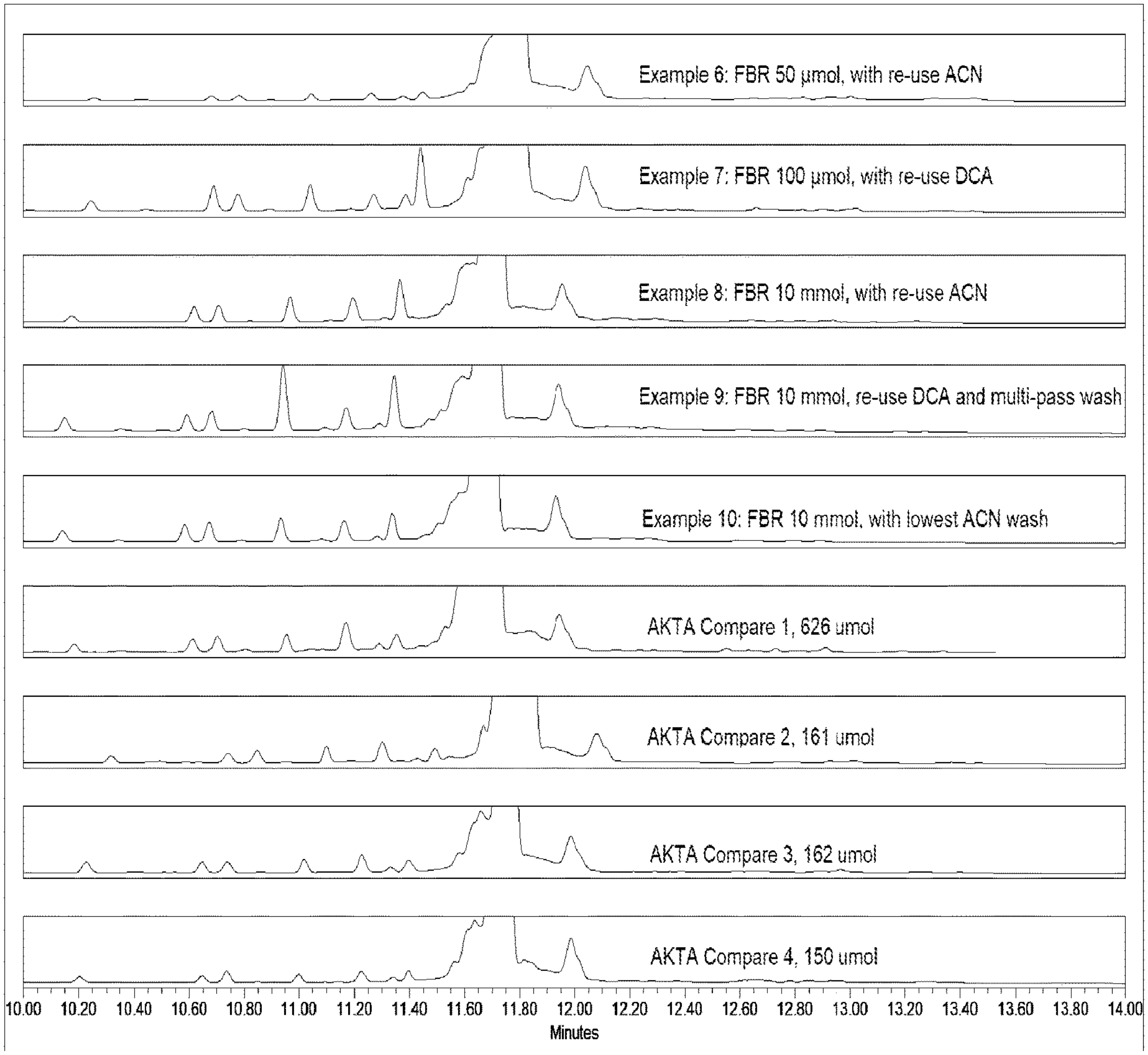
Figure 17. UPLC chromatogram overlays for examples 6-10, and “AKTA compare” 1-4, as listed in Table 17, zoomed in around the main peak.

OSCILLATING FLUIDIZED BED OLIGONUCLEOTIDE SYNTHESIZER

TECHNICAL FIELD

The present disclosure relates to a new system and method for manufacturing oligonucleotide synthetically. More specifically, the present disclosure relates to a device and method that uses oscillating flow or gas bubbling to create a fluidized bed as part of Solid Phase Oligonucleotide Synthesis (SPOS), and completely drains the liquid from the solid resin after each reaction and wash step.

BACKGROUND

Solid Phase Oligonucleotide Synthesis ("SPOS") is the method and system that is most commonly used to synthesize oligonucleotides. SPOS is implemented on a solid phase media which is generally a solid support which are generally made of controlled pore glass (CPG) or macroporous polystyrene (MPPS) spheres. SPOS is a solid-phase synthesis of oligonucleotides using building blocks which are various nucleoside derivatives, the most common of which are phosphoramidites. Specifically, a starting phosphoramidite building block is attached to a solid phase and then each nucleoside (phosphoramidite) is added and coupled to the phosphoramidite building block in a sequential manner until the desired molecule is obtained. In other words, one phosphoramidite is added and coupled (usually at the 5'-terminal OH position), then the next phosphoramidite is added, etc., thereby growing the chain until the desired sequence is obtained. Protecting groups are employed on each of the amine bases on the oligonucleotides as well as the phosphorous so the functional groups are able to withstand the acidic and neutral conditions utilized in the SPOS cycle. Once the oligonucleotide sequence is obtained, the molecule is then cleaved from the solid support and globally deprotected to yield the desired oligonucleotide.

In the SPOS process, there are generally four chemical reactions that occur in order to add a single phosphoramidite to the chain. The first step is the "de-blocking" step, which is generally a detritylation reaction. Specifically, the nucleotide has its 5'-hydroxyl group protected by an acid-labile protection group such as the DMT (4,4'-dimethoxytrityl). This protection group is removed during a continuous flow of the acid solution or via an addition of an acid in a solvent. The acid may be for example, trichloroacetic acid (TCA) dichloroacetic acid (DCA) or some other acid that is carried in an inert solvent such as toluene or dichloromethane or other solvents. In some embodiments, 2% TCA, 3% DCA, or 10% DCA is used with toluene. For DMT protection group, during this "de-blocking" reaction, an orange-colored DMT cation formed is washed out via addition of a washing solution. Accordingly, this step results in the solid support-bound oligonucleotide precursor bearing a free 5'-terminal hydroxyl group.

Once the de-blocking step occurs, the "coupling" step is then performed. This coupling involves adding a solution of activated phosphoramidite in a solvent (such as, for example, a solution of 0.02-0.2 M solution of phosphoramidite in acetonitrile (ACN) (or anhydrous ACN)). This activated phosphoramidite will react with and couple to the free 5'-terminal hydroxyl group that was previously deprotected. Generally, as is known in the art, the solution of phosphoramidite may be "activated" by the addition of a catalyst that facilitates the coupling reaction. Various catalysts are known to "activate" the phosphoramidite including various azole or imidazole compounds. More than one equivalent of the catalyst is often used, as the acidic nature of the catalyst helps to neutralize the diisopropylamine by-product formed in the coupling. Upon the completion of the coupling, any unbound reagents and by-products are removed by washing.

After the coupling step, the next step in the SPOS is either oxidation, thiolation (also named sulfurization) or "capping". Capping is performed because a small percentage of the solid support-bound 5'-OH groups (0.1 to 1% or greater) remains unreacted and needs to be blocked from further chain elongation to prevent the formation of oligonucleotides with an internal base deletion commonly referred to as (n-1), (n-2), (n-3), etc. shortmers. The unreacted 5'-hydroxy groups are, to a large extent, acetylated by the capping mixture. By capping these unreacted OH groups, these impurities can be more readily chromatographically separated out from the desired product. Likewise, if the coupling reaction created other, non-desired products (such as a reaction of an O in the guanosine base or other chemical entities), these non-desired products are also blocked (capped) from reacting further so that they may be more readily separated out in the subsequent purification steps. In some embodiments, the capping step involves treating the solid support-bound material with a mixture of acetic anhydride and 1-methylimidazole. Other capping reagents may also be used.

In the oxidation step, the coupled phosphoramidite that reacted to the 5'-terminal OH group results in a phosphite triester linkage (e.g., in which the P atom is in an oxidation state of +3). This phosphite triester linkage is not natural and is of limited stability under the conditions of oligonucleotide synthesis. Thus, the P atom will be oxidized to a more stable +5 oxidation state via the addition of oxidizers such as iodine and water in the presence of a weak base (pyridine, lutidine, or collidine). This reaction oxidizes the phosphite triester into a tetracoordinated phosphate triester, a protected precursor of the naturally occurring phosphate diester internucleosidic linkage. Oxidation may be carried out under anhydrous conditions using tert-Butyl hydroperoxide or (1S)-(+)-(10-camphorsulfonyl)-oxaziridine (CSO). In other embodiments, sulfurization to a phosphothiolate linker is done instead of oxidation. Those skilled in the art will appreciate that some embodiments of SPOS may be best designed in which the capping step occurs after this oxidation or sulfurization step, or vice versa. Also, those skilled in the art will appreciate that some embodiments of SPOS may be best designed in which the capping step is omitted from some of the cycles, when high conversion is anticipated.

Once these four steps are completed (de-blocking, coupling, either oxidation or sulfurization, and capping), the phosphoramidite building block has been added to the growing chain. As will be appreciated, the phosphoramidite building block that was coupled has its own DMT protecting group that is protecting the 5'-terminal OH group. Thus, the process may then be repeated and another phosphoramidite moiety added until the chain reaches its desired length.

Once the chain has reached its desired length the oligonucleotide protecting groups can be removed and the oligonucleotide can be cleaved from the resin and released into solution. In some cases these protecting groups from the nucleoside amines and the 2-cyanoethyl phosphate protecting groups are globally deprotected in the same base catalyzed hydrolytic cleavage reaction. Aqueous ammonia solutions, mixtures of ammonia and methylamine and others are commonly used for this cleavage/deprotection step. These conditions also efficiently hydrolyze the 3'-linker and cleave the oligonucleotide from the resin.

However, the acrylonitrile by-product which is generated during the ammonolysis of the 2-cyanoethyl protecting groups is able to alkylate the amino base moieties, forming potentially problematic adducts. For this reason, it is sometimes desirable to selectively deprotect the phosphates by treatment with anhydrous solution of a secondary amine (diethylamine for example) while the oligonucleotide is still bound to the resin. Once the acrylonitrile by-product is washed away with solvent, the oligonucleotide can be cleaved and deprotected in aqueous ammonia with no fear of acrylonitrile adduct formation.

While this SPOS process is used commercially and is still the standard in oligonucleotide synthesis, it clearly has drawbacks, the foremost being that it is expensive, generates large amounts of waste, and has limited scalability. As multiple steps are required, the process is very expensive and results in large amounts of solvents being used and waste materials generated. Making matters worse is that many of these solvents are not environmentally friendly. Also, for many of the SPOS solid supports, the amount of material that may be loaded onto the support is low, thereby requiring excessive multiple batches to make commercial quantities. Also, batch size is limited in the conventional packed bed plug flow SPOS reactors because the height of the resin bed is restricted due to pressure drop of liquid flowing down through the bed, and the diameter is restricted because of challenges with radial distribution of reagents and maintaining even bed height over the entire cross section. Further, each oligonucleotide requires a protecting group, which adds to the overall cost of manufacturing.

Perhaps the most glaring weakness of SPOS is its inefficiency. Because four reactions are required to add a single phosphoramidite, if even one reaction type has low conversion each cycle, then the overall yield of the process is drastically affected. Moreover, the solutions used in the four reactions are added to the resin usually by adding them to the top of the vessel and allowing them to react as they are pumped downwards and out the bottom. Such a process generally results in uneven contacting of liquid and solid phases, especially when channels form in the resin bed, resulting in poor reaction efficiency. Thus, a larger excess of reagents is needed to achieve complete reactions, thorough washing, and high yield. Including reagents and washes, the amount of materials needed to make commercial quantities of oligonucleotides is very high. This uneven contacting also causes ununiform purity across the reactor vessel, especially from top to bottom. Given the limitations of packed bed reactor scale, some of our portfolio assets project to require hundreds of synthesis batches per year. In addition, SPOS using conventional downflow packed bed reactors are not readily amenable to flexible batch size with the same reactor, because changing the resin bed height may result in different yields and impurity profiles due to uneven top to bottom contacting. Furthermore, maximum resin bed height is also limited because of pressure drop through the bed, especially when polystyrene resin particles are swelling and compressing simultaneously while transitioning solvents during flow. Polystyrene resin loading is limited to about 300 μmol/g, because of the need to limit resin swelling and thus limit pressure drop through the resin bed.

Accordingly, it would be an improvement to find a new way to use SPOS, that would address one or more of these deficiencies. It would be a special improvement to find a SPOS system that could be used at a commercial scale for oligonucleotides for large volume products, for example multiple metric tons per year. It would be a further advancement if such a system could be more environmentally friendly and reduce manufacturing costs and overall be more efficient. The present embodiments solve one or more of these deficiencies.

SUMMARY

The present embodiments involve a method of adding a phosphoramidite to a solid phase resin within a bed reactor in which a protecting group is removed from the 5' position of an oligonucleotide and the coupling an activated amidite solution to the unprotected group, wherein the activated amidite solution comprises an amidite and fluidizes the resin in the reactor. Fluidization may occur by forcing the liquid to flow up and down within the bed reactor, bubbling an inert gas, or other type of agitation to create a slurry. The amidite reacts at the 5' position of the oligonucleotide.

In addition to the coupling reaction, reagent solutions for deblocking, oxidizing, thiolating, and capping may each be fluidized with the resin to provide complete liquid/solid contacting and re-set the resin bed with no channels. The fluidization may be followed by plug flow reaction with reagent flow in the downward direction through the resin bed as is typical of conventional SPOS. The same fluidization portion followed by plug flow portion may be done for the solvent washes after each reaction. In this manner, the majority of the resin swelling and shrinking may take place during the fluidization portion of the solid/liquid contacting, where it is advantageous to overcome pressure drop and eliminate channeling.

BRIEF DESCRIPTION OF THE DRAWINGS

The features and advantages of the present disclosure will become more apparent to those skilled in the art upon consideration of the following detailed description taken in conjunction with the accompanying figures.

FIGS. 14-17 are various UPLC chromatograms of the examples.

DETAILED DESCRIPTION

Figure 1:
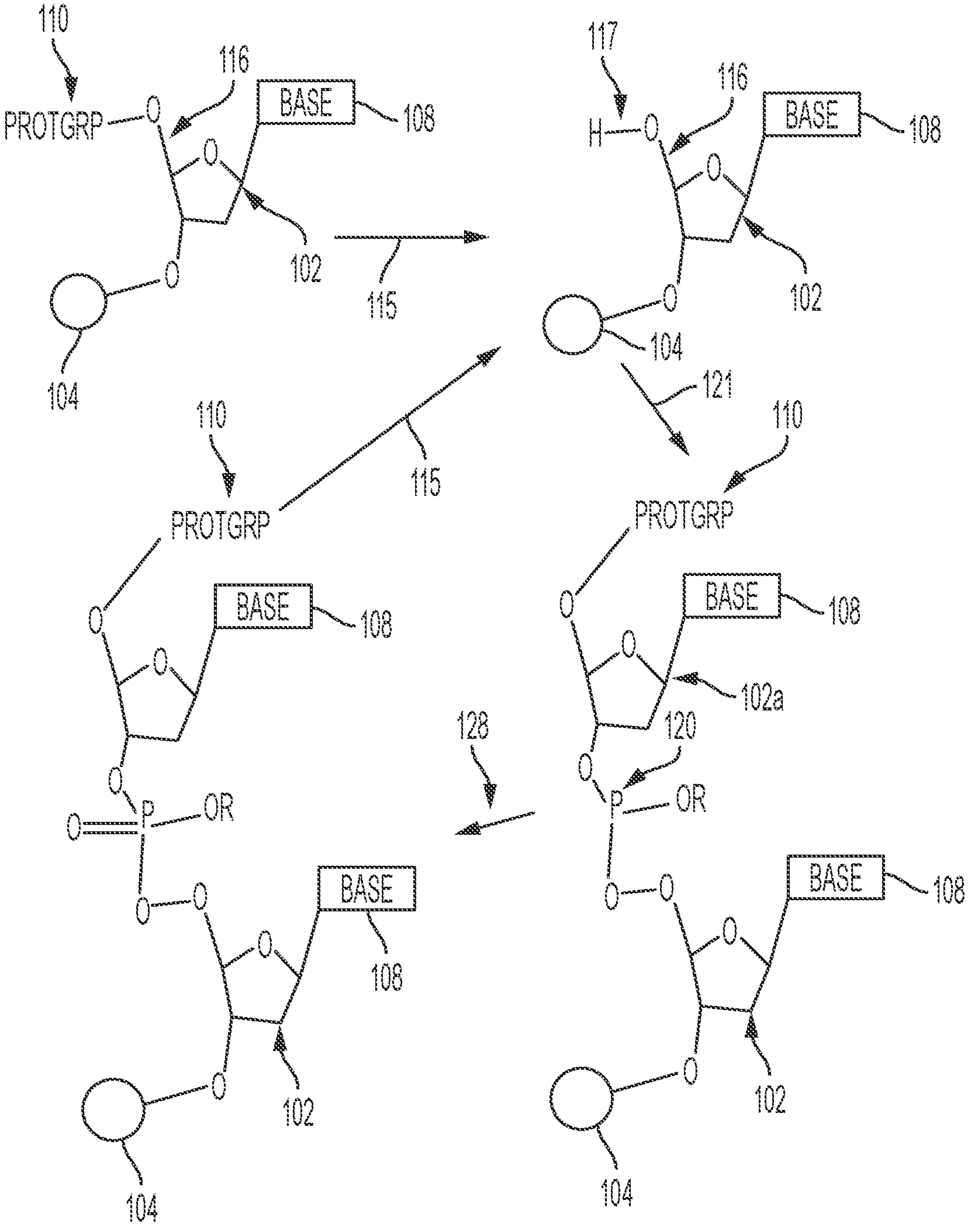
FIG. 1 is a schematic view of the reactions that are conducted in an oligonucleotide SPOS system.

A method of adding an oligonucleotide to a solid phase resin within a bed reactor is disclosed. The method includes removing a protecting group from the 5' position of an oligonucleotide that is attached to the solid phase resin, adding an activated amidite solution to the bed reactor, wherein the activated amidite solution comprises an amidite and flows up and down within the bed reactor or fluidizes with nitrogen bubbling or other agitation and reacts at the 5' position of the oligonucleotide, wherein the phosphorous linkage found within the amidite comprises a P atom that is in an oxidation state of III, and converting the P atom from an oxidation state of III to an oxidation state of V.

In some embodiments, the method further includes the step of adding a capping solution before or after converting the P atom from an oxidation state of III to an oxidation state of V, wherein if the coupling moiety did not react with the amidite solution, the capping solution caps the coupling moiety such that no additional amidite can be coupled to the coupling moiety, wherein the capping solution flows up and down within the bed reactor or fluidizes or mixes with nitrogen bubbling or other agitation. In some embodiments, capping is only done for select phosphoramidite cycles.

In additional embodiments, the method further includes the step of removing the activated amidite solution from the from the bed reactor by passing the amidite solution through a filter located at the bottom of the bed reactor.

Further embodiments may be made which include the additional step of adding a first washing solution to the bed reactor, wherein the adding of the first washing solution occurs after removing the protecting group. In additional embodiments, the method further includes the step of adding a second washing solution to the bed reactor, wherein the adding of the second washing solution occurs after the activated amidite solution has been added to the bed reactor. The first and second may flow up and down or mix with gas bubbling or other agitation within the bed reactor and wherein the method further comprises the step of individually removing the first and second washing solutions from the bed reactor by passing the first and second washing solutions through a filter located at the bottom of the bed reactor. A larger number of wash segments may be used, and it may be done in an integrated multi-pass manner as described herein.

In further embodiments, the step of adding of the second washing solution occurs before the step of converting the P atom from an oxidation state of III to an oxidation state of V. In other embodiments, the step of adding a third washing solution to the bed reactor, wherein the adding of the third washing solution occurs after converting the P atom from an oxidation state of III to an oxidation state of V. In other embodiments, the third washing solution flows up and down or fluidizes or mixes with nitrogen bubbling or other agitation within the bed reactor and wherein the method further comprises the step of removing the third washing solution from the bed reactor by passing the third washing solution through a filter located at the bottom of the bed reactor. A larger number of wash segments may be used, and it may be done in an integrated multi-pass manner as described herein. In other embodiments, the protecting group is a DMT group and wherein the removing the protecting group comprises reacting the 5' position of a nucleotide with an activating solution comprising an acid in solvent. Additional embodiments may be made further including the step of removing the activating solution bed reactor by passing the activating solution through a filter located at the bottom of the bed reactor. In some embodiments, the upward and downward flow within the bed reactor is accomplished by adding pressure to the top of the reactor. In further embodiments, the solid and liquid fluidized bed mixing within the bed reactor is accomplished by adding nitrogen or another gas to the bottom of the reactor or some other type of agitation. In some embodiments, no fluidization or mixing is done during the deblocking step, only plug flow through the resin bed.

Additional embodiments are made in which a cleaner fractions of the wash solvents are recycled and reused from one phosphoramidite cycle to the next. Further embodiments are designed in which the cleaner portion of the reagent solution used for deblocking reaction is recycled and reused from one phosphoramidite cycle to the next. Additional embodiments are made which include in-process integrated multi-pass washing as described herein.

A system for adding an oligonucleotide to a solid phase resin is also disclosed. The system includes a bed reactor and an activated amidite solution, wherein the activated amidite solution comprises an amidite and flows up and down within the bed reactor or fluidizes with nitrogen bubbling or other agitation. The system may have the bed reactor include an inlet that allows pressurized gas to enter the bed reactor, wherein the pressurized gas or some other type of agitation causes the amidite solution to mix with the solids within the bed reactor. In other embodiments, the inlet is positioned at the bottom of the bed reactor. The bed reactor may be pressurized from the top of the bed reactor, wherein the pressure causes the amidite to flow up and down within the bed reactor. In some embodiments, the liquid does not flow up and down in the reactor, but inert gas bubbling from the bottom mixing the liquid and solids in the reactor.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

Referring now to FIG. 1, a schematic is shown to represent the reactions that occur within an SPOS system. Specifically, there is an oligonucleotide 102 that is attached to a resin 104. As shown in FIG. 1, the oligonucleotide 102 may be covalently attached to the resin 104 via an oxygen (ether) linkage. Of course, other types and ways by which the oligonucleotide may be attached to the resin 104 also may be used. (The area of the resin herein is sometimes referred to as a resin bed). The oligonucleotide 102 includes a base 108, such as a base that is commonly associated with DNA or RNA. The base 108 may be protected (e.g., have one or more functional groups of the base protected, as is known in the art).

The oligonucleotide may include a protecting group 110 that protects an O atom group at the 5' position 116. As shown in reaction 115 (represented by an arrow), the O atom at the 5' position 116 may be de-protected such that an OH group 117 is positioned at the 5' position 116. In some embodiments, the protecting group 110 is a DMT group and wherein the removing the protecting group comprises reacting the 5' position of an oligonucleotide with an activating solution comprising an acid in solvent.

Once the 5' position 116 has been de-protected, the oligonucleotide 102 may be reacted with an amidite **102*a*. This amidite 102*a* will react with the de-protected OH group 117 via a P linkage. More specifically, the P atom 120 will react with the OH group 117 to create a bond between the oligonucleotide and phosphroamidite 120, 120*a*. This reaction is known as the coupling reaction 121 (represented by an arrow). The P atom 120 is in an oxidation state of three (3) (also represented as "III"). As a result of the coupling reaction 121, the oligonucleotide and phosphroamidite 120, 120***a* are connected together and one of the oligonucleotides remains coupled to the resin 104.

An oxidation step 128 (represented by an arrow) may then occur which will convert the P atom 120 from an oxidation state of III to an oxidation state of "V" (five or 5). Those skilled in the art will appreciate the conditions that are used to accomplish this oxidation. Although not shown in FIG. 1, a capping step may also be performed either before or after the oxidation reaction 128.

After the oxidation reaction 128, the amidite 120*a* that was added also has a protecting group 110. Thus, a new "cycle" or "series" of reactions may occur. This may involve simply repeating the above-recited reactions to add the next amidite to the chain. Specifically, the protecting group 110 of the amidite 120*a* may be removed (de-protected), and then the coupling reaction 121 and the oxidation reaction 128 (and/or the capping reaction) as needed. This iterative process may be repeated as many times as necessary in order to make an oligonucleotide chain of the desired length. Alternatively, 128 may be a sulfurization (also named thiolation) reaction which will convert the P atom 120 from an oxidation state of III to an oxidation state of "V" (five or 5) where the P atom connects to a sulfur (S) atom through a P=S double bond.

Figure 2:
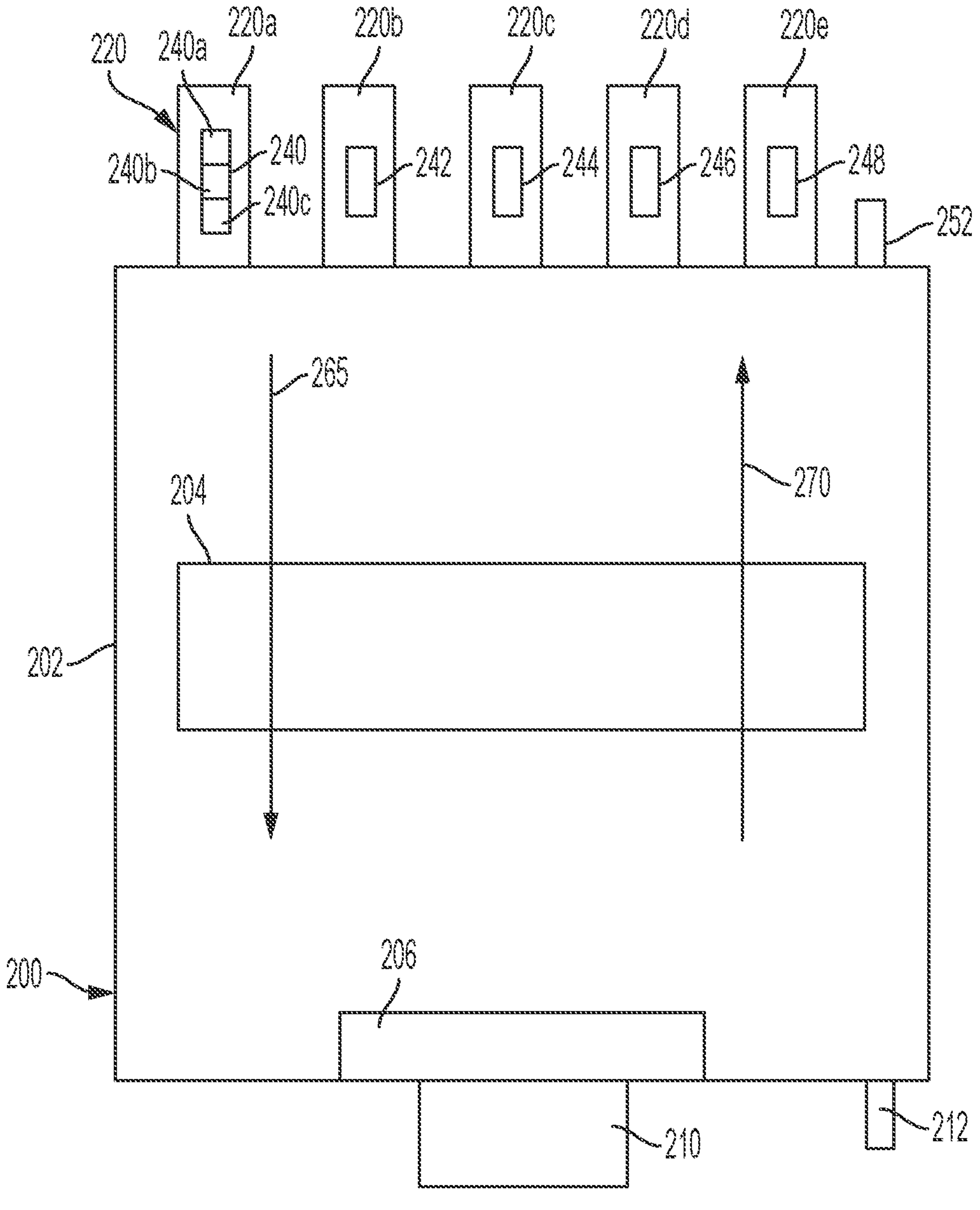
FIG. 2 is a schematic view of an SPOS system.

Referring now to FIG. 2, a schematic of a SPOS reactor system 200 is illustrated. The system 200 includes a reactor 202 (also known as a reactor bed) that houses a resin 204. The resin 204 is the same as the resin 104 described above. Thus, as described above, the resin 204 includes an oligonucleotide chain that may grow to the desired length (as is known in SPOS synthesis). The reactor 202 includes a filter 206 that may be positioned at the bottom of the reactor 202. In the embodiment of FIG. 2, a gas chamber 210 is positioned below the filter 206 as well as an exit port 212. The exit port 212 allows liquid and/or gas to exit out of the reactor 202. In other embodiments, the exit port 212 and gas chamber 210 may be the same opening. In the embodiment of FIG. 2, the exit port 212 is shown in the reactor. In additionally preferred embodiments, the exit port may come of the filter 206. The gas chamber may simply be the process tubing or process piping exiting the bottom of the reactor below the filter.

The reactor 202 also includes one more inlet ports 220. In the specific embodiment of FIG. 2, there are multiple inlet ports 220*a*, 220*b*, 220*c*, 220*d*, 220*e*. The top portion of the reactor with ports 220*a*, 220*b*, 220*c*, 220*d*, 220*e*, and the bottom portion of the reactor with 206, 210, and 212, may be separate vessels with tubing and optional valving between the first feed zone vessel and the second filter reactor zone vessel. Of course, those skilled in the art will appreciate that a greater or fewer number of ports 220 may be used. In fact, in some embodiments, a single port may be used. The port 220*a* may be used to introduce a washing solution 240 (represented graphically by a box) to the reactor 202. The port 220*b* may be used to introduce activated amidite solution 242 (represented graphically by a box) to the reactor 202. The port 220*c* may be used to introduce a capping solution 244 (represented graphically by a box) to the reactor 202. The port 220*d* may be used to introduce an oxidizing solution 246 (for oxidation or thiolation represented graphically by a box) to the reactor 202. The port 220*e* may be used to introduce a de-protecting solution 248 (represented graphically by a box) to the reactor 202. Other embodiments may be designed in which there is only one port 220, and all of the solutions enter into the reactor 202 via a single inlet port 220.

Referring now to FIGS. 1 and 2 collectively, the use of the SPOS system 200 will now be described to show how the reactor 200 (also known as a bed reactor) is assembled and operated. As noted above, the solid support 204 is the solid support for attaching phosporoamidites 102 to the growing oligonucleotide). Using the port 220*e*, a de-protecting solution 248 is used to remove the protecting group 110 from the 5' position 116 of the oligonucleotide 102 that is attached to the solid support 204. The de-protecting solution 248 will flow down through the solid support 204 and then through the filter 206.

Initially the pressure differential above and below the filter 206 is low, for example near 0 psig (pounds per square inch in gauge). Pressure is then applied to the top of the reactor 200 (via pressurization port 252). Usually, this pressure is about 15 psig, but other amounts of pressure may be used. Such pressurization pushes a portion of the liquid de-protecting solution 248 down through the solid support 204 and through the filter 206 (as shown by arrow 265). After the solution 248 is pushed down through the filter 206, the gas chamber or process piping 210 under the filter 206 approaches 15 psig. Then, the system 200 vents the top of the filter 206 (such as through the pressure port 252 (or some other similar mechanism/port), and the near 15 psig trapped below the filter 206 pushes the solution 248 back up through the filter 206 and the solid support 204 (as shown by arrow 270), until pressures above and below approximately equalize near 0 psig again.

By using such pressurization, the solution 248 can be made to flow up and down through the reactor 200, as many times (and the speeds used for the flow) as desired. (Such pressure differential may be used to make all of the solutions added to the reactor 202 flow in the same way). In some embodiments, the solution 248 may flow up and down once every 10-15 seconds. In other embodiments, the system 200 is designed such that the solution 248 will flow down and up one or more times to fluidize the reactor 202, and then slowly flow in the downward direction to continue the reaction conventional plug flow style. By having the solution 248 flow up and down, the solution 248 will contact the solid support 204 multiple times, thus facilitating reaction with complete contacting and thorough distribution of solid and liquid phases. It also reduces pressure drop when liquid downflow ensues because much of the swelling and shrinking happens during fluidization. In other embodiments, only a small portion of the liquid pushes down through the filter screen at the bottom of the reactor, but nitrogen blows up through the filter screen from the bottom, fluidizing and mixing the solid support bed with the liquid in the reactor by bubbling. After the fluidization, by liquid reagent or inert gas upflow from the bottom of the reactor, the next portion of the de-protection reaction may utilize controlled rate downflow of the reagent solution through the solid support bed, as in conventional packed bed SPOS. However, the embodiment may not cause the solution 248 to mix in the reactor at all, only flow through the solid support plug flow and out the filter of the reactor 206.

The de-protection solution 248 may be removed from the reactor 202 via the port 212. The use of pressure via the pressure port 252 may facilitate removal of the de-protecting solution 248, and the liquid may be pumped out the bottom of reactor 202 through 212 at a controlled rate. A first washing solution 240*a* may be added via port 220*a*. This washing solution 240*a* may flow up and down through the reactor 202, using the pressure differentials that are outlined above, or it may mix with the solid support by bubbling gas up through the bottom of the reactor or by some other method of mixing, or it may not flow up and down or mix at all, only pass through the solid support plug flow. By having the washing solution flow up and down or fluidizing by gas bubbling or other agitation, the same solution contacts (and "washes") the solid support 204 once or multiple times. The reagent solution is completely emptied from the reactor prior to the washing solvent addition, and the washing solvent is completely emptied from the reactor prior to the next liquid addition. This can result in a lesser amount of washing solution 240*a* being required (thereby reducing the costs associated with obtaining, using, and disposing of the washing solution), compared to conventional packed bed SPOS processes which may have back-mixing in the liquid layer on top of the solid support bed during transitions. A distributor may be used to evenly charge wash solvent 240*a* onto the entire solid support surface in a manner that does not disturb the flatness of the solid support bed. The number of iterations for flowing the washing solution up and down through the reactor 202 will depend upon the particular reaction and particular cycle. Furthermore, the fluidized washes may be followed by plug flow washes, after the fluidized washes serve to de-swell and re-set the solid support bed with a level top and no channeling. Alternatively, all washes may be done plug flow with no fluidizing, if a particular step does not have pressure drop or channeling challenges. Once completed, the washing solution 240*a* may exit the reactor 202 via the exit 212. Those skilled in the art will appreciate that one or more additional "cycles" or "rounds" of washing may be performed by introducing more portions of the first washing solution 240*a*, as desired. Furthermore, the washing solution may be integrated multi-pass reuse of washing solutions from previous cycles as described herein.

Once the first washing step (or steps) has occurred and the first washing solution 240*a* removed (using pressure, pumping, or other driving force to flow liquid out the filter) from the reactor 202, an activated amidite solution 242 may be added via the inlet 220*b*. The activated amidite solution 242 comprises an amidite 120*a* and will flow up and down through the reactor 202 for as many times as desired, or mix with the solid support by bubbling gas up through the bottom of the reactor or by some other method of mixing. By flowing up and down or mixing, the activated amidite solution 242 contacts the oligonucleotide 102 on the solid support 204 multiple times, thereby increasing the likelihood of coupling reaction and/or the efficiency of the coupling reaction. As described in detail above, the coupling reaction involves the amidite reacting at the 5' position of the oligonucleotide to form a phosphorus linkage of the P atom 120. In other embodiments, the fluidization is accomplished by nitrogen gas bubbling up through the bottom of the reactor to achieve mixing of the solid and liquid phases. The same statement about nitrogen bubbling from the bottom of the reactor for mixing liquid and solid phases applies to each of the following fluidization descriptions in this narrative.

After completing the coupling reaction, the activated amidite solution 242 may be removed from the reactor 202 via the exit 212 (with or without pressure) and a second washing solution 240*b* may be added (via port 220*a* or otherwise). The second washing solution 240*b* may be same solution as the first washing solution 240*a*, or in other embodiments, it may be a different washing mixture. This second washing solution 240*b* may flow up and down through the reactor 202 in the manner described herein. Alternatively, the second washing solution 240*b* may mix with the solid support by bubbling gas up through the bottom of the reactor or by some other method of mixing, or it may flow through the solid support bed plug flow style with no mixing or fluidizing at all. As with the first washing solution 240*a*, embodiments may be designed in which the second washing solution 240*b* may exit the reactor 202 via the exit 212 and one or more additional "cycles" or "rounds" or "portions" of washing may be performed by introducing a new (clean) batch of the second washing solution 240*b*, as desired. Other embodiments may be designed in which a single batch of the second washing solution 240*b* is used.

After removing the final washing solution 240*b* (with or without pressure), the oxidation reaction may occur by introducing an oxidation or thiolation solution 246 via inlet 220*d*. As described above, the oxidation reaction converts the P atom 120 from an oxidation state of III to an oxidation state of V. Again, the oxidation solution 246 may be made to flow up and down through the reactor 202 in the manner outlined herein, thereby increasing reaction efficiency and may result in a lesser amount of oxidation solution 246 being needed, or it may mix with the solid support by bubbling gas up through the bottom of the reactor or by some other method of mixing, or it may flow through the solid support bed plug flow style with no mixing or fluidizing at all. The number of iterations of up and down flow and the time for each cycle will, like the other solutions, vary depending upon the conditions and can be modified by those skilled in the art. After the fluidization, by liquid reagent or inert gas upflow from the bottom of the reactor, a next portion of the oxidation reaction may utilize controlled rate downflow of the oxidizing reagent solution through the solid support bed, as in conventional packed bed SPOS. Once the oxidation reaction is finished, the oxidation solution 246 may exit the reactor 202 via the port 212 (with or without the assistance of pressure).

After the oxidation reaction, a third washing solution 240*c* may be introduced via inlet 220*a* (via port 220*a* or otherwise). The third washing solution 240*c* may be same solution as the first washing solution 240*a* or the second washing solution 240*b*, or in other embodiments, it may be a different washing mixture. This third washing solution 240*c* may flow up and down through the reactor 202 in the manner described herein, or it may mix with the solid support by bubbling gas up through the bottom of the reactor or by some other method of mixing, or it may flow through the solid support bed plug flow style with no mixing or fluidizing at all. Again, such flow up and down and complete emptying of each liquid portion, followed by plug flow washing, allow for may allow for more efficient washing by eliminating channeling, or it may relieve pressure drop issues by allowing the solid support to swell or de-swell while fluidized or suspended, and can reduce the overall amount of washing solution that is needed. As with the first washing solution 240*a* and the second washing solution 240*b*, embodiments may be designed in which the third washing solution 240*c* may exit the reactor 202 via the exit 212 and one or more additional "cycles" or "rounds" or "portions" of washing may be performed by introducing additional portions of the third washing solution 240*c*, as desired. Furthermore, the washing solution may be integrated multi-pass reuse of washing solutions from previous cycles as described herein. Other embodiments may be designed in which a single batch of the third washing solution 240*c* is used. As with all the wash charges or reagent charges to the reactor, a distributor may be used to evenly charge wash solvent onto the entire solid support surface in a manner that does not disturb the flatness of the solid support bed.

A capping reaction may also occur within the reactor 202. This capping reaction may occur either before or after the oxidation reaction (i.e., the step in which the P atom is converted from a III oxidation state to a V oxidation state). In order to facilitate this capping reaction, a capping solution 244 may be added via inlet 220*c*. This capping solution 244 may be made to flow up and down through the reactor 202 in the manner outlined herein, thereby increasing reaction efficiency and may result in a lesser amount of solution 244 being needed. The number of iterations of up and down flow and the time for each cycle will, like the other solutions, vary depending upon the conditions and can be modified by those skilled in the art. Alternatively, the capping reagent solution may mix with the solid support by bubbling gas up through the bottom of the reactor or by some other method of mixing, or it may flow through the solid support bed plug flow style with no mixing or fluidizing at all. After the fluidization, by liquid reagent or inert gas upflow from the bottom of the reactor, the next portion of the capping reaction may utilize controlled rate downflow of the reagent solution through the solid support bed, as in conventional packed bed SPOS. Once the capping reaction is finished, the capping solution 244 may exit the reactor 202 via the port 212 (with or without the assistance of pressure). After removal of the capping solution 244, a step of washing may occur. If the capping reaction occurred before the oxidation reaction, this would be the third washing; however, if the capping reaction occurs after the oxidation step, this would be the fourth washing step. This washing may occur in the same manner as outlined herein.

After the oxidation reaction or the capping reaction (and the washing), the cycle may then "begin again", in order to add a new posphoroamidite to the growing chain. This will involve starting with the de-protection reaction (e.g., adding the de-protecting solution) and then completing the cycle as many times as necessary in order to obtain the desired product.

In some embodiments, the solutions (such as the washing solutions, the activated amidite solution, the capping solution, the oxidation solution, and/or the de-protecting solution) may exit the reactor by passing through the filter at the bottom of the reactor. Of course, other ways of removing these solutions may also be used.

In the embodiment shown in FIG. 2, the 'upward and downward' flow through the reactor bed is accomplished via pressure and causes the fluids to move in a vertical direction. However, as used herein, 'upward and downward' also includes causing the fluid to move in a horizontal direction (e.g., from one side of the reactor through the bed to the other) or diagonally through the reactor. Any type of 'oscillation' of the fluid through the reactor is included within the meaning of 'upward and downward' flow. Such movement may also be accomplished via pressure differentials and is within the knowledge of those skilled in the art. The mixing may be caused by inter gas bubbling up from the bottom of the reactor. The bubbling gas may be intermittent, so that the liquid alternates pushing down through the solid support and fluidizing with the solid support, or it may be a constant bubbling throughout the entire reaction time. The intermittent fluidization may be more important for tall skinny reactor to quickly achieve complete liquid contacting with all of the solid support, and it may be less important for larger diameter reactors.

In example 1-4 and 6-10, the wash solvent is drained out the bottom of the filter reactor before the reagents are charged. Likewise, the reaction solutions are drained out the bottom of the filter reactor before the next wash solvents are charged. This reduces back-mixing and makes the process more efficient compared to packed bed reactors that do not drain in-between parts of the cycle.

Figure 6:
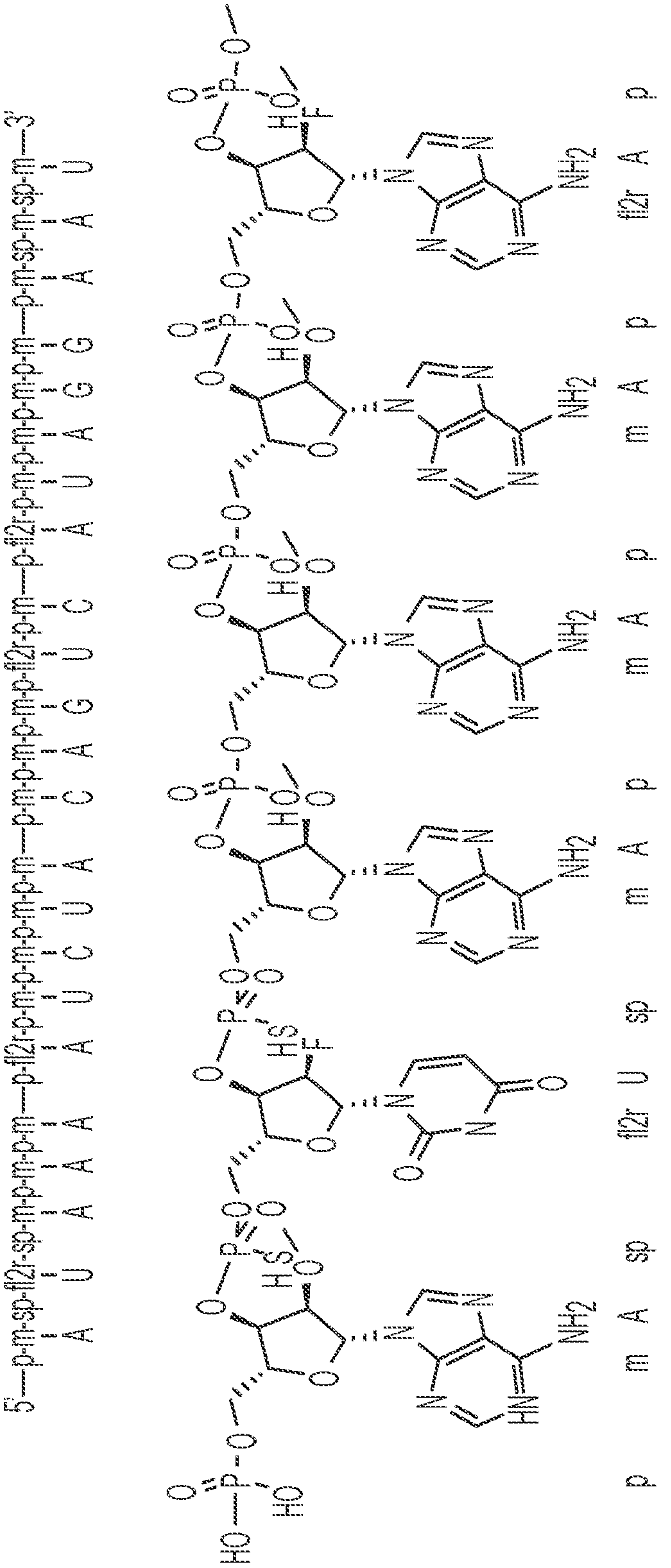
FIG. 6 is a schematic view of a molecule that may be made using the techniques outlined herein.
Figure 6:
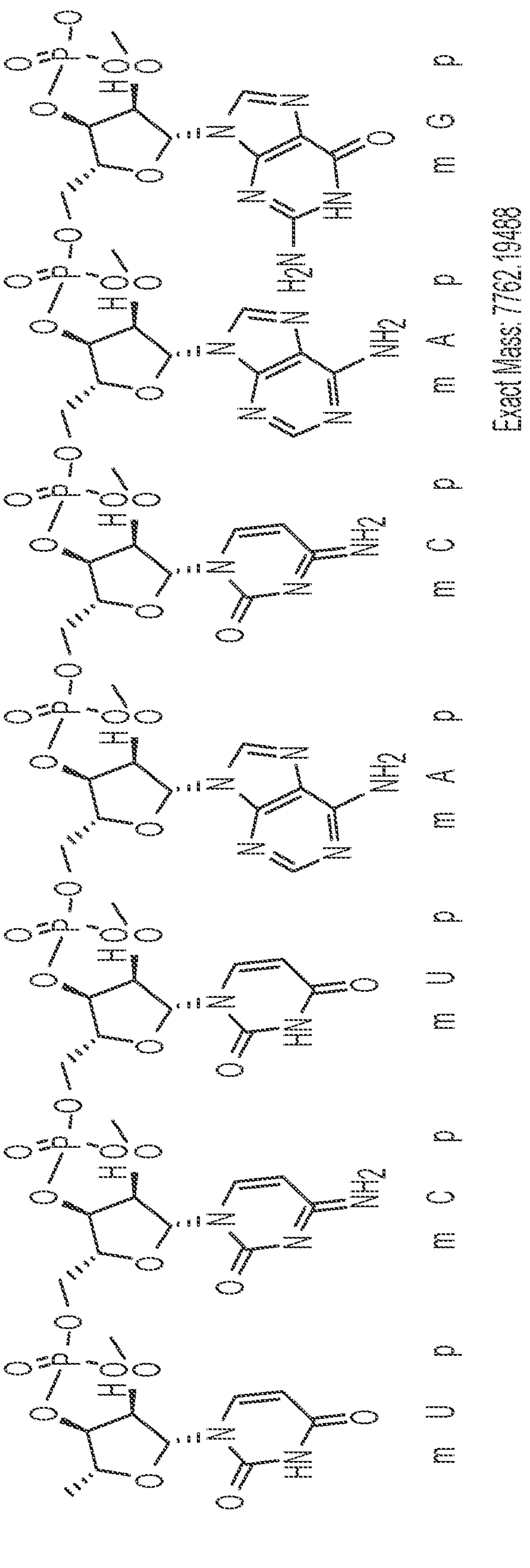
Figure 6:
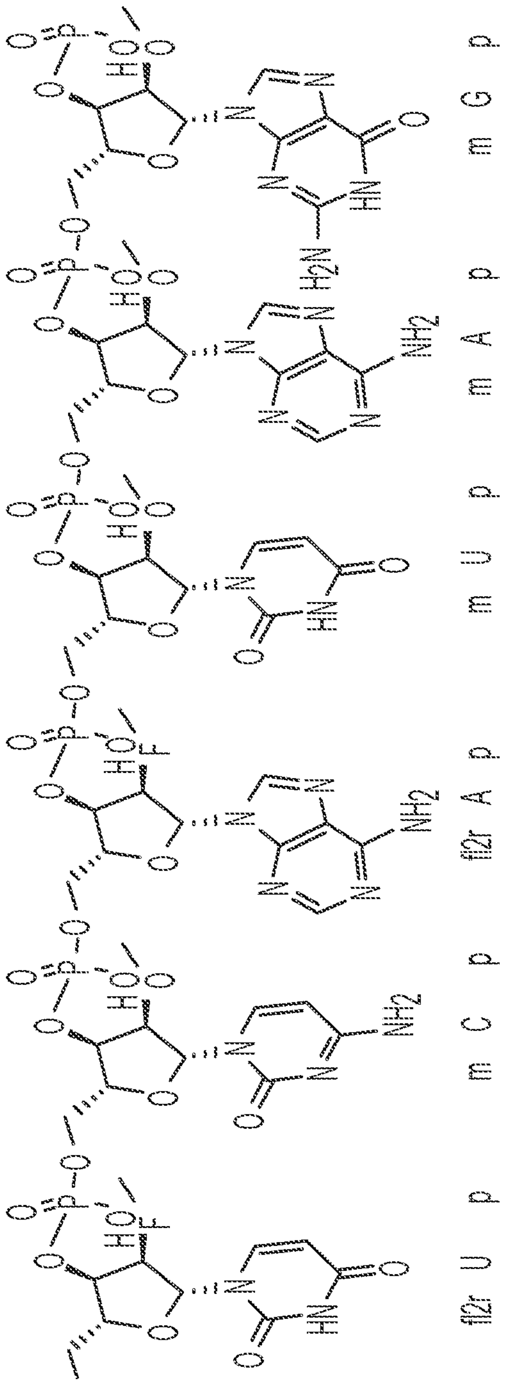
Figure 6:
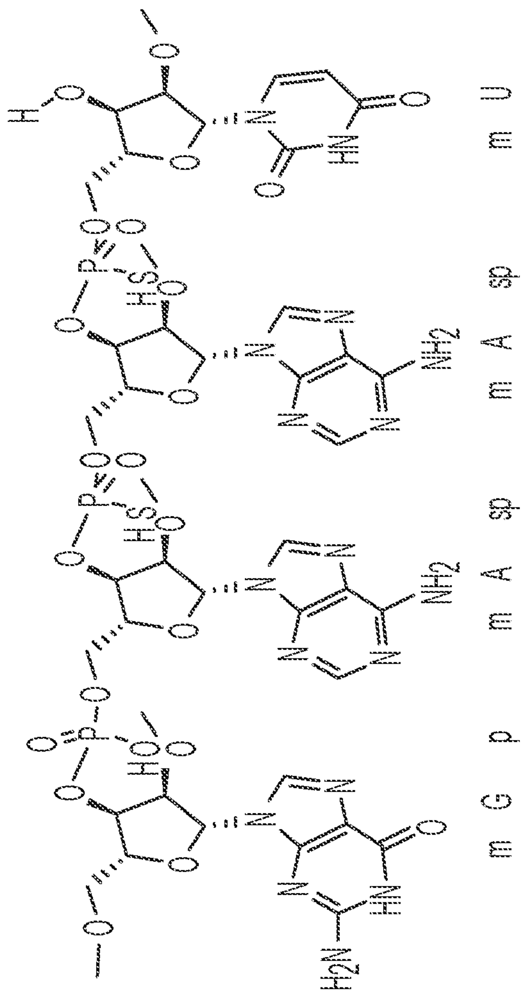

Example 1—Preparation of HPRT Div22 Antisense Strand Using Liquid Upflow Fluidization HPRT Div22 Antisense strand has the following sequence: 5' [Phos]mA*fU* mA mA mA fA mU mC mU mA mC mA mG fU mC fA mU mA mG mG mA*mA*mU where * stands for P=S linkage and all other amidites have P=O linkage and RNA1{p.m(A)[sp].[fl2r](U)[sp].m(A)p.m(A)p.m(A)p.[fl2r](A)p.m(U)p.m(C)p.m(U)p.m(A)p.m(C)p.m(A)p.m(G)p.[fl2r](U)p.m(C)p.[fl2r](A)p.m(U)p.m(A)p.m(G)p.m(G)p.m(A)[sp].m(A)[sp].m(U)]$$$$V2.0. (The structure is shown in FIG. 6).

The synthesis of this molecule using the fluidized bed method of the current invention is herein described, and comprises deblocking, coupling, oxidizing (or sulfurization), and capping steps to sequentially install the remaining phosphoramidites in the HPRT Div22 Antisense strand from 3' to 5'. The goals of Example 1 were to make the chemistry work for the first time with high purity and high yield in a research scale fluid bed reactor. The goal was not to minimize ACN wash solvent, minimize DCA reagent solution, minimize amidite equivalence, or to demonstrate tall solid support bed height. For examples that minimize the use of ACN solvent, see Example 6 at research scale and Examples 8 and 9 at pilot scale. For an example that minimizes the amount of DCA solution, see Example 7. Furthermore, in Example 1, four equivalents of amidite were use on each cycle. In contrast, Examples 2 through 9 used two equivalents of amidite for all or most cycles. Solid support bed height for Example 1 was only 2 cm maximum, whereas solid support bed height was taller for Examples 2-4 and Examples 6-10. See Example 2 for 30 cm resin bed height. A guide to all the examples in listed in Table 31.

Figure 3:
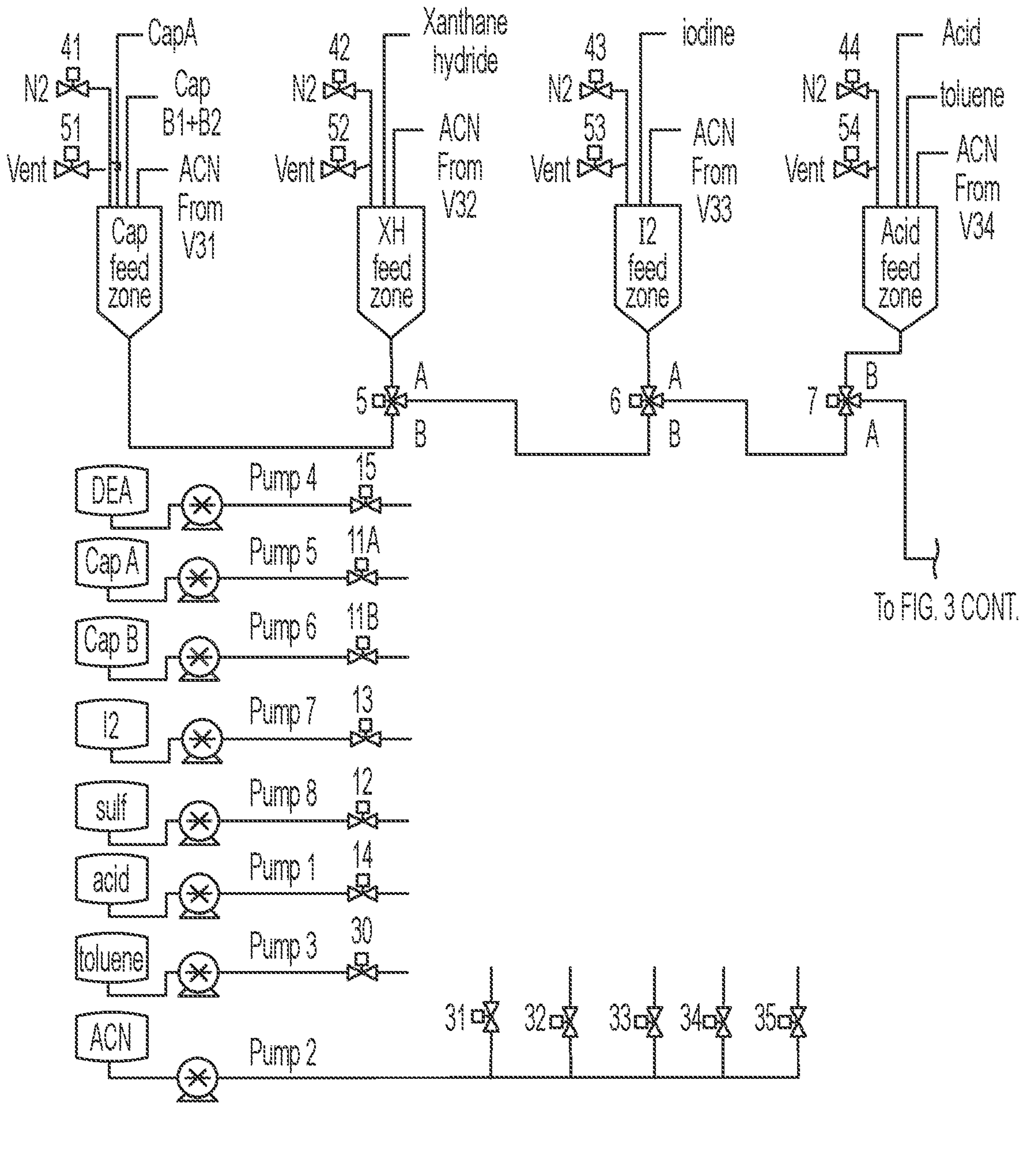
FIG. 3 is a schematic view of the small scale oscillating fluidized bed oligonucleotide synthesizer setup.
Figure 3:
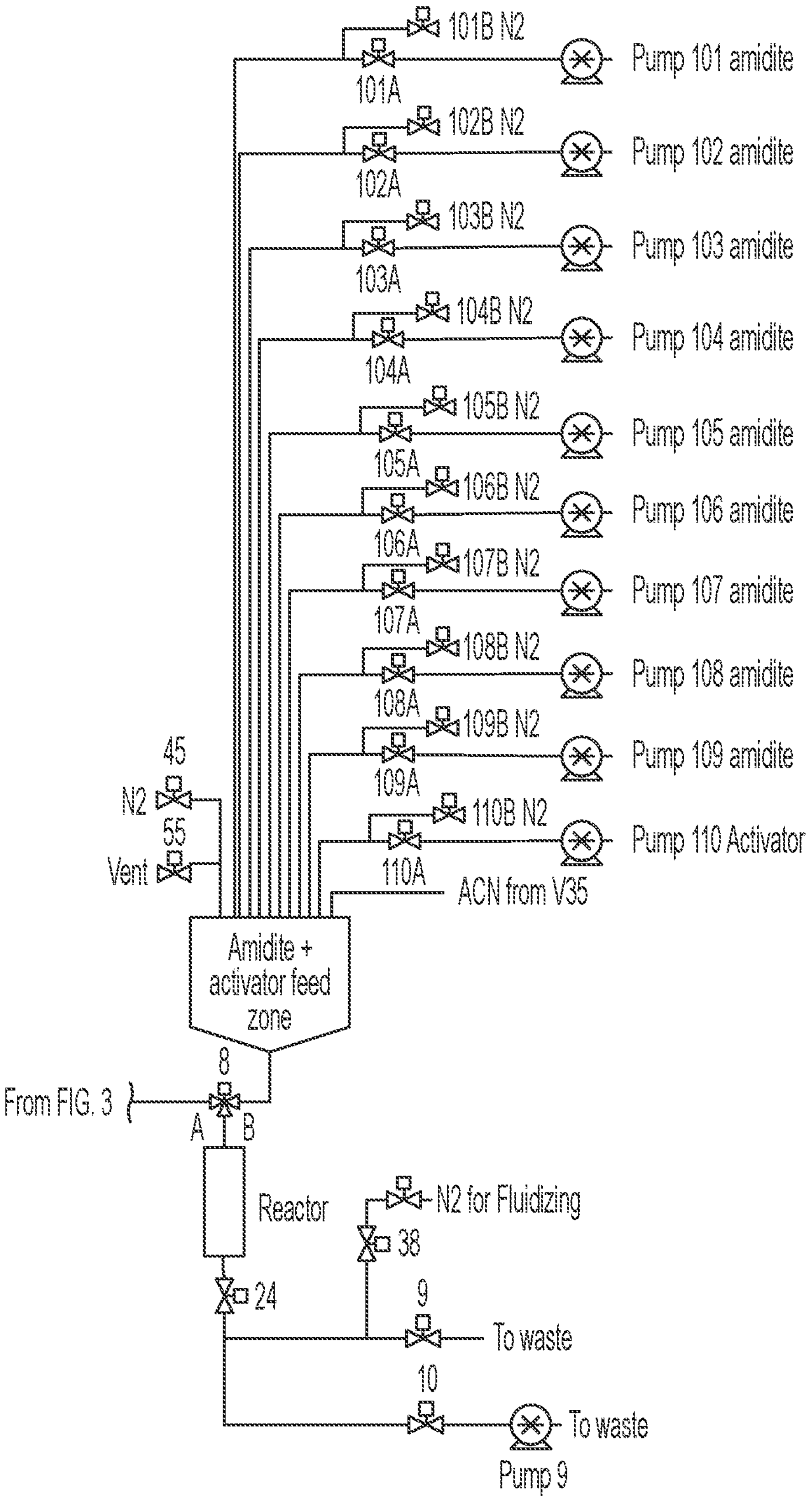

Begin with mU coupled onto NittoPhase HL 2' OMeU(bz) 300 resin, lot #E05005, 299 umol/g, using known methods (herein referred to as "mU-resin"), and refer to FIG. 3 for the setup of the synthesizer apparatus.

Prepare the reagent solutions shown in Table 1.

TABLE 1

Reagent solutions

Figure 5:
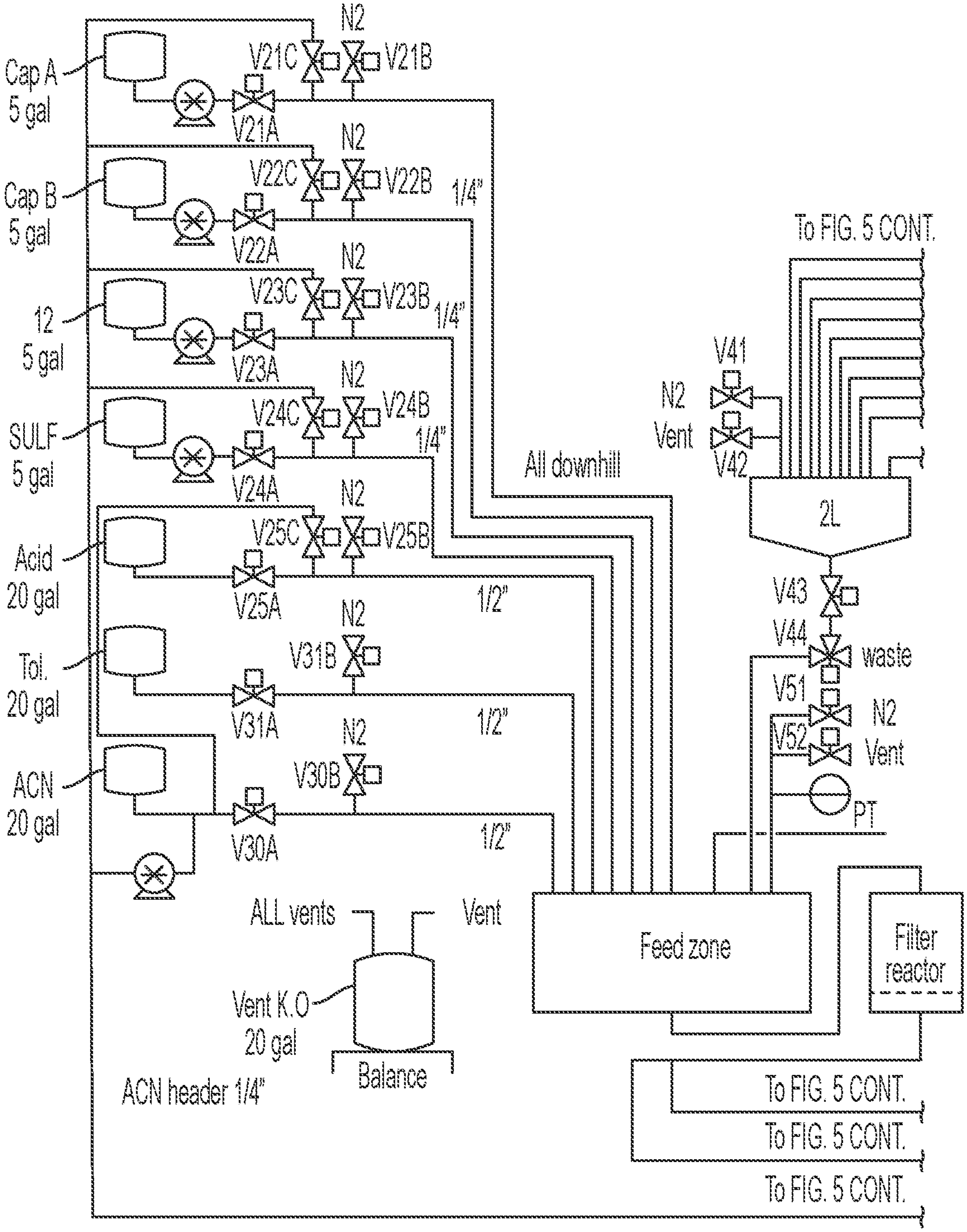
FIG. 5 is a schematic view of the pilot scale fluidized bed oligonucleotide synthesizer setup.
Figure 5:
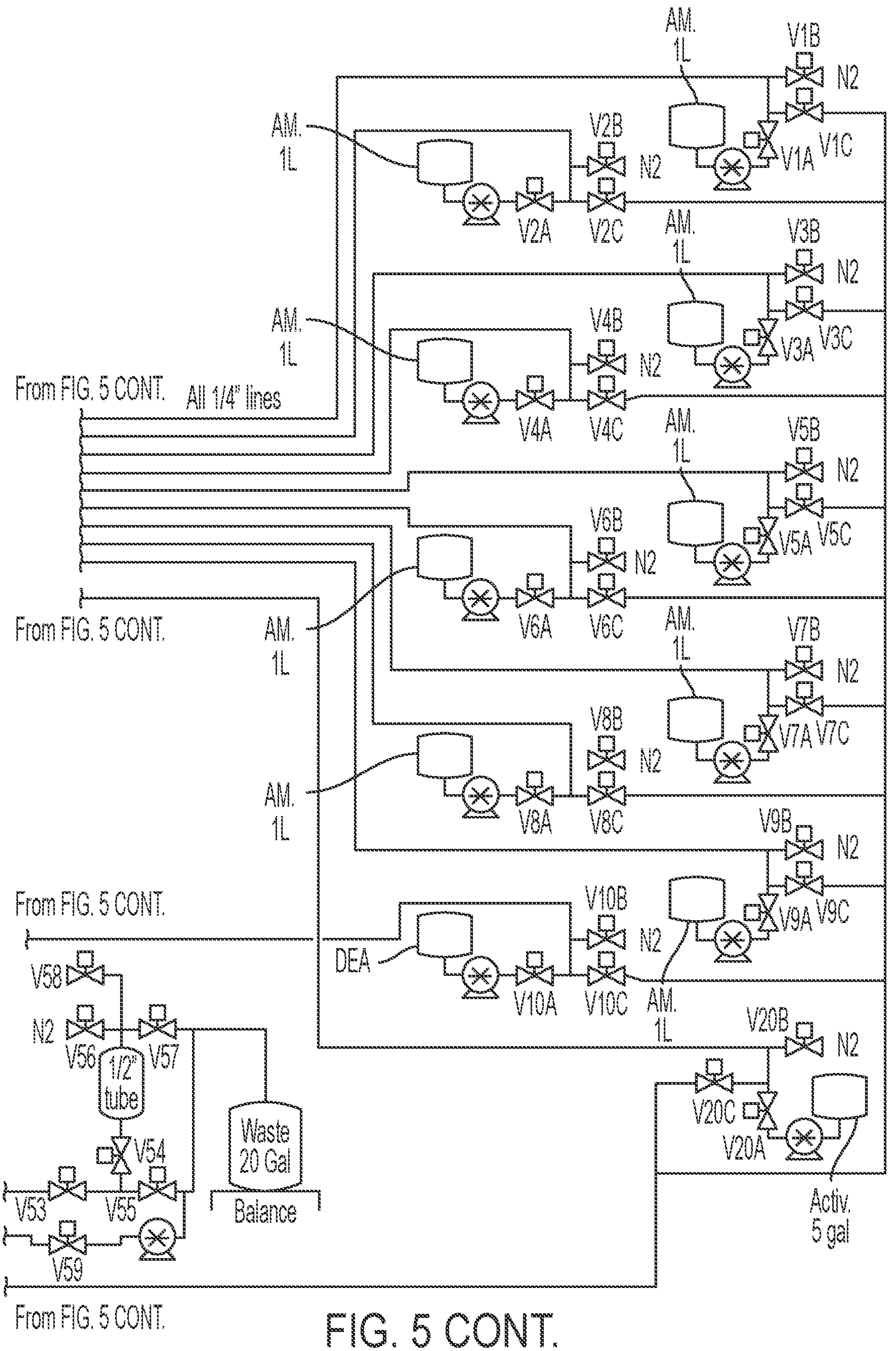

| Solution Name | Contents | Abbreviation in FIG. 3 | Abbreviation in FIG. 5 |
|---|---|---|---|
| Deblocking | 3 vol % Dichloroacetic acid (DCA) in toluene | acid | Acid |
| Activator | 0.5M 5-(Ethylthio)-1H-tetrazole in ACN | activator | Activ. 5 gal |
| Oxidization | 0.05M Iodine in pyridine/water (90/10 v/v) | I2 or iodine | I2 |
| Sulfurization | 0.02M Xanthane hydride in ACN/pyridine (70/30 v/v) | sulf, xanthane hydride, or XH | SULF |
| Capping solution A | 1-Methylimidazole/ACN (20/80 v/v) | Cap A | Cap A |
| Capping solution B | 1:1 Mixture B1 and B2, wherein B1 = 40 vol % acetic anhydride in ACN, and B2 = 60 vol % 2,6-lutidine in ACN | Cap B or Cap B1 + B2 | Cap B |

TABLE 1-continued

| Reagent solutions | | | |
|---|---|---|---|
| Solution Name | Contents | Abbreviation in FIG. 3 | Abbreviation in FIG. 5 |
| DEA | 20% diethylamine in ACN (20/80 v/v) | DEA | DEA |
| Phosphorylation | 0.1M 2-[2-(4, 4'-Dimethoxytrityloxy) ethylsulfonyl]ethyl-(2-cyanoethyl)-(N, N-diisopropyl)-phosphoramidite in ACN | (none) | (none) |

Prepare the 0.1 M amidite solutions shown in Table 2 as follows: weigh amidite solids into a bottle and insert a drypad, then add ACN to achieve a concentration of 0.1 M. Of course, a skilled artisan could also weigh solids, dissolve with ACN and then add the sieves to dry.

TABLE 2

| Amidite solutions | | |
|---|---|---|
| Amidite solution name | Amidite used | Phosphoramidite abbreviation |
| 2'-O-Me-A | DMT-2'-O-Me-A(bz) Amidite | mA |
| 2'-O-Me-C | DMT-2'-O-Me-C(Ac) Amidite | mC |
| 2'-O-Me-G | DMT-2'-O-Me-G(iBu) Amidite | mG |
| 2'-O-Me-U | DMT-2'-O-Me-U Amidite | mU |
| 2'-F-dA | DMT-2'-F-dA(Bz) Amidite | fA |
| 2'-F-dC | DMT-2'-F-dC(Ac) Amidite | fC |
| 2'-F-dG | DMT-2'-F-dG(iBu) Amidite | fG |
| 2'-F-dU | DMT-2'-F-dU Amidite | fU |

Refer to FIG. 3 for the oscillating fluidized bed oligonucleotide synthesizer setup. In FIG. 3, "ACN" refers to acetonitrile. Prime all pumps and feed lines. Place dry packs into the ACN bottle and all syringes. The amidites (Pump 101-108 amidite in FIG. 3), phosphorylation (Pump 109 amidite in FIG. 3), and activator (Pump 110 activator) solutions use syringe pumps, and all other reagent and solvent feeds use peristaltic pumps and feed vessels. Equip a 1 cm diameter, 20 cm tall reactor with a filter and automated block valve (valve 24 in FIG. 3) at the bottom, and then enough 1.59 mm i.d. tubing from the reactor to one or more outlet valves (valves 9 and 10 in FIG. 3) to contain ~2.5 mL of effluent volume. Charge the reactor with 0.1040 g of the mU-resin. Starting bed height of the dry resin was ~0.3-0.4 cm. For each phosphoramidite added in the synthesis, perform the deblocking, coupling, oxidizing (or sulfurization where there is a P=S linkage in the sequence), and capping steps sequentially as described below.

At each step, resin bed fluidization is performed at two different times: first when the reagent mixture is charged to the reactor and the resin is exposed to it, and second when the wash solvent is charged to the reactor. However, during the coupling reaction the fluidization continues for the entire 10-minute coupling time. In this example, during both reagent charging and solvent washing, the reagent mixture or wash solvent (or portion thereof) is added to the feed zone and nitrogen pressure is applied, forcing the liquid into the reactor. Referring to FIG. 3, this is achieved by closing valves 9 and 10, opening valve 24, and applying nitrogen pressure from the appropriate inlet (valves 41, 42, 43, 44, or 45). This forces the liquid in the reactor to flow through the resin bed and into the tubing between the reactor and valves 9 and 10 as the pressure gradient is equalized between the top of the reactor and the tubing between the bottom of the reactor and valves 9 and 10. The pressure at the top of the reactor is then released by opening the appropriate vent (valves 51, 52, 53, 54, or 55), creating a pressure gradient which is equalized to atmospheric pressure as the liquid flows up from the bottom of the reactor, agitating and fluidizing the resin bed. The nitrogen pressurizing and venting process is repeated the number of times specified, for at least a duration sufficient to fluidize the resin bed each time. If only a portion of reagent mixture or wash solvent is used in fluidizing the bed, the remaining reagent mixture or wash solvent is passed through the resin in a "plug flow" manner, wherein valve 9 is closed, valve 10 is opened, nitrogen pressure is applied to the top of the reactor, and pump 9 is actuated to meter liquid out of the bottom of the reactor as liquid (reagent mixture or wash solvent) is added to the top of the reactor.

The amidite+activator equivalents, DCA equivalents, and the solvent wash volumes were very high in this first example compared to all subsequent examples because this was an early demonstration of an early prototype. The reader will see that the process is improved and wash solvent is decreased with progression through the examples and embodiments. See Table 31 for a summary of the embodiments.

Deblocking: Turn valve 8 to A, valve 7 to B, and close valve 24. Charge 8 mL of the deblocking solution (Table 1) into the feed zone, then push it into the reactor with nitrogen pressure for 8 seconds. Open valve 24. The outlet valves to waste (valves 9 and 10 in FIG. 3) are closed. Apply nitrogen pressure to the reactor for 5 seconds, which pushes ~1.5 mL of the reagent solution down through the resin bed and out the filter bottom reactor into the process tubing and compresses the gas pocket in the tubing. Vent the pressure from the top of the reactor for 5 seconds, causing back-flow of reagent liquid back up into the bottom of the reactor to agitate and fluidize the resin bed. Repeat the fluidization process (pressurizing with nitrogen for 5 seconds and venting for 5 seconds). Open the valve to waste (valve 10) and pump the deblocking solution through the resin bed with Pump 9 at a rate of 16 mL per 330 seconds for 330 seconds. In parallel to Pump 9 pumping, open valve 14 and start Pump 1 feeding the deblocking solution at 10 mL/min until 8 mL has been pumped (Pump 1 finishing before Pump 9) Liquid pumping into the acid feed zone from Pump 1 simultaneously flows into the reactor to maintain liquid level above the resin bed and keep the flow going for the 330 second duration. The total time the resin contacts the deblocking solution before the next ACN washing step is 6.9 min. Close valve 10 and perform ACN wash procedure A once, then perform ACN wash procedure B twice.

ACN Wash Procedure A:

Open waste valve 9, charge ACN (4 mL) into the feed zone, then close valve 9 and push it into the reactor with nitrogen pressure for 8 seconds. Fluidize the resin bed five times as above, pressurizing the reactor with nitrogen for 5 seconds and venting for 5 seconds. Open valve 9 to waste and push to waste with nitrogen pressure for 8 seconds.

ACN Wash Procedure B:

Open valve 9 (to waste) and charge ACN (12 mL) into the feed zone, then close valve 9 and push it into the reactor with nitrogen pressure for 8 seconds. Fluidize the resin bed three times as above, pressurizing the reactor with nitrogen for 5 seconds and venting for 5 seconds. Open valve 10 and pump with Pump 9 at a rate of 20 mL per 110 seconds for 110 seconds. In parallel to Pump 9 pumping, open valve 34 and start Pump 2 feed at 40 mL/min until 8 mL of ACN has been pumped (Pump 2 finishing before Pump 9). Liquid pumping into the feed zone from Pump 2 simultaneously flows into the reactor to maintain liquid level above the resin bed and keep the flow going for the 110 seconds. Upon finishing, close valve 10.

Coupling reaction: After deblocking wash, the next sequential phosphoramidite is coupled, installed in sequential steps from 3' to 5'. For each phosphoramidite to be coupled in the sequence, perform the coupling reaction procedure essentially as described as follows, using the amidite solution (listed in Table 2) corresponding to the phosphoramidite in the sequence. Turn valve 8 to B. Prewash the amidite zone and flow path to the reactor twice, each time by pumping 4 mL ACN into the amidite feed zone with valve 9 closed, then open valve 9 and push with nitrogen pressure to waste for 8 seconds. Pump first the activator solution (1.2 mL, 20 equiv., Table 1), and then the appropriate amidite solution from Table 2 (1.2 mL, 4.0 equiv.) into the feed zone. Close valve 9 and 24 and push the mixture in the feed zone into the reactor with nitrogen pressure for 5 seconds, then open valve 24 and continue nitrogen pressure for 8 seconds.

With the amidite and activator solutions mixed with the resin, repeatedly fluidize the bed as follows with valve 24 open and valve 9 closed: apply nitrogen pressure to the top of the reactor for 5 seconds, then vent pressure out of the top of the reactor for 5 seconds. Repeat this process repeatedly for 10 min, then open valve 9 and apply nitrogen pressure for 8 seconds to the top of the reactor, draining liquid from the bottom of the reactor to waste. Pump ACN (10 mL) into the amidite feed zone and push it through the reactor with nitrogen pressure for 30 seconds, then repeat this ACN wash once more.

Oxidation reaction (when required instead of Sulfurization): After the coupling reaction wash, perform the oxidation reaction essentially as described as follows. Turn valves 6, 7, and 8 to A, and open valve 9. Pump oxidation solution (Table 1, 4.5 mL) into the feed zone, close valve 9, and push it into the reactor with nitrogen pressure for 8 seconds. Fluidize the reactor bed twice as follows: pressurize the top of the reactor with nitrogen pressure for 5 seconds, then release the nitrogen pressure by venting for 5 seconds. Open valve 10 and pump 4.5 mL of liquid volume with pump 9 over 40 seconds, then close valve 10. Open valve 9 and pump ACN (4 mL) into the feed zone, then close valve 9 and push the ACN into the reactor with nitrogen pressure for 8 seconds. Fluidize the reactor bed five times as follows: pressurize the top of the reactor with nitrogen pressure for 5 seconds, then release the nitrogen pressure by venting for 5 seconds. Open valve 9 and push the liquid in the reactor to waste with nitrogen pressure from the top of the reactor for 8 seconds.

Perform the following "plug flow" ACN wash twice after the oxidation reaction. Open valve 9 and pump ACN into the feed zone (8 mL). Close valve 9 and push the liquid into the reactor using nitrogen pressure for 8 seconds. Fluidize the reactor bed twice as follows: pressurize the top of the reactor with nitrogen pressure for 5 seconds, then release the nitrogen pressure by venting for 5 seconds. Open valve 10 and pump 12 mL of liquid volume with pump 9 over 95 seconds. In parallel to Pump 9 pumping, open valve 33 and start Pump 2 feed at 30 mL/min until 4 mL of ACN has been pumped (Pump 2 finishing before Pump 9). Liquid pumping into the feed zone from Pump 2 simultaneously flows into the reactor to maintain liquid level above the resin bed and keep the flow going for the 95 seconds. Upon finishing, close valve 10.

Sulfurization (thiolation) reaction (when required instead of Oxidation): After the coupling reaction wash, perform the thiolation reaction essentially as described as follows. Turn valve 6 to B, valves 5, 7, and 8 to A, and open valve 9. Pump sulfurization solution (Table 1, 4.5 mL) into the feed zone, close valve 9, and push it into the reactor with nitrogen pressure for 8 seconds. Fluidize the reactor bed twice as follows: pressurize the top of the reactor with nitrogen pressure for 5 seconds, then release the nitrogen pressure by venting for 5 seconds. Open valve 9 and push the liquid in the reactor to waste with nitrogen pressure from the top of the reactor for 8 seconds. Perform the same "plug flow" ACN wash twice as described in the oxidation reaction procedure, except that the wash comes through the "XH feed zone" (FIG. 3).

Capping reaction: After the oxidation (or sulfurization) reaction wash, perform the capping reaction essentially as described as follows. Turn valves 5 and 6 to B, and valves 7 and 8 to A. Open valve 9. Simultaneously pump capping solution A (Table 1, 2.1 mL) and capping solution B (Table 1, 2.1 mL) into the feed zone and then close valve 9. Push the liquid into the reactor with nitrogen pressure for 8 seconds. Fluidize the reactor bed twice as follows: pressurize the top of the reactor with nitrogen pressure for 5 seconds, then release the nitrogen pressure by venting for 5 seconds. Open valve 10 and pump 4.2 mL of liquid volume over 100 seconds. Close valve 10 and perform the same "plug flow" ACN wash twice as described in the oxidation reaction procedure, except that the wash comes through the "Cap feed zone" (FIG. 3).

After the final phophoroamidite cycle is complete, repeat the cycle using the phosphorylating solution (Table 1) instead of amidite. After the phosphorylating reagent is coupled and oxidized, repeat the deblocking step and then solvent washing. Wash the resin with DEA solution (Table 1) for 10 minutes. Wash with ACN and dry with nitrogen blowing down through the resin bed to give 380 mg of dry resin. Starting resin mass was 104 mg. This corresponds to 276 mg of weight gain, which is 8.88 g/mmol therefore the crude mass yield of the protected oligonucleotide product is 96% by mass gain.

Perform the cleavage and deprotection reaction with concentrated $NH_4OH$ solution at 50° C. for 4 hours. UPLC shows the cleaved and deprotected oligonucleotide product is 82% pure by peak area percent, as shown in the Table of UPLC results for examples 1 through 5 (Table 13). LCMS analysis confirms that the main product peak represents the correct HPRT div22 AS strand.

Referring to FIG. 3 and considering Example 1, the detailed automation procedure for the sequence of pumps and valve operations is written as follows.

Below is shown (and will be described in conjunction with the embodiment of FIG. 3 and considering Example 1), an example of the detailed automation procedure for the sequence of pumps and valve operations.

Detailed automation procedure for the sequence of pumps and valve operations for Example 1. Key: "0" means "open"; "C" means "close"; "P" means "pump", e.g. "P9" refers to "pump 9" in FIG. 3.

Deblocking
- valve 8 to A,
- Valve 7 to B,

Push acid solution into acid feed zone
O 9
O 54
O 14
Pump acid into acid feed zone (8 mL)
C 14
C 54
C 9

Push acid solution into reactor and fluidize twice to achieve complete liquid-solid contacting and re-set bed flat with no channels
O 44
Wait "time to push into reactor" (8 seconds)
Run the next 6 rows 2 times.
O 44
Wait "N2 time to push bed down" (5 seconds)
C 44
O 54
Wait "vent time to fluidize bed" (5 seconds)
C 54

Pump the acid solution through the resin plug flow for the reaction.
O 44
O 10
Start pump P9 at rate of 16 mL per 330 seconds for the next 330 seconds.
In parallel to P9 pumping, open 14 and start P1 feed at 10 mL/min until pumped 8 mL. P1 finishes before P9. Liquid pumping into acid feed zone from P1 simultaneously flows into the reactor to maintain liquid level above the resin bed and keep the plug flow going for the 330 seconds.
C 14
C 44
C 10

Pump ACN into acid feed zone
O 9
O 34
O 54
Pump "volume ACN for fluid bed wash deblock" (4 mL)
C 34
C 54
C 9

Small fluid bed ACN wash after deblock
O 44
Wait "time to push into reactor" (8 seconds)
Repeat the next 6 rows 5 times.
O 44 Wait "N2 time to push bed down" (5 seconds)
C 44
O 54
Wait "vent time to fluidize bed" (5 seconds)
C 54
O 44
O 9
Wait "time to push to waste after fluidizing" (8 seconds)
C 44

Plug flow wash after deblock (run this 2 times). Plug flow wash starts with 3 fluidizations to set the bed flat and eliminate channeling.
O 9
O 34
O 54
Pump ACN into feed zone (12 mL)
C 34
C 54
C 9
O 44
Wait "time to push into reactor" (8 seconds)
Repeat the next 6 rows 3 times.
O 44
Wait "N2 time to push bed down" (5 seconds)
C 44
O 54
Wait "vent time to fluidize bed" (5 seconds)
C 54
O 44
O 10
Start pump P9 at rate of 20 mL per 110 seconds for the next 110 seconds.
In parallel to P9 pumping, open 34 and start P2 feed at 40 mL/min until pumped 8 mL ACN. P2 finishes before P9. Liquid pumping into acid feed zone from P2 simultaneously flows into the reactor to maintain liquid level above the resin bed and keep the plug flow going for the 110 seconds.
C 34
C 44
C 10

Coupling reaction
Valve 8 to B

Pre-wash amidite zone and flow path to reactor before coupling (run this 2 times)
O 35
O 55
Pump P2, 4 mL ACN into amidite feed zone.
C 35
C 55
O 9
O 45
Wait time to push to waste (8 seconds)
C 45

Measure out amidite and activator into amidite feed zone
open valve 110A
pump activator specified volume (1.2 mL).
close valve 110A
Open valve 110B
Wait 5 seconds to push activator solution into amidite mix zone
Close valve 110B
open valve 101A. NOTE: Valve 101 was used for mA. Each of the amidites had
its own valves and its own feed line into the activation zone.
pump amidite specified volume (1.2 mL).
close valve 101A
Open valve 101B
Wait 5 seconds to push amidite solution into amidite mix zone
Close valve 101B Push amidite reaction solution into reactor and mix with resin for 10 minutes.
C 55
C 9
C 24
O 45
Wait 5 seconds
O 24
Wait "time to push into reactor" (8 seconds)
Repeat the next 7 rows "fluid bed coupling time" (10 minutes).
O 45
Wait "N2 time to push bed down" (5 seconds)
C 45
O 55

Wait "vent time to fluidize bed" (5 seconds)
C 55
Wait "time between fluidizations during coupling" (2 seconds)
After the "fluid bed coupling time" is over
O 45
O 9
Wait "time to push to waste after fluidizing" (8 seconds)
C 45
Solvent wash with ACN after coupling (run this 2 times)
O 35
O 55
Pump "volume ACN for single pass wash coupling" (10 mL)
C 35
C 55
O 9
O 101B, 102B, 103B, 104B, 105B, 106B, 107B, 108B, 109B, 110B at the same time
Wait "time to push to waste single pass coupling wash" (30 seconds)
C 101B, 102B, 103B, 104B, 105B, 106B, 107B, 108B, 109B, 110B at the same time
C 9
Oxidation (when required instead of Sulfurization)
O 9
Valve 8 to A
Valve 7 to A
Valve 6 to A
Pump iodine solution into oxidation feed zone
O 13
O 53
pump 4.5 mL iodine
C 13
C 53
C 9
Push iodine solution into reactor and fluidize twice to re-set bed flat with no channels
O 43
Wait "time to push into reactor" (8 seconds)
run the next 6 rows 2 times.
O 43
Wait "N2 time to push bed down" (5 seconds)
C 43
O 53
Wait "vent time to fluidize bed" (5 seconds)
C 53
Pump the iodine solution through the resin plug flow for the reaction.
O 43
O 10
Start pump P9 at rate of 4.5 mL per 40 seconds for the next 40 seconds.
C 43
C 10
Small fluid bed ACN wash after oxidation
O 9
O 33
O 53
Pump 4 mL ACN into oxidation feed zone
C 33
C 53
C 9
O 43
Wait "time to push into reactor" (8 seconds)
Run the next 6 rows 5 times.
O 43
Wait "N2 time to push bed down" (5 seconds)
C 43
Wait "vent time to fluidize bed" (5 seconds)
C 53
O 43
O 9
Wait "time to push to waste after fluidizing" (8 seconds)
C 43
Plug flow wash after oxidation (run this 2 times). Plug flow wash starts with 3 fluidizations to set the bed flat and eliminate channeling.
O 9
O 33
O 53
Pump ACN into feed zone (8 mL)
C 33
C 53
C 9
O 43
Wait "time to push into reactor" (8 seconds)
Run the next 6 rows 3 times.
O 43
Wait "N2 time to push bed down" (5 seconds)
C 43
O 53
Wait "vent time to fluidize bed" (5 seconds)
C 53
O 43
O 10
Start pump P9 at rate of 12 mL per 95 seconds for the next 95 seconds.
In parallel to P9 pumping, open 33 and start P2 feed at 30 mL/min until pumped 4 mL ACN. P2 finishes before P9. Liquid pumping into oxidation feed zone from P2 simultaneously flows into the reactor to maintain liquid level above the resin bed and keep the plug flow going for the 95 seconds.
C 33
C 43
C 10
Sulfurization (when required instead of oxidation)
O 9
Valve 8 to A
Valve 7 to A
Valve 6 to B
Valve 5 to A
Pump sulfurization solution into sulfurization feed zone
O 12
O 52
pump sulfurization solution (4.5 mL)
C 12
C 52
C 9
Push sulfurization solution into reactor and fluidize twice to re-set bed flat with no channels
O 42
Wait "time to push into reactor" (8 seconds)
run the next 6 rows 2 times.
O 42
Wait "N2 time to push bed down" (5 seconds)
C 42
O 52
Wait "vent time to fluidize bed" (5 seconds)
C 52

Pump the sulfurization solution through the resin plug flow for the reaction.

O 42

O 10

Start pump P9 at rate of 4.5 mL per 90 seconds for the next 90 seconds.

C 42

C 10

Small fluid bed ACN wash after sulfurization

O 9

O 32

O 52

Pump 4 mL ACN into sulfurization feed zone

C 32

C 52

C 9

O 42

Wait "time to push into reactor" (8 seconds)

Run the next 6 rows 5 times.

O 42

Wait "N2 time to push bed down" (5 seconds)

C 42

O 52

Wait "vent time to fluidize bed" (5 seconds)

C 52

O 42

O 9

Wait "time to push to waste after fluidizing" (8 seconds)

C 42

Plug flow wash after sulfurization (run this 2 times). Plug flow wash starts with 2 fluidizations to set the bed flat and eliminate channeling.

O 9

O 32

O 52

Pump ACN into feed zone (8 mL)

C 32

C 52

C 9

O 42

Wait "time to push into reactor" (8 seconds)

Run the next 6 rows 2 times.

O 42

Wait "N2 time to push bed down" (5 seconds)

C 42

O 52

Wait "vent time to fluidize bed" (5 seconds)

C 52

O 42

O 10

Start pump P9 at rate of 12 mL per 95 seconds for the next 95 seconds.

In parallel to P9 pumping, open 32 and start P2 feed at 30 mL/min until pumped 4 mL ACN. P2 finishes before P9. Liquid pumping into sulfurization feed zone from P2 simultaneously flows into the reactor to maintain liquid level above the resin bed and keep the plug flow going for the 95 seconds.

C 32

C 42

C 10

Capping

Valve 8 to A

Valve 7 to A

Valve 6 to B

Valve 5 to B

Pump capping solutions into capping feed zone

O 11A

O 11B

O 51

Simultaneously pump capA "volume capA" (2.1 mL) and pump capB "volume capB" (2.1 mL)

C 11A

C 11B

C 51

C 9

Push capping solution into reactor and fluidize twice to re-set bed flat with no channels

O 41

Wait "time to push into reactor" (8 seconds)

Run the next 6 rows 2 times.

O 41

Wait "N2 time to push bed down" (5 seconds)

C 41

O 51

Wait "vent time to fluidize bed" (5 seconds)

C 51

Pump the capping solution through the resin plug flow for the reaction.

O 41

O 10

Start pump P9 at rate of 4.2 mL per 100 seconds for the next 100 seconds.

C 41

C 10

Plug flow wash after capping (run this 2 times). Plug flow wash starts with 2 fluidizations to set the bed flat and eliminate channeling.

O 9

O 31

O 51

Pump ACN into capping feed zone (8 mL)

C 31

C 51

C 9

O 41

Wait "time to push into reactor" (8 seconds)

Run the next 6 rows 2 times.

O 41

Wait "N2 time to push bed down" (5 seconds)

C 41

O 51

Wait "vent time to fluidize bed" (5 seconds)

C 51

O 41

O 10

Start pump P9 at rate of 12 mL per 95 seconds for the next 95 seconds.

In parallel to P9 pumping, open 31 and start P2 feed at 30 mL/min until pumped 4 mL ACN. P2 finishes before P9. Liquid pumping into capping feed zone from P2 simultaneously flows into the reactor to maintain liquid level above the resin bed and keep the plug flow going for the 95 seconds.

C 31

C 41

C 10

Example 2—Preparation of HPRT Div22 Antisense Strand with Up to 30 cm Resin Bed Height The same HPRT Div22 Antisense strand is prepared as in Example 1. The synthesis of this molecule using the fluidized bed method of the current invention is herein described, and comprises deblocking, coupling, oxidizing (or sulfurization), and capping steps to sequentially install the remaining phosphoramidites. The main differences are that the reactor geometry and the fluidization method are modified to enable much taller resin bed height. The process in this example is run at 180 μmol scale with the resin bed height reaching 25 cm ACN solvent wet by the end of the experiment. A maximum resin bed height of 30 cm is reached during downflow portion of the final deblocking step. Maximum pressure drop across the resin bed is 20 psig during the experiment. The reactor has a 0.63 cm inside diameter bottom section 32 cm tall, and a 4.7 cm diameter cone-bottom top section 10.5 cm tall. The reactor is equipped with a stainless-steel filter screen at the bottom of the 0.63 cm diameter section.

Each time the resin bed fluidizes, nitrogen pushes the liquid and solids up from the 0.63 cm i.d. section into the conical bottom upper section, where the nitrogen bubbling completely mixes and fluidizes solids. The fluidized slurry was subsequently pushed down into the 0.63 cm i.d. section to re-form the resin bed after each fluidization while a small portion of the liquid exited the bottom of the reactor through the filter screen. Incoming liquid from the feed zones pushed into the top of the 4.7 cm i.d. section through a ⅛" o.d. stainless steel tube that was angled toward the wall and then angled in the radial direction so that the incoming liquid would vortex around the inner wall to prevent splashing. 2 equivalents of amidite were used for the couplings in Example 2, compared to 4 equivalents used in Example 1.

Begin with mU coupled onto NittoPhase LL 2' OMeU(bz) 250 resin using known methods (herein referred to as “mU-resin”) and refer to FIG. 3 for the setup of the synthesizer apparatus. Resin batch was G07010, loading 246 umol/g. Initial weight of dry resin put inside the reactor was 0.7322 g. Therefore, the scale of the experiment was 180.1 umol.

Use the reagent solutions as described in Table 3 v

TABLE 3

Reagent solutions for example 2.

| Solution Name | Contents | Lot | Vendor |
|---|---|---|---|
| Main solvent | ACN | 205244 | Fisher |
| Deblocking | 3 vol % Dichloroacetic acid (DCA) in toluene | DX727US | Honeywell |
| Activator | 0.5M 5-(Ethylthio)-1H-tetrazole in ACN | DW336US | Honeywell |
| Capping solution A | 1-Methylimidazole/ACN (20/80 v/v) | DZ847 | Honeywell |
| Capping solution B | 1:1 Mixture B1 and B2 | | |
| Capping solution B1 | 40 vol % acetic anhydride in ACN | DX994US | Honeywell |
| Capping solution B2 | 60 vol % 2,6-lutidine in ACN | DY020US | Honeywell |
| DEA | 20% diethylamine in ACN (20/80 v/v) | | Honeywell |
| Oxidization | 0.05M Iodine in pyridine/water (90/10 v/v) | PY761 | Honeywell |
| Sulfurization | 0.2M Xanthane hydride in ACN/pyridine (70/30 v/v) | | |
| Phosphorylation | 0.1M 2-[2-(4, 4'-Dimethoxytrityloxy) ethylsulfonyl]ethyl-(2-cyanoethyl)-(N, N-diisopropyl)-phosphoramidite in ACN | | Honeywell |

Prepare the 0.1 M amidite solutions shown below in Table 4. Weigh amidite solids into a bottle and insert a drypad, then add ACN to achieve a concentration of 0.1 M.

TABLE 4

Amidite solution makeup for example 2.

| Amidite solution name | Amidite used | Vendor | Lot | mass (g) | ACN (mL) |
|---|---|---|---|---|---|
| 2'-O-Me-A | DMT-2'-O-Me-A(bz) Amidite | ThermoFisher | VB2462 | 5.3786 | 60 |
| 2'-O-Me-C | DMT-2'-O-Me-C(Ac) Amidite | ThermoFisher | VD1432 | 2.1442 | 25 |
| 2'-O-Me-G | DMT-2'-O-Me-G(iBu) Amidite | ThermoFisher | VB2272 | 2.2338 | 25 |
| 2'-O-Me-U | DMT-2'-O-Me-U Amidite | ThermoFisher | VB2282 | 1.9664 | 25 |
| 2'-F-Da | DMT-2'-F-dA (Bz) Amidite | ThermoFisher | VB2242 | 2.2836 | 25 |
| 2'-F-dU | DMT-2'-F-dU | ThermoFisher | VB2262 | 1.933 | 25 |
| Phos | Amidite | Hongene | LPR22B1A1 | N/A | N/A |

Prime all pumps and feed lines. Place dry packs into the ACN bottle and all syringes. The amidites and activator use syringe pumps, and all other reagent and solvent feeds use peristaltic pumps and feed vessels. The phos reagent used one of the amidite syringe pumps (amidite 9 pump). Equip the 0.63 cm inside diameter reactor described above with a filter. Mount the reactor on top of the automated block valve (valve 24 in FIG. 3) at the bottom, and then enough tubing from the reactor to one or more outlet valves (valves 9 and 10 in FIG. 3) to contain ~3-4 mL of effluent volume.

Overall synthesis conditions are given in Table 5.

TABLE 5

Example 2 synthesis conditions

| Item | Value | Unit |
|---|---|---|
| Resin loading | 246 | μmol/gram |
| Resin starting amount | 0.7322 | gram |
| Synthesis scale | 180.1 | μmol |
| Deblocking solution, amount per cycle | 70 for cycles 1 to 12, 87 mL for cycles 13 to 24 | mL |
| Amidite concentration | 0.1 | M in ACN |
| Amidite equivlance | 2 | eq |
| Amidite solution, amount per cycle | 3.6 | mL |
| Activator concentration | 0.5 | M in ACN |
| Activator equivalence | 10 | eq |
| Activator solution, amount per cycle | 3.6 | mL |
| Oxidization equivalence | 2.2 eq for cycles 3 and 4, 2.5 eq cycles 5-20, 23 | Eq |
| Oxidization time | 6 | min |
| Sulfurization equivalence | 13 | Eq |
| Sulfurization time | 8 | min |
| Capping solution A, amount per cycle | 6.3 | mL |
| Capping solution B, amount per cycle | 6.3 | mL |
| Capping time | 4 | min |

For each phosphoramidite added in the synthesis, perform the deblocking, coupling, oxidizing (or sulfurization where there is a P=S linkage in the sequence), and capping steps sequentially as described below.

Referring to FIG. 3 and considering Example 2, the detailed automation procedure for the sequence of pumps and valve operations is written herein. When this procedure states that liquid is pumped down through the resin bed, it means that the waste pump at the outlet of the reactor bottom runs at a target setpoint, while nitrogen pressure pushes on top of the resin bed to push the liquid down through. The purpose of the peristaltic pump (pump 9) is to meter the liquid flow through the bed at a controlled rate.

Deblocking: Turn valve 8 to A, valve 7 to B, and close valve 24. Charge 30 mL of the deblocking solution (3 vol % Dichloroacetic acid (DCA) in toluene) into the feed zone, then push it into the reactor with nitrogen pressure for 8 seconds. Open valve 24. The outlet valves to waste (valves 9 and 10 in FIG. 3) are closed. Apply nitrogen pressure to the reactor for 3 seconds. Vent the pressure from the top of the reactor for 10 seconds, while at the same time opening valve 38, causing nitrogen bubbling to agitate and fluidize the resin bed with the reagent solutions. The metering valve in series with valve 38 is adjusted so that it is high enough to get the solids and liquid to rise into the upper zone and mix together, but not excessively high so that solids do not splatter up onto the top of the upper section, and to minimize the amount of solvent stripped. Repeat the fluidization process 4 more times. Most of the resin swelling happens during the fluidizations. Open the valve to waste (valve 10) and pump the deblocking solution through the resin bed with Pump 9 at a rate of 12 mL/min for user specified time (330 seconds for cycles 7 to 12, 410 seconds for cycles 13 to 24). Total deblocking solution contact time is as follows: cycles 1 and 2 was 14 min; cycle 3 was 12 min; cycles 4 and 5 were 9 min; cycle 6 was 7 min; cycles 7 to 24 were 5.5 min. In parallel to Pump 9 pumping, open valve 14 and start Pump 1 feeding the deblocking solution at 15 mL/min until the user defined volume has pumped (40 mL for cycles 1 to 12, 57 mL for cycles 13 to 24). Pump 1 finishes before Pump 9. Liquid pumping into the acid feed zone from Pump 1 simultaneously flows into the reactor to maintain liquid level above the resin bed and keep the flow going for the specified duration. Perform ACN wash procedure A twice with 10 mL solvent and fluidizing each wash 4 times, then perform ACN wash procedure B once with 10 mL solvent, then perform ACN wash procedure A once with 40 mL solvent and fluidizing each wash 2 times, then perform ACN wash procedure B once with 10 mL solvent. All wash solvent comes into the reactor through the acid feed zone (FIG. 3). Most of the resin shrinking happens during the first 2 fluidized washes, which mitigates pressure drop issues in the tall bed. Deblocking solution flow rates are slower and total contacting time is longer for the first 6 phosphoramidites, because of resistance to flow and the fact that pressure on the top of the reactor bed is deliberately limited to 20 psig. Liquid flux gradually increases and the total deblocking solution contact time gradually decreases for bases 1 through 7.

ACN Wash Procedure a (Fluidized Wash):

Open waste valve 9, charge ACN into the acid feed zone, then close valve 9 and push it into the reactor with nitrogen pressure for 8 seconds. Fluidize the resin bed the desired number of times as above, pressurizing the reactor with nitrogen for 3 seconds and venting and blowing nitrogen up through the reactor for 10 seconds. Open valve 10 and start waste pump 9 to pump to waste at rate of 30 mL/min for 20 seconds.

ACN Wash Procedure B (Plug Flow Wash, No Fluidization):

Open valve 9 (to waste) and charge ACN into the acid feed zone, then close valve 9 and push it into the reactor with nitrogen pressure for 8 seconds. Open valve 10 and pump with Pump 9 at a rate of 30 mL/min for 20 seconds.

Coupling reaction: After deblocking wash, the next sequential phosphoramidite is coupled, installed in sequential steps from 3' to 5'. For each phosphoramidite to be coupled in the sequence, perform the coupling reaction procedure essentially as described as follows, using the amidite solution (listed in Table 4) corresponding to the phosphoramidite in the sequence. Turn valve 8 to B. Prewash the amidite zone and flow path to the reactor twice, each time by pumping 8 mL ACN into the amidite feed zone with valve 9 closed, then open valve 9 and push with nitrogen pressure to waste for 30 seconds. Pump first the activator solution (3.6 mL, 10 equiv.) and then the appropriate amidite solution from Table 4 (3.6 mL, 2.0 equiv.) into the feed zone. Close valve 9 and 24 and push the mixture in the feed zone into the reactor with nitrogen pressure for 5 seconds.

With the amidite and activator solutions mixed with the resin, repeatedly fluidize the bed as follows with valve 24 open and valve 9 closed: apply nitrogen pressure to the top of the reactor for 3 seconds, then vent pressure out of the top of the reactor and open valve 38 to blow nitrogen up through the reactor for 6 seconds. Allow the resin to cascade down through the liquid for 8 seconds. Repeat this process repeatedly for 10 min, then open valve 9 and apply nitrogen pressure for 30 seconds to the top of the reactor, draining liquid from the bottom of the reactor to waste. Pump ACN (10 mL) into the feed zone and push it through the reactor with nitrogen pressure for 30 seconds, then repeat this ACN wash once more.

Oxidation reaction (when required instead of Sulfurization): After the coupling reaction wash, perform the oxidation reaction essentially as described as follows. Turn valves 6, 7, and 8 to A, and open valve 9. Pump oxidation solution (9 mL, 2.5 equivalents) into the feed zone, close valve 9, and push it into the reactor with nitrogen pressure for 8 seconds. Fluidize the reactor bed five times as follows: pressurize the top of the reactor with nitrogen pressure for 3 seconds, then release the nitrogen pressure by venting and open valve 38 to blow nitrogen up through reactor for 10 seconds. Open valve 10 and pump 9 mL of liquid volume with pump 9 over 60 seconds. Perform ACN wash procedure A (fluidized wash) twice with 10 mL solvent, fluidizing the first wash 4 times and the second wash 2 times. Then, perform ACN wash procedure B (plug flow wash) once with 10 mL solvent, then perform ACN wash procedure A once with 30 mL solvent and fluidizing 3 times, then perform ACN wash procedure B once with 10 mL solvent. All wash solvent comes into the reactor through the oxidation feed zone. Most of the resin shrinking happens during the first 2 fluidized washes which mitigates pressure drop issues in the tall bed.

Sulfurization (thiolation) reaction (when required instead of Oxidation): After the coupling reaction wash, perform the thiolation reaction essentially as described as follows. Turn valve 6 to B, valves 5, 7, and 8 to A, and open valve 9. Pump sulfurization solution (12 mL) into the feed zone, close valve 9, and push it into the reactor with nitrogen pressure for 8 seconds. Fluidize the reactor bed 22 times as follows: pressurize the top of the reactor with nitrogen pressure for 3 seconds, then release the nitrogen pressure by venting and open valve 38 to blow nitrogen up through reactor for 10 seconds. Most of the resin swelling happens during the fluidizations. Total time for the 22 fluidizations is about 8 minutes. Open the valve to waste (valve 10) and pump the sulfurization solution through the resin bed with Pump 9 at a rate of 12 mL per 30 seconds. Perform ACN wash procedure A (fluidized wash) twice with 10 mL solvent, fluidizing the first wash 4 times and the second wash 2 times. Then, perform ACN wash procedure B (plug flow wash) once with 10 mL solvent, then perform ACN wash procedure A once with 30 mL solvent and fluidizing 3 times, then perform ACN wash procedure B once with 10 mL solvent. All wash solvent comes into the reactor through the XH feed zone (FIG. 3). Most of the resin shrinking happens during the first 2 fluidized washes which mitigates pressure drop issues in the tall bed.

Capping reaction: After the oxidation (or sulfurization) reaction wash, perform the capping reaction essentially as described as follows. Turn valves 5 and 6 to B, and valves 7 and 8 to A. Open valve 9. Simultaneously pump capping solution A (6.3 mL) and capping solution B (6.3 mL) into the feed zone and then close valve 9. Push the liquid into the reactor with nitrogen pressure for 8 seconds. Fluidize the reactor bed 3 times as follows: pressurize the top of the reactor with nitrogen pressure for 3 seconds, then release the nitrogen pressure by venting and open valve 38 to blow nitrogen up through reactor for 10 seconds. Most of the resin swelling happens during the fluidizations. Open valve 10 and pump 12.6 mL of liquid volume over 70 seconds. Perform ACN wash procedure A (fluidized wash) twice with 10 mL solvent, fluidizing the first wash 3 times and the second wash 2 times. Then, perform ACN wash procedure B (plug flow wash) once with 10 mL solvent, then perform ACN wash procedure A once with 30 mL solvent and fluidizing 3 times, then perform ACN wash procedure B once with 10 mL solvent. All wash solvent comes into the reactor through the capping feed zone (FIG. 3). Most of the resin shrinking happens during the first 2 fluidized washes which mitigates pressure drop issues in the tall bed.

After the final amidite coupling cycle is complete, repeat the cycle using the phosphorylating solution instead of amidite. After the phosphorylating reagent is coupled and oxidized, repeat the deblocking step. Wash the resin with DEA solution as follows. Charge 9.3 mL DEA solution to the reactor, fluidize 4 times, then pump out the bottom of the reactor at 8 mL/min. Repeat this 9.3 mL DEA wash 3 more times. Then, wash with ACN as follows. Perform ACN wash procedure A (fluidized wash) twice with 10 mL solvent, fluidizing the first wash 4 times and the second wash 2 times. Then, perform ACN wash procedure B (plug flow wash) once with 10 mL solvent, then perform ACN wash procedure A once with 30 mL solvent and fluidizing 2 times, then perform ACN wash procedure B once with 10 mL solvent.

Dry with nitrogen blowing down through the resin bed to give 2.2319 gram of dry resin. This corresponds to 1.4997 gram of weight gain. This corresponds to 8.83 g/mmol weight gain therefore the crude mass yield of the protected oligonucleotide product is 96% by mass gain.

Perform the cleavage and deprotection reaction on a small sample with concentrated $NH_4OH$ solution at 50° C. for 4 hours. UPLC shows the cleaved and deprotected oligonucleotide product is 80.85% pure by peak area percent, as shown in the Table of UPLC results for examples 1 through 5 (Table 13). LCMS analysis confirms that the main product peak represents the correct HPRT div22 AS strand.

Figure 4:
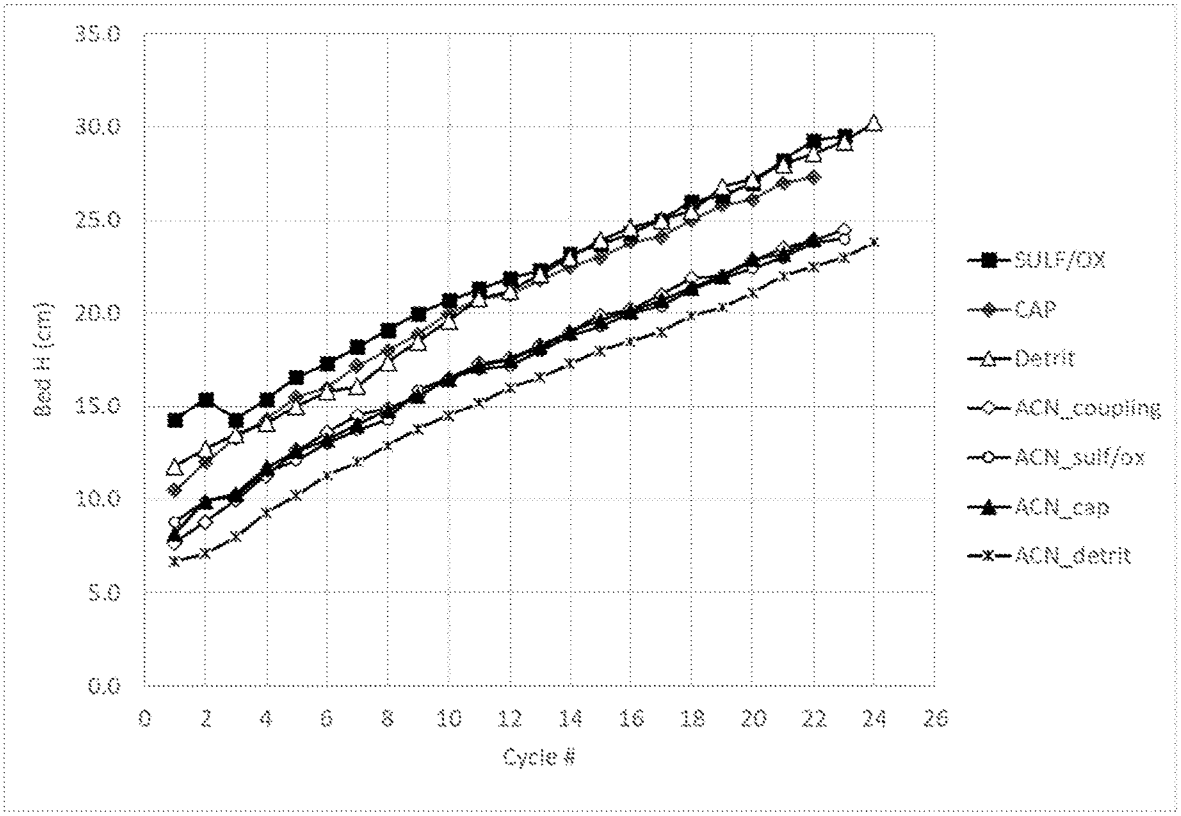
FIG. 4 is a graph depicting the resin bed height in Example 2 at each phosphoramidite cycle.

Resin bed swelling, shrinking, and growing data throughout the 23 mer oligonucleotide build is shown in FIG. 4. Maximum pressure drop across the resin bed was 20 psig during the experiment, because that was the pressure of the supply nitrogen used to push liquid through the resin bed.

The trend labeled "detrit" in FIG. 4 is the resin bed height after the deblock reaction solution had all passed down through the resin bed and drained, before washing.

The trend labeled "ACN_detrit" in FIG. 4 is the bed height after the last ACN solvent wash after deblocking. Likewise, the trend labeled "sulf/ox" is the resin bed height after the sulfurization or oxidation reaction solution had all passed down through the resin bed and drained, before washing, and so on. Resin bed height increased roughly linearly from amidite cycle 1 through cycle 24. Resin bed height was changing by about 5 cm from minimum to maximum within each cycle. For example, the resin beads would swell during the deblocking reaction, causing the packed resin bed height to increase by about 4 cm. Then, the resin beads would shrink during the washing, causing resin bed height to shrink about 5 cm. After coupling, resin beads would swell and bed height would increase by about 4 cm during the oxidation or sulfurization reaction. Then, resin beads with shrink during the subsequent wash, causing resin bed height to decrease about 4 cm, and so on. Given these extreme swelling and shrinking events, happening 3 times each cycle for 24 cycles, it would not be possible to run such a tall bed height with a downflow-only packed bed reactor, because pressure drop would be prohibitive. The reason that pressure drop is mitigated in the fluid bed reactor is because the resin particle swelling and shrinking mostly takes place while the bed is fluidized. Then when the resin bed resettles at each new bed height, the flow resistance through the cake is still low, with maximum pressure drop of only 20 psig. Furthermore, there is no channeling each time the resin bed re-settles after each solvent swap.

Referring to FIG. 3 and considering Example 2, the detailed automation procedure for the sequence of pumps and valve operations is written as follows. The procedure is similar to what is written for Example 1, but the fluidization is done by nitrogen blowing up through the reactor from the bottom. Also, the washes were done differently after each reaction. The first 2 washes were fluidized because it helped with the subsequent liquid flux for the tall resin bed height. Most of the resin swelling with reagent occurred while fluidized at the beginning of the reactions, and most of the resin de-swelling occurred while fluidized with solvent at the beginning of the washes.

Repeat this sequence for each amidite. In this written procedure, the pumping rates and times during deblocking represent cycles 7 through 12. Pumping time was 410 second rather than 330 seconds for cycles 13 to 24 because larger amount of deblocking solution was used after the first 12 cycles. Pumping rates during deblocking started out slower at the beginning because there is more resistance to flow through the resin bed for the first six cycles. Deblocking flow rates gradually increased and times gradually decreased for the first 6 cycles. For example, deblocking plug flow reaction time was 840 seconds and pumping rate was set at 5 mL/min for the first 2 cycles, but by the $7^{th}$ cycle, deblocking plug flow reaction time was 330 seconds and pumping rate was set at 12 mL/min, because the resistance to flow through the bed decreased as the oligo grew longer on the resin.

Deblocking
- valve 8 to A,
- Valve 7 to B,

Pump acid solution into acid feed zone.
- O 9 (this depressurizes reactor through resin bed and makes sure liquid is out the bottom of the reactor during the time that acid is measuring out)
- O 54
- O 14
- Pump acid into acid feed zone (30 mL)
- C 14
- C 54
- C 9

Push acid solution into reactor and fluidize 3 times to react and re-set bed flat with no channels

O 44

Wait "time to push into reactor" (8 seconds)

Run the next 6 rows 3 times.

O 44

Wait "N2 time to push bed down" (5 seconds)

C 44

O 54, O 38

Wait "vent time to fluidize bed with N2 bubbling" (10 seconds)

C 54, C 38

Pump the acid solution through the resin plug flow for the reaction.

O 44

O 10

Start pump P9 at rate of 12 mL/min for 330 seconds.

In parallel to P9 pumping, open 14 and start acid feed at 15 mL/min until pumped 40 mL. Liquid pumping into acid feed zone simultaneously flows into the reactor to maintain liquid level above the resin bed and keep the plug flow going for the 330 seconds.

C 14

C 44

C 10

O 9 and wait for pressure to drop to user setpoint (drop from ~20 psig to 10 psig). Fluidized wash. Run this 2 times, but fluidize 4 times the first time and 2 times the second time.

O 9

O 34

O 54

Pump ACN into feed zone (10 mL)

C 34

C 54

C 9

O 44

Wait "time to push into reactor" (8 seconds)

Run the next 6 rows 4 times in the first wash and 2 times on the second wash.

O 44

Wait "N2 time to push bed down" (5 seconds)

C 44

O 54, O 38

Wait "vent time to fluidize bed with N2 bubbling" (10 seconds)

C 54, C 58

O 44

O 10

Start pump P9 at rate of 20 mL/min for 30 seconds.

C 44

C 10

O 9 and wait for pressure to drop to user setpoint (drop from ~20 psig to 10 psig). Plug flow wash.

O 9

O 34

O 54

Pump ACN into feed zone (10 mL)

C 34

C 54

C 9

O 44

Wait "time to push into reactor" (8 seconds)

Start pump P9 at rate of 30 mL/min for 20 seconds.

C 44

C 10

O 9 and wait for pressure to drop to user setpoint.

Larger fluidized wash to wash up high onto the upper walls of the reactor (note that this was later determined to be unnecessary).

O 9

O 34

O 54

Pump ACN into feed zone (40 mL)

C 34

C 54

C 9

O 44

Wait "time to push into reactor" (8 seconds)

Run the next 6 rows 3 times.

O 44

Wait "N2 time to push bed down" (5 seconds)

C 44

O 54, O 38

Wait "vent time to fluidize bed with N2 bubbling" (10 seconds)

C 54, C 58

O 44

O 10

Start pump P9 at rate of 30 mL/min for 80 seconds.

C 44

C 10

O 9 and wait for pressure to drop to user setpoint (drop from ~20 psig to 10 psig). Plug flow wash.

O 9

O 34

O 54

Pump ACN into feed zone (10 mL)

C 34

C 54

C 9

O 44

Wait "time to push into reactor" (8 seconds)

O 10

Start pump P9 at rate of 30 mL/min for 20 seconds.

C 44

C 10

O 9 and wait for pressure to drop to user setpoint (drop from ~20 psig to 10 psig). Coupling reaction Valve 8 to B Pre-wash amidite zone and flow path to reactor before coupling (run this 2 times)

O 35

O 55

Pump P2, 8 mL ACN into amidite zone.

C 35

C 55

O 9

O 45

Wait time to push down through resin bed in reactor and out to waste (30 seconds)

C 45

Measure out amidite and activator into amidite+activator feed zone.

open valve 110A pump activator specified volume (3.6 mL).

close valve 110A

Open valve 110B

Wait 5 seconds to push activator solution into amidite+ activator feed zone

Close valve 110B open valve 101A. NOTE: Valve 101 was used for mA. Each of the amidites had its own valves and its own feed line into the activation zone (FIG. 3).

pump amidite specified volume (3.6 mL).
close valve 101A
Open valve 101B
Wait 5 seconds to push amidite solution into amidite+activator feed zone
Close valve 101B Push amidite reaction solution into reactor and mix with resin for 10 minutes.
C 55
C 9
C 24
O 45
Wait 5 seconds
O 24
Wait "time to push into reactor" (8 seconds)
Repeat the next 7 rows "fluid bed coupling time" (10 minutes).
O 45
Wait "N2 time to push bed down" (3 seconds)
C 45
O 55, O 38
Wait "vent time to fluidize bed with N2 bubbling" (6 seconds)
C 55
Wait "time between fluidizations during coupling" (8 seconds)
After the "fluid bed coupling time" is over
O 45
O 9
Wait "time to push to waste after fluidizing" (30 seconds)
C 45
Wait until reactor pressure decreases to user setpoint indicating that the coupling solution is all pushed out to waste (10 psig)

Solvent wash with ACN after coupling (run this 2 times)
O 35
O 55
Pump "volume ACN for single pass wash coupling" (10 mL)
C 35
C 55
O 9
O 101B, 102B, 103B, 104B, 105B, 106B, 107B, 108B, 109B, 110B at the same time
Wait "time to push to waste single pass coupling wash" (30 seconds)
C 101B, 102B, 103B, 104B, 105B, 106B, 107B, 108B, 109B, 110B at the same time
C 9

Oxidation (when required instead of Sulfurization)
O 9
Valve 8 to A
Valve 7 to A
Valve 6 to A Pump iodine solution into oxidation feed zone.
O 13
O 53
pump 9 mL iodine feed solution
C 13
C 53
C 9

Push iodine solution into reactor and fluidize 11 times which takes about 4 minutes. This is the batch part of the reaction.
O 43
Wait "time to push into reactor" (8 seconds)
Run the next 6 rows 11 times.
O 43
Wait "N2 time to push bed down" (3 seconds)
C 43
O 53, O 38
Wait "vent time to fluidize bed with N2 bubbling" (10 seconds)
C 53, C 38

Pump the iodine solution through the resin for the plug flow part of reaction.
O 43
O 10
Start pump P9 at rate of 9 mL/min for 60 seconds.
C 43
C 10
O 9 and wait for pressure to drop to user setpoint (from 20 to 10 psig).

Fluidized wash. Run this 2 times, but fluidize 4 times the first time and 2 times the second time.
O 9
O 33
O 53
Pump ACN into 12 feed zone (10 mL)
C 33
C 53
C 9
O 43
Wait "time to push into reactor" (8 seconds)
Run the next 6 rows 4 times during the first fluidized wash and 2 times during the second fluidized wash.
O 43
Wait "N2 time to push bed down" (5 seconds)
C 43
O 53, O 38
Wait "vent time to fluidize bed with N2 bubbling" (10 seconds)
C 53, C 58
O 43
O 10
Start pump P9 at rate of 20 mL/min for 30 seconds.
C 43
C 10
O 9 and wait for pressure to drop to user setpoint (from 20 psig to 10 psig).

Plug flow wash.
O 9
O 33
O 53
Pump ACN into 12 feed zone (10 mL)
C 33
C 53
C 9
O 43
Wait "time to push into reactor" (8 seconds)
O 10
Start pump P9 at rate of 30 mL/min for 20 seconds.
C 43
C 10
O 9 and wait for pressure to drop to user setpoint (drop from 20 to 10 psig).

Larger fluidized wash to wash up high onto the upper walls of the reactor (note that this was later determined to be unnecessary).

O 9
O 33
O 53
Pump ACN into 12 feed zone (30 mL)
C 33
C 53
C 9
O 43
Wait "time to push into reactor" (8 seconds)
Run the next 6 rows 3 times.
O 43
Wait "N2 time to push bed down" (5 seconds)
C 43
O 53, O 38
Wait "vent time to fluidize bed with N2 bubbling" (10 seconds)
C 53, C 58
O 43
O 10
Start pump P9 at rate of 30 mL/min for 60 seconds.
C 43
C 10
O 9 and wait for pressure to drop to user setpoint (from 20 to 10 psig).

Plug flow wash.

O 9
O 33
O 53
Pump ACN into 12 feed zone (10 mL)
C 33
C 53
C 9
O 43
Wait "time to push into reactor" (8 seconds)
O 10
Start pump P9 at rate of 30 mL/min for 20 seconds.
C 43
C 10
O 9 and wait for pressure to drop to user setpoint (10 psig).

Sulfurization (when required instead of oxidation)

O 9
Valve 8 to A
Valve 7 to A
Valve 6 to B
Valve 5 to A

Pump sulfurization solution into XH feed zone.

O 12
O 52
pump sulfurization solution (12 mL)
C 12
C 52
C 9

Push sulfurization solution into reactor and fluidize 22 times.

O 42
Wait "time to push into reactor" (8 seconds)
Run the next 6 rows 22 times. This takes about 8 minutes.
O 42
Wait "N2 time to push bed down" (3 seconds)
C 42
O 52, O 38
Wait "vent time to fluidize bed with N2 bubbling" (10 seconds)
C 52, C 38

Pump the sulfurization solution through the resin for the plug flow part of reaction.

O 42
O 10
Start pump P9 at rate that empties the reactor in about 30 seconds.
C 42
C 10
O 9 and wait for pressure to drop to user setpoint (from 20 to 10 psig).

Fluidized wash. Run this 2 times, but fluidize 4 times the first time and 2 times the second time.

O 9
O 32
O 52
Pump ACN into XH feed zone (10 mL)
C 32
C 52
C 9
O 42
Wait "time to push into reactor" (8 seconds)
Run the next 6 rows 4 times for the first fluidized wash and 2 times for the second fluidized wash.
O 42
Wait "N2 time to push bed down" (5 seconds)
C 42
O 52, O 38
Wait "vent time to fluidize bed with N2 bubbling" (10 seconds)
C 52, C 58
O 42
O 10
Start pump P9 at rate of 30 mL/min for 20 seconds.
C 42
C 10
O 9 and wait for pressure to drop to user setpoint (10 psig).

Plug flow wash.

O 9
O 32
O 52
Pump ACN into XH feed zone (10 mL)
C 32
C 52
C 9
O 42
Wait "time to push into reactor" (8 seconds)
O 10
Start pump P9 at rate of 40 mL/min for 15 seconds.
C 42
C 10
O 9 and wait for pressure to drop to user setpoint (10 psig).

Larger fluidized wash to wash up high onto the upper walls of the reactor (note that this was later determined to be unnecessary).

O 9
O 32
O 52
Pump ACN into feed zone (30 mL)
C 32
C 52
C 9
O 42

Wait "time to push into reactor" (8 seconds)
Run the next 6 rows 3 times.
O 42
Wait "N2 time to push bed down" (5 seconds)
C 42
O 52, O 38
Wait "vent time to fluidize bed with N2 bubbling" (10 seconds)
C 52, C 58
O 42
O 10
Start pump P9 at rate of 40 mL/min for 45 seconds.
C 42
C 10
O 9 and wait for pressure to drop to user setpoint.
Plug flow wash.
O 9
O 32
O 52
Pump ACN into XH feed zone (10 mL)
C 32
C 52
C 9
O 42
Wait "time to push into reactor" (8 seconds)
O 10
Start pump P9 at rate of 40 mL/min for 14 seconds.
C 42
C 10
O 9 and wait for pressure to drop to user setpoint (10 psig).
Capping
Valve 8 to A
Valve 7 to A
Valve 6 to B
Valve 5 to B
Pump capping solutions into capping feed zone.
O 11A
O 11B
O 51
Simultaneously pump capA "volume capA" (6.3 mL) and pump capB "volume capB" (6.3 mL)
C 11A
C 11B
C 51
C 9
Push capping solution into reactor and fluidize 3 times to react and re-set bed flat with no channels
O 41
Wait "time to push into reactor" (8 seconds)
Run the next 6 rows 3 times.
O 41
Wait "N2 time to push bed down" (3 seconds)
C 41
O 51, O 38
Wait "vent time to fluidize bed with N2 bubbling" (10 seconds)
C 51, C 38
Pump the capping solution through the resin for the plug flow part of the reaction.
O 41
O 10
Start pump P9 at a rate that empties the reactor in about 70 seconds.
C 41
C 10
O 9 and wait for pressure to drop to user setpoint.
Fluidized wash. Run this 2 times, but fluidize 3 times the first time and 2 times the second time.
O 9
O 31
O 51
Pump ACN into capping feed zone (10 mL)
C 31
C 51
C 9
O 41
Wait "time to push into reactor" (8 seconds)
Run the next 6 rows 3 times on the first fluidized wash and 2 times on the first fluidized wash.
O 41
Wait "N2 time to push bed down" (5 seconds)
C 41
O 51, O 38
Wait "vent time to fluidize bed with N2 bubbling" (10 seconds)
C 51, C 58
O 41
O 10
Start pump P9 at rate of 30 mL/min for 20 seconds.
C 41
C 10
O 9 and wait for pressure to drop to user setpoint (10 psig).
Plug flow wash.
O 9
O 31
O 51
Pump ACN into capping feed zone (10 mL)
C 31
C 51
C 9
Wait "time to push into reactor" (8 seconds)
O 10
Start pump P9 at rate of 40 mL/min for 15 seconds.
C 41
C 10
O 9 and wait for pressure to drop to user setpoint (10 psig).
Larger fluidized wash to wash up high onto the upper walls of the reactor (note that this was later determined to be unnecessary).
O 9
O 31
O 51
Pump ACN into capping feed zone (30 mL)
C 31
C 51
C 9
O 41
Wait "time to push into reactor" (8 seconds)
Run the next 6 rows 3 times.
O 41
Wait "N2 time to push bed down" (5 seconds)
C 41
O 51, O 38
Wait "vent time to fluidize bed with N2 bubbling" (10 seconds)
C 51, C 58
O 41
O 10
Start pump P9 at rate of 40 mL/min for 45 seconds.
C 41
C 10
O 9 and wait for pressure to drop to user setpoint (10 psig).

Plug flow wash.

O 9

O 31

O 51

Pump ACN into capping feed zone (10 mL)

C 31

C 51

C 9

O 41

Wait "time to push into reactor" (8 seconds)

O 10

Start pump P9 at rate of 40 mL/min for 15 seconds.

C 41

C 10

O 9 and wait for pressure to drop to user setpoint.

Example 3—Preparation of HPRT Div22 Antisense Strand

The same HPRT Div22 Antisense strand is prepared as in Examples 1 and 2. The synthesis of this molecule using the fluidized bed method of the current invention is herein described, and comprises deblocking, coupling, oxidizing (or sulfurization), and capping steps to sequentially install the remaining phosphoramidites. The main differences are as follows. Example 3 is done at larger scale (1 mmol) and in a larger fluid bed reactor that is the same diameter from bottom to top, 2.2 cm inside diameter and 1 m tall. In this larger diameter reactor, the fluidization is sufficient without the wider funnel zone at the top. The larger the reactor diameter, the less the wall effects, so the easier it is to completely fluidize and redistribute solids and liquid without an upper wide diameter section. The fluidization at the start of each reaction step typically reached about 0.3 m height in the reactor. Also, in example 3, each of the reactions besides coupling (deblocking, oxidizing, sulfurization, and capping) are done by charging a first portion of the reagent into the reaction, fluidizing the first portion for a target amount of time, then pumping the first portion through the resin bed plug flow style while simultaneously charging the second portion of the reagents to the top of the reactor so that all reagents pump through plug flow style. Like in Examples 1 and 2, a large excess of wash solvent and DCA reagent solution were used in Example 3. See Example 7 for an example with reduced DCA reagent and see Examples 6, 8, and 9 for examples of reduced ACN washing. Table 31 is a guide to the various embodiments in the fluid bed reactor examples.

Resin bed height reached 9 cm at the end of ACN solvent washes after draining, and 7 cm dry by the end of the experiment. Maximum resin bed height of 11 cm was reached at the end of the final deblocking and oxidation steps after draining. Maximum pressure drop through the resin bed was 20 psig at any time during the experiment, because that is the pressure of the supply nitrogen used to push liquid through the resin bed. Two equivalents of amidite were used for the couplings, like in Example 2. Overall synthesis conditions are given in Table 6.

TABLE 6

Example 3 synthesis conditions

| Item | Value | Unit |
|---|---|---|
| Resin loading | 299 | μmol/gram |
| Resin starting amount | 3.344 | gram |
| Synthesis scale | 1 | mmol |
| Deblocking solution, amount per cycle | 528 | mL |
| Deblocking reaction time | 7 | Min |
| Amidite concentration | 0.1 | M in ACN |
| Amidite equivalence | 2 | Eq |
| Activator concentration | 0.5 | M in ACN |
| Activator equivalence | 10 | Eq |
| Amidite solution, amount per cycle | 20 | mL |
| Activator solution, amount per cycle | 20 | mL |
| Coupling reaction time | 10 | Min |
| Iodine equivalence | 3 | Eq |
| Oxidation solution, amount per cycle | 60 | mL |
| Iodine solution concentration | 0.05 | M |
| Oxidization time | 2.8 | min |
| Sulfurization equivalence | 3 | eq |
| Sulfurization solution, amount per cycle | 150 | mL |
| Xanthane Hydride concentration | 0.02 | M |
| Sulfurization time | 3 | min |
| Capping solution A, amount per cycle | 70 | mL |
| Capping solution B, amount per cycle | 70 | mL |
| Capping time | 3 | min |

Begin with mU coupled onto NittoPhase HL 2' OMeU(bz) 300 resin (299 μmol/g) using known methods (herein referred to as "mU-resin"), and refer to FIG. 5 for the setup of the synthesizer apparatus. Place 3.344 g (1.00 mmol) of the mU-resin into a 2.2 cm inside diameter reactor with filter frit at the bottom. The initial dry resin depth is about 3 cm tall.

Prepare the reagent and amidite solutions the same as described in Example 1 and Example 2. Prime all pumps and feed lines. ACN was passed over a bed of molecular sieves on the way into an inerted feed can. All feeds use peristaltic pumps and feed vessels. The amidite solutions are contained separately in feed vessels labeled "AM. 1 L" and connected to peristaltic pumps attached to valves V1A through V8A in FIG. 5. The phosphorylating reagent is contained in a feed vessel labeled "AM. 1 L" and connected to a peristaltic pump attached to valve V9A in FIG. 5. The activator and DEA solutions are contained in feed vessels labeled "Activ. 5 gal" and "DEA," respectively in FIG. 5. As in FIG. 3, acetonitrile is abbreviated as "ACN" in FIG. 5.

For each phosphoramidite added in the synthesis, perform the deblocking, coupling, oxidizing (or sulfurization where there is a P=S linkage in the sequence), and capping steps sequentially as described below.

At each step, resin bed fluidization is performed at two different times: first when the reagent mixture is charged to the reactor and the resin is exposed to it, and second when some of the wash solvent steps are charged to the reactor. However, during the coupling reaction the fluidization continued repeatedly for the entire 10-minute coupling time. As in Example 2, the fluidization is done by blowing nitrogen gas up through the bottom filter screen by opening valves 58, 54, and 53 (V58, V54, V53 in FIG. 5) the same time the vent valve V52 opens. When this procedure states that liquid is pumped down through the resin bed, it means that the waste pump at the outlet of the reactor bottom runs at a target setpoint, while nitrogen pressure pushes on top of the resin bed to push the liquid down through. The purpose of the peristaltic pump is to meter the liquid flow through the bed at a controlled rate.

Deblocking reaction: Charge deblocking solution (100 mL) into the feed zone. Chase the deblocking solution into the feed zone with nitrogen to clear the feed tubing. Push the deblocking solution into the reactor. Fluidize the resin bed twice to achieve complete liquid-solid contacting and re-set the resin bed. Total time for both fluidizations is about 1 minute. Start pumping the deblocking solution down through the resin bed at a pump setpoint of 110 mL/min for 315 seconds. Pump more deblocking solution (428 mL) into the reactor simultaneously, so that it enters the top of the reactor at about the same rate that it is pumping out. A total of 528 mL pumps through the resin bed during the 315 seconds. Chase the deblocking solution into the reactor with nitrogen to clear the feed tubing. Push the residual deblocking solution to waste out the filter bottom.

Wash #1 (do this step 2 times): Charge ACN solvent into reactor through the acid feed line (50 mL). Chase wash solvent into reactor with nitrogen to clear the feed tubing. Push solvent through resin bed and to waste.

Wash #2: Charge ACN solvent into reactor through solvent feed line (90 mL).

Chase wash solvent into reactor with nitrogen to clear the feed tubing. Push with nitrogen down through the reactor and into the bottom of the fluidization push zone (between V54 and V57). Fluidize the resin bed to achieve complete liquid-solid contacting and re-set the resin bed two times. Start pumping the ACN solvent through the resin bed at a pump setpoint of 100 mL/min for 120 seconds. Pump more ACN solvent (110 mL) into reactor simultaneously, so that it enters the top of the reactor at about the same rate that it is pumping out. A total of 200 mL pumps through the resin bed. Push residual ACN solvent to waste out the filter bottom.

Wash #3 (do this step 2 times): Charge ACN solvent into reactor through solvent feed line (40 mL). Chase wash solvent into reactor with nitrogen to clear the feed tubing. Push solvent through resin bed and out reactor to waste via valve 57, in order to clean out the fluidization push zone between valves 54 and 57 and the waste tubing.

Coupling reaction: Each of the six amidites has its own individual pump, valves and its own feed line into the activation zone as shown in FIG. 5 (activation zone 10 labeled "2 L"), to minimize chance of cross-contamination. This build only uses 6 amidites, but there are 9 amidites in total (mA, mC, mG, mU, fA, fC, fG, fU, and phos) and 10 ports on the amidite zone (including the activator).

Prewash (do this step 2 times): Charge ACN solvent into amidite activation zone (80 mL) and push it down through the reactor to waste, also washing out the fluidization push zone between valves 54 and 57.

Reaction: Pump the specified amidite (20 mL) into the amidite activation zone and chase it in with nitrogen. Pump the activator solution (20 mL) into the amidite activation zone and chase in with nitrogen. Push this mixture into the feed zone, and then into the reactor to start the coupling reaction on the resin. Fluidize the resin reactor once every 30 seconds to mix contents for the duration of the 10-minute coupling time. (In other words, fluidize for 15 seconds every 30 seconds) Push the coupling solution to waste out the filter bottom after the reaction time.

Wash #1 (do this step 2 times): Charge ACN solvent into the amidite activation zone (100 mL), then push it down through the reactor to waste, also washing out the fluidization push zone between valves 54 and 57.

Wash #2 (do this step 2 times): Charge ACN (40 mL) into the reactor through the solvent feed line. Chase the wash solvent into the reactor with nitrogen to clear the feed tubing. Push the solvent through the resin bed and out of the reactor to waste, and at the same time use the solvent to clean out the fluidization push zone (between V54 and V57) and the waste pump tubing.

Oxidation reaction (when required instead of Sulfurization): Charge ACN (100 mL) into the amidite activator mixing zone so that it is ready to wash the resin immediately at the end of the oxidation reaction. Charge oxidation solution (59 mL) into the feed zone, chasing it with nitrogen to clear the feed tubing. Push the solution into the reactor and fluidize the resin bed twice to achieve complete liquid-solid contacting and re-set the resin bed. Total time for both fluidizations is about 1.2 minutes. Start pumping the oxidation solution through the resin bed at a pump setpoint of 130 mL/min for 30 seconds. Pump more iodine solution (1 mL) into the reactor simultaneously, so that it enters the top of the reactor at about the same rate that it is pumping out. Chase the iodine solution into the reactor with nitrogen to clear the feed tubing. A total of 60 mL of oxidation solution pumps through the resin bed during the 30 seconds. Push the residual oxidation solution to waste out of the filter bottom. Push the 100 mL ACN wash solvent (from the amidite activator mixing zone) through the reactor to wash the resin.

Wash #1 (do this step 2 times): Charge ACN (50 mL) into reactor through the oxidation solution feed line, chasing it with nitrogen to clear the feed tubing. Push the solvent through resin bed and to waste.

Wash #2: Charge ACN (40 mL) solvent into the feed zone through the solvent feed line. Chase the wash solvent into the reactor with nitrogen to clear the feed tubing. Push the solvent through the resin bed and out of the reactor to waste, and at the same time use the solvent to clean out the fluidization push zone (between V54 and V57) and the waste pump tubing.

Wash #3: Charge ACN (90 mL) into the feed zone through the solvent feed line. Chase the wash solvent into the reactor with nitrogen to clear the feed tubing. Push the solvent down through the reactor and into the bottom of the fluidization push zone (between V54 and V57). Fluidize the resin bed to achieve complete liquid-solid contacting and re-set the resin bed 2 times. Start pumping the ACN solvent through the resin bed at a pump setpoint of 100 mL/min for 130 seconds. Pump more ACN (110 mL) into the reactor simultaneously, so that it enters the top of the reactor at about the same rate that it is pumping out. A total of 200 mL pumps through the resin bed. Push residual ACN solvent to waste out of the filter bottom.

Wash #4 (do this step 2 times): Charge ACN (40 mL) into the feed zone through the solvent feed line. Chase the wash solvent into the feed zone with nitrogen to clear the feed tubing. Push the solvent through the resin bed and out of the reactor to waste, and at the same time use the solvent to clean out the fluidization push zone (between V54 and V57) and the waste pump tubing.

Sulfurization (thiolation) reaction (when required instead of Oxidation): Charge xanthane hydride solution (90 mL) into the feed zone and into the reactor. Chase the solution into the reactor with nitrogen to clear the feed tubing. Fluidize the resin bed two times to achieve complete liquid-solid contacting and re-set the resin bed. Total time for both fluidizations is about 1 minute. Start pumping the xanthane hydride solution through the resin bed at a pump setpoint of 130 mL/min for 80 seconds. Pump more xanthane hydride solution (60 mL) into the reactor simultaneously, so that it enters the top of the reactor at about the same rate that it is pumping out. Chase the xanthane hydride solution into the reactor with nitrogen to clear the feed tubing. A total of 150 mL pumps through the resin bed during the 80 seconds. Push the residual xanthane hydride solution to waste out of the filter bottom.

Wash #1 (do this step 2 times): Charge ACN (50 mL) into the reactor through the xanthane hydride solution feed line. Chase the wash solvent into the reactor with nitrogen to clear the feed tubing. Push the solvent through the resin bed and to waste.

Wash #2: Charge ACN (40 mL) into the reactor through the solvent feed line. Chase the wash solvent into the reactor with nitrogen to clear the feed tubing. Push the solvent through the resin bed and out of the reactor to waste, and at the same time use the solvent to clean out the fluidization push zone (between V54 and V57) and the waste pump tubing.

Wash #3: Charge ACN (90 mL) into reactor through the solvent feed line, chasing with nitrogen to clear the feed tubing. Push the solvent down through the reactor and into the bottom of the fluidization push zone (between V54 and V57). Fluidize the resin bed to achieve complete liquid-solid contacting and re-set the resin bed 2 times. Start pumping the ACN solvent through the resin bed at a pump setpoint of 100 mL/min for 130 seconds. Pump more ACN (110 mL) into the reactor simultaneously, so that it enters the top of the reactor at about the same rate that it is pumping out. A total of 200 mL of ACN pumps through the resin bed. Push the residual solvent to waste out of the filter bottom.

Wash #4 (do this step 2 times): Charge ACN (40 mL) into the reactor through the solvent feed line. Chase the wash solvent into the reactor with nitrogen to clear the feed tubing. Push the solvent through the resin bed and out of the reactor to waste, and at the same time use the solvent to clean out the fluidization push zone (between V54 and V57) and the waste pump tubing.

Capping reaction: Charge capping solution A and capping solution B solutions into the reactor (45 mL each), chasing each solution into the reactor with nitrogen to clear the feed tubing. Fluidize the resin bed two times to achieve complete liquid-solid contacting and re-set the resin bed. Total time for both fluidizations is about 1 minute. Start pumping the capping solution A and capping solution B mixture through the resin bed at a pump setpoint of 130 mL/min for 70 seconds. Pump more capping solution A and capping solution B (25 mL each) into the reactor simultaneously, so that it enters the top of the reactor at about the same rate that it is pumping out. Chase capping solution A and capping solution B into the reactor with nitrogen to clear the feed tubing. A total of 140 mL pumps through the resin bed during the 70 seconds. Push residual capping solution A and capping solution B to waste out of the filter bottom.

Wash #1 (do this step 2 times): Charge ACN into the reactor through the capping solution A and capping solution B feed lines (50 mL each), chasing with nitrogen into the reactor to clear the feed tubing. Push the solvent through resin bed and to waste.

Wash #2 (do this step 2 times): Charge ACN (40 mL) into the reactor through the solvent feed line. Chase the wash solvent into the reactor with nitrogen to clear the feed tubing. Push the solvent through the resin bed and out of the reactor to waste, and at the same time use the solvent to clean out the fluidization push zone (between V54 and V57) and the waste pump tubing.

After the final coupling cycle is complete, repeat the cycle using the phosphorylating solution instead of amidite. After the phosphorylating reagent is coupled and oxidized, repeat the deblocking step. React the resin with 500 mL DEA solution for 10 minutes. Wash with ACN and dry with nitrogen blowing down through the resin bed for 30 minutes to give 11.96 g of dried product on resin. 20 mg of product+resin is pulled for a sample, and 3.344 g of resin is used initially, leaving 8.636 g (94% crude mass yield) of protected oligonucleotide product.

Perform the cleavage and deprotection reaction with concentrated $NH_4OH$ solution at 50° C. for 4 hours for a small sample. UPLC shows the cleaved and deprotected oligonucleotide product is 77.8% pure by peak area percent, as shown in the Table of UPLC results for examples 1 through 5 (Table 13). LCMS analysis confirms that the main product peak represents the correct HPRT div22 AS strand.

Example 4—Preparation of HPRT Div22 Antisense Strand

The same HPRT Div22 Antisense strand was made in this example, like in examples 1, 2, and 3. Like examples 1, 2, and 3, the synthesis of this molecule using the fluidized bed method of the current invention is herein described, and comprises deblocking, coupling, oxidizing (or sulfurization), and capping steps to sequentially install the remaining phosphoramidites. This experiment used the same reactor and procedure as Example 2. The main differences were that the scale was smaller (0.1 mmol scale versus 0.18 mmol scale), resin loading was higher (299 umol/g versus 246 umol/g), therefore the resin bed was not as tall, and the timing of the deblocking and washing after deblocking was less for the shorter resin bed in example 4. The experiment used 0.3346 g Nittophase HL 2'OMeU300 resin lot E05005, loading 299 umol/g. mU17, fA18 and fU22 couplings used 2.5 equivalents amidite (cycles 17, 18, and 21) and 12.5 equivalents activator, but the rest of the amidite coupling steps all used 2.0 equivalents amidite and 10 equivalents activator, like Example 2. Like in Examples 1, 2, and 3, a large excess of wash solvent and DCA reagent solution were used in Example 4. See Example 7 for an example with reduced DCA reagent and see Examples 6, 8, and 9 for examples of reduced ACN washing. Table 31 is a guide to the various embodiments in the fluid bed reactor examples.

Use the reagent solutions as described in Table 7.

TABLE 7

Reagent solutions for example 4.

| Solution Name | Contents | Lot | Vendor |
|---|---|---|---|
| Main solvent | ACN | 205641 | Fisher |
| Deblocking | 3 vol % Dichloroacetic acid (DCA) in toluene | DZ124-US, DZ944-US | Honeywell |
| Activator | 0.5M 5-(Ethylthio)-1H-tetrazole in ACN | DW336-US | Honeywell |
| Capping solution A | 1-Methylimidazole/ACN (20/80 v/v) | DZ847 | Honeywell |
| Capping solution B | 1:1 Mixture B1 and B2 | | |
| Capping solution B1 | 40 vol % acetic anhydride in ACN | DX994US | Honeywell |
| Capping solution B2 | 60 vol % 2,6-lutidine in ACN | DY020US | Honeywell |

TABLE 7-continued

Reagent solutions for example 4.

| Solution Name | Contents | Lot | Vendor |
|---|---|---|---|
| DEA | 20% diethylamine in ACN (20/80 v/v) | STBJ15069 | Honeywell |
| Oxidization | 0.05M Iodine in pyridine/ water (90/10 v/v) | DZ225-US | Honeywell |
| Sulfurization | 0.2M Xanthane hydride in ACN/pyridine (70/30 v/v) | | |
| Phosphorylation | 0.1M 2-[2-(4, 4'-Dimethoxytrityloxy) ethylsulfonyl]ethyl-(2-cyanoethyl)-(N, N-diisopropyl)-phosphoramidite in ACN | | Honeywell |

Prepare the 0.1 M amidite solutions shown below in Table 8. Weigh amidite solids into a bottle and insert a drypad, then add ACN to achieve a concentration of 0.1 M. Synthesis conditions for example 4 are listed in Table 9. Synthesis procedure was the same as written in Example 2, also referring to FIG. 3.

TABLE 8

Amidite solution makeup for example 4.

| Amidite solution name | Amidite used | Vendor | Lot | mass (g) | ACN (g) |
|---|---|---|---|---|---|
| 2'-O-Me-A | DMT-2'-O-Me-A(bz) Amidite | ThermoFisher | VB2462 | 4.44 | 39.23 |
| 21-O-Me-C | DMT-21-O-Me-C(Ac) Amidite | ThermoFisher | VD1432 | 2.4 | 23.73 |
| 2'-O-Me-G | DMT-2'-O-Me-G(iBu) Amidite | ThermoFisher | VB2272 | 2.62 | 23.82 |
| 21-O-Me-U | DMT-2'-O-Me-U Amidite | ThermoFisher | VB2282 | 2.27 | 23.67 |
| 2'-F-dA | DMT-21-F-dA (Bz) Amidite | ThermoFisher | VB2242 | 2.2 | 19.58 |
| 2'-F-dU | DMT-2'-F-dU Amidite | ThermoFisher | VB2262 | 1.87 | 19.68 |
| Phos | | Hongene | LPR22B1A1 | N/A | N/A |

TABLE 9

Example 4 synthesis conditions.

| Item | Value |
|---|---|
| Resin loading | 299 μmol/g |
| Resin starting amount | 0.3346 g |
| Synthesis scale | 100 μmol |
| Deblocking solution, amount per cycle | 36 mL for cycles 1-12, 45 mL for cycles 13-24 |
| Deblocking contact time | 9 to 10 min |
| Amidite concentration | 0.1M in ACN |
| Amidite equivalence | 2 eq most cycles, but 2.5 eq cycles 17, 18, and 21 |
| Amidite solution, amount per cycle | 2 mL most cycles, but 2.5 mL cycles 17, 18, and 21 |
| Activator concentration | 0.5M in ACN |
| Activator equivalence | 10 eq most cycles, but 12.5 eq cycles 17, 18, and 21 |
| Activator solution, amount per cycle | 2 mL most cycles, but 2.5 mL cycles 17,18, and 21 |
| Oxidization equivalence | 2.2 eq for cycles 3 and 4, 2.4 eq cycles 5-20, 23 |
| Oxidization time | 6 min |
| Sulfurization equivalence | 13 eq |
| Sulfurization time | 8 min |

TABLE 9-continued

Example 4 synthesis conditions.

| Item | Value |
|---|---|
| Capping solution A, amount per cycle | 3.5 mL |
| Capping solution B, amount per cycle | 3.5 mL |
| Capping time | 4 min |

Resin bed height during downflow portion on the final deblock step was 12.7 cm, therefore resin bed height was less than half compared to Example 2. Maximum pressure drop across the resin bed is 15 psig during the experiment, because that is the pressure of the supply nitrogen used to push liquid through the resin bed. Resin bed height from 10 beginning to end of the synthesis is shown in Table 10.

TABLE 10

Resin bed height from beginning to end of the synthesis for Example 4.

| cycle | amidite | Resin bed height ACN wet at the start of the cycle (cm) | Resin bed height Toluene wet after deblocking (cm) |
|---|---|---|---|
| 1 | mA* | 3.4 | 5.5 |
| 2 | mA* | ND | 6.8 |
| 3 | mG | 4.1 | 7.2 |
| 4 | mG | 4.7 | 7.4 |
| 5 | mA | 5.1 | 7.7 |
| 6 | mU | 5.5 | 8.2 |
| 7 | fA | 5.8 | 8.5 |
| 8 | mC | 6.1 | 8.9 |
| 9 | fU | 6.4 | 9.3 |
| 10 | mG | 6.8 | 9.5 |
| 11 | mA | 7.2 | 9.6 |
| 12 | mC | 7.2 | 9.5 |
| 13 | mA | 7.4 | 9.8 |
| 14 | mU | 7.6 | 10.1 |
| 15 | mC | 7.9 | 10.4 |
| 16 | mU | 8.2 | 10.6 |
| 17 | fA | 8.5 | 10.8 |
| 18 | mA | 8.8 | 11.2 |
| 19 | mA | 9.1 | 11.5 |
| 20 | mA | 9.4 | 11.8 |
| 21 | fU* | 9.7 | 12.1 |
| 22 | mA* | 9.9 | 12.2 |
| 23 | Phos | 10.1 | 12.4 |
| 24 | Final deblock | 10.3 | 12.7 |

After final DEA treatment, wash with ACN and dry with nitrogen blowing down through the resin bed to give 1.1458 gram of dry resin. This corresponds to 0.811 gram of weight gain, but it does not include the correction for sample mass, which was about 6% o of the total material. Crude mass gain was 8.60 g/mmol, which is about 93% o crude mass yield.

Perform the cleavage and deprotection reaction for a 21.9 mg sample with 0.5 mL concentrated $NH_4OH$ solution at 55° C. for 4 hours. UPLC shows the cleaved and deprotected oligonucleotide product is 84.500 pure by peak area percent, as shown in the Table of UPLC results for examples 1 through 5 (Table 13). LCMS analysis confirms that the main product peak represents the correct HPRT div22 AS strand.

Example 5—Comparability to Cytiva ÄKTA Oligonucleotide Synthesizer

The same HPRT Div22 Antisense strand from Examples 1-4 is also prepared in the Cytiva ÄKTA automated oligonucleotide synthesizer starting with NittoPhase HL 2' OMeU 250 resin (246 μmol/g, 0.603 g, 148.4 μmol), performing the same deblocking, coupling, oxidizing (or sulfurization where there is a P=S linkage in the sequence), and capping steps sequentially. Synthesis conditions for example 5 are listed in Table 11.

TABLE 11

Synthesis conditions for example 5.

| experiment | |
|---|---|
| synthesizer | Cytiva AKTA OP100 |
| resin lot | G07010 |
| Resin loading, umol/g | 246 |
| Resin starting amount, g | 0.603 |
| Synthesis scale, umol | 148.4 |
| Reactor volume, mL | 6.3 |
| Reactor diameter, cm | 2 |
| Reactor height, cm | 2 |
| ACN push after coupling, oxidation, thiolation, capping | 2CV |
| Deblocking | 10 vol % Dichloroacetic acid (DCA) in toluene |
| Deblocking solution, amount per cycle, mL | (31~58), 50 in average |
| Deblocking linear velocity, cm/h | 300 |
| ACN volume for deblock wash, mL | 37.8 |
| Amidite concentration, M in ACN | 0.1 |
| Amidite equivalence, eq | 2 |
| Activator reagent | 0.5M 5-(Ethylthio)-1H-tetrazole in ACN |
| Activator equivalence, eq | 10 |
| Coupling time, min | 10 |
| ACN volume for coupling wash, mL | 25.2 |
| Oxidization reagent | 0.05M Iodine in pyridine/water (90/10 v/v) |
| Oxidization equivalence, eq | 3 |
| Oxidization contact time, min | 2.5 |
| ACN volume for oxidization wash, mL | 25.2 |
| Sulfurization reagent | 0.2M Xanthane hydride in ACN/pyridine (70/30 v/v) |
| Sulfurization equivalence, eq | 13 |
| Sulfurization contact time, min | 6 |
| ACN volume for sulfurization wash, mL | 12.6 |
| Capping solution A | 1-Methylimidazole/ACN (20/80 v/v) |
| Capping solution B | 1:1 Mixture B1 and B2 |
| Capping solution B1 | 40 vol % acetic anhydride in ACN |
| Capping solution B2 | 60 vol % 2,6-lutidine in ACN |
| Capping solution A, amount per cycle mL | 6.3 |
| Capping solution B, amount per cycle, mL | 6.3 |
| Capping contact time, min | 1 |
| ACN volume for capping wash, mL | 18.9 |
| DEA | 20% diethylamine in ACN (20/80 v/v) |

TABLE 11-continued

Synthesis conditions for example 5.

| experiment | |
|---|---|
| DEA contact time, min | 10 |
| DEA volume, mL | 40 |
| ACN volume for DEA wash (final wash), mL | 50.4 |

Upon completion of the synthesis and drying the resin, the mass gain was measured to be 8.64 g/mmol, which is 94% crude mass gain. Crude yield was also measured to be 169 OD/umol. Upon cleavage and deprotection, the oligonucleotide product is 80.28% pure by UPLC. LCMS analysis confirms that the main product peak represents the correct HPRT div22 AS strand. The crude yield and purity of the oligonucleotide product is comparable to the product obtained in Examples 1-4, as shown in Table 13. However, in the Cytiva AKTA system, the resin bed is static, and all reagents and solvents pass through the resin bed in a "plug-flow" fashion. The limitation of this system is such that the resin bed height cannot exceed 10 cm without negative effects, such as an increasing pressure drop across the resin bed and channel formation within the resin bed. Resin bed height was 2 cm maximum in Example 5. In contrast, the present invention can have higher resin bed heights (maximum bed height during the experiment described in Example 2 was 30 cm during the downward pushing part of the reactions), increasing batch size capacity for a given reactor diameter, and facilitating flexible batch size for a given reactor.

A summary of Ion-Pairing UPLC method conditions for purity analysis of HPRT div22 Anti-Sense strand is shown in Table 12.

TABLE 12

Summary of Ion-Pairing UPLC method conditions for purity analysis of HPRT div22 Anti-Sense strand

| | |
|---|---|
| Instrument: | Waters I-Class AcquityUPLC with binary pump |
| Column: | 50 × 2.1 mm Waters BEH C18, 1.7 mm, 130 A (pn186003949) |
| Column Temp.: | 55 C |
| Mobile Phase A: | 10 mM DIPEA, 100 mM HFIP in water |
| Mobile Phase B: | ACN |
| Gradient | Initial conditions: 99% A/1% B<br>Increase 1% to 24.3% B in 25 min<br>Increase 24.3-100% B in 0.1 min<br>Hold 100% B for 1.9 min<br>Decrease 100% to 1% B in 0.1 min<br>Hold 1% B for 2.9 min<br>Total run time 30 min |
| Flow Rate: | 0.6 mL/min |
| Wavelength: | 260 nm |

TABLE 13

Comparison of purity, yield, and impurity profiles between syntheses from fluid bed synthesizers Examples 1-4 and from AKTA OP100 synthesizer.

a.

| HPRT antisense strand synthesis example | Example 1, FBR 31 umol, no N2 bubbling | Example 2, FBR 180 umol, 30 cm bed height | Example 3, FBR 1 mmol | Example 4, FBR 100 umol | Example 5, AKTA compare to examples 1-4 |
|---|---|---|---|---|---|
| scale (umol) | 31.1 | 180.1 | 1000 | 100 | 148.4 |
| resin lot | EO5005 | G07010 | EO5005 | EO5005 | G07010 |
| resin loading (umol/g) | 299 | 246 | 299 | 299 | 246 |
| synthesizer | FIG. 3 | FIG. 3 | FIG. 5 | FIG. 3 | Cytiva AKTA OP100 |
| resin bed height final deblock, cm | 2 | 30 | 11 | 13 | 2 |
| reactor i.d. (cm) | 1 | 0.635 | 2.2 | 0.635 | 2 |
| crude mass gain g/mmol | 8.88 | 8.833 | 8.636 | 8.6 | 8.64 |
| OD/umol | 181 | nd | nd | nd | 169 |

b.

| | HPRT antisense strand synthesis example | Example 1, FBR 31 umol, no N2 bubbling | Example 2, FBR 180 umol, 30 cm bed height | Example 3, FBR 1 mmol | Example 4, FBR 100 umol | Example 5 AKTA compare to examples 1-4 |
|---|---|---|---|---|---|---|
| RRT | ID | area % | area % | area % | area % | area % |
| 0.521 | 7mer | | | | | 0.32 |
| 0.640 | 9mer | | | | | 0.38 |
| 0.719 | 11mer | 0.29 | | 0.44 | | |
| 0.768 | 12mer | 0.2 | | 0.34 | | 0.2 |
| 0.785 | 13mer | | | 0.25 | | 0.25 |
| 0.828 | 14mer | 0.21 | | 0.31 | | 0.24 |
| 0.845 | 15mer | 0.23 | 0.21 | 0.33 | | 0.39 |
| 0.861 | 16mer | 0.29 | 0.24 | 0.33 | | 0.44 |
| 0.881 | 17mer | 0.65 | 0.31 | 0.49 | 0.3 | |
| 0.909 | 18mer | 0.27 | 0.28 | 0.71 | 0.29 | 0.43 |
| 0.934 | 19mer | 0.35 | 0.43 | 0.52 | 0.33 | 0.48 |
| 0.950 | 20mer | 0.39 | 0.53 | 0.68 | 0.45 | 0.56 |
| 0.965 | 21mer | 0.8 | 0.82 | 1.83 | 0.61 | 1.2 |
| 0.977 | 22mer | 0.39 | 0.48 | 0.58 | 0.51 | 0.53 |
| 0.984 | 22mer with phos | 0.35 | 0.69 | 0.24 | 0.37 | 0.24 |
| 0.991 | P = S -> P = O | | 2.05 | | | |
| 0.994 | P = S -> P = O | 7.45 | 4.45 | 6.74 | 5.8 | 4.99 |
| 1.000 | HPRT Anti-sense | 81.85 | 80.85 | 77.81 | 84.45 | 80.28 |
| 1.009 | FLP + mA | | 1.79 | | | 2.47 |
| 1.014 | | | 0.44 | | 0.75 | 0.81 |
| 1.016 | | 0.4 | 0.46 | | | |
| 1.021 | | 0.33 | 0.21 | | | 0.44 |
| 1.025 | FLP + mG | | 0.47 | 0.87 | 0.5 | |
| 1.030 | FLP + mA | | 0.2 | 0.34 | | |
| 1.041 | | 0.34 | 0.46 | 0.63 | 0.28 | |
| 1.048 | | | 0.21 | 0.36 | 0.23 | |
| 1.057 | | | 0.21 | 0.26 | | |
| 1.085 | | | | 0.25 | | |
| 1.097 | | | | 0.38 | | |
| 1.107 | | | | 0.27 | | |
| 1.112 | | | | 0.42 | | |
| 1.117 | | 0.26 | 0.21 | 0.39 | | |
| 1.124 | | 0.22 | | 0.42 | | |
| 1.130 | | 0.43 | 0.23 | 0.34 | 0.26 | 0.24 |
| 1.230 | | 0.26 | | | | |
| 1.251 | | 0.21 | | | | |
| 1.259 | | 0.29 | | | | |

Figure 10:
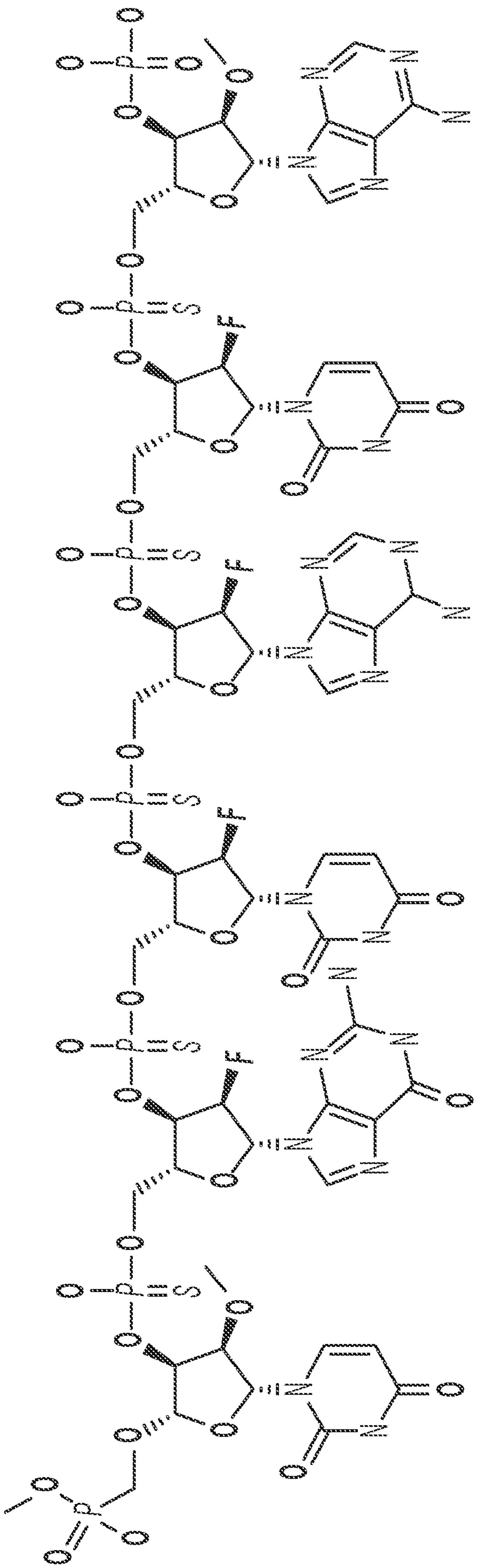
FIG. 10 is a schematic view of a molecule that may be made using the techniques outlined herein.
Figure 10:
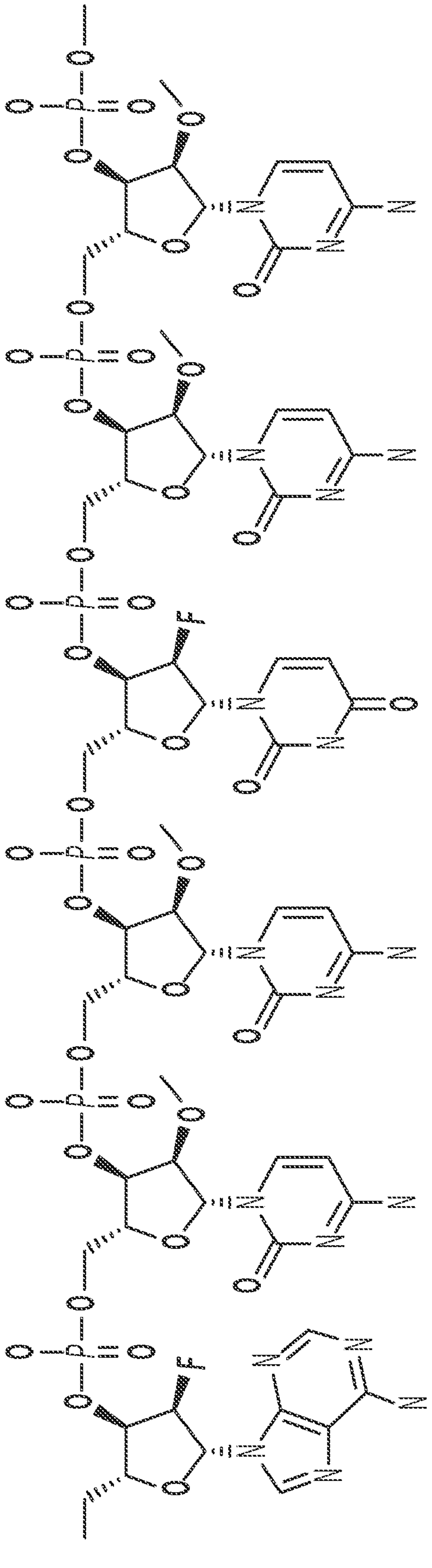
Figure 10:
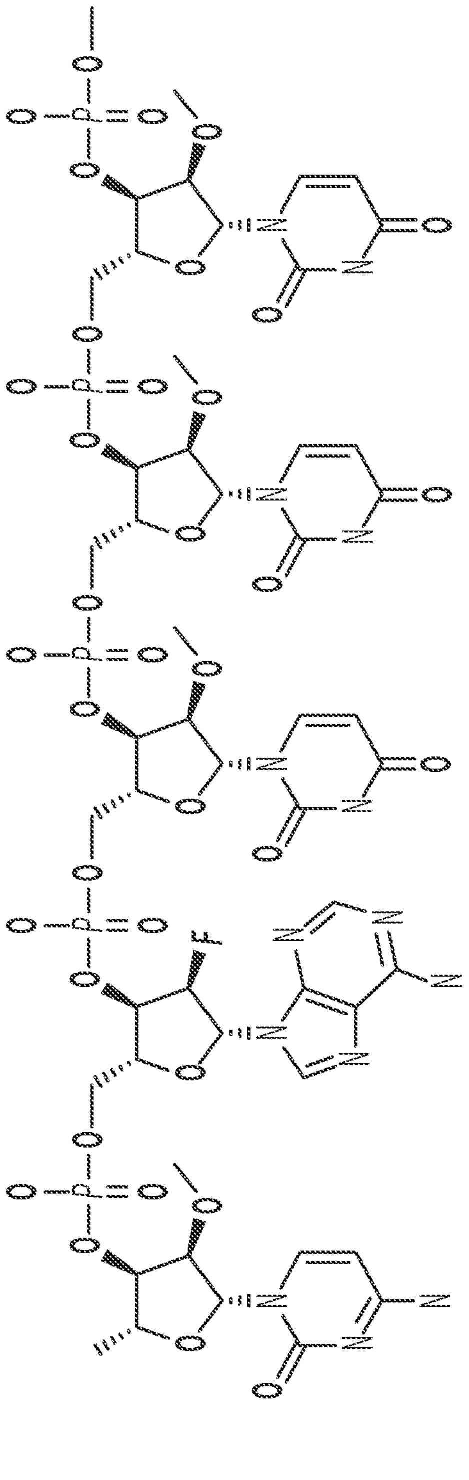
Figure 10:
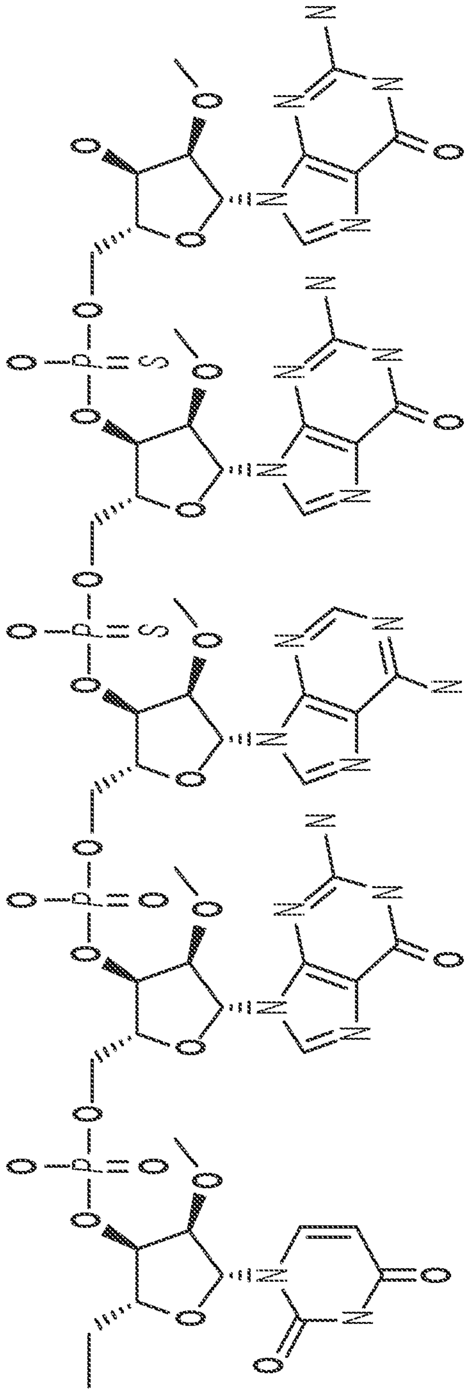

Example 6. ANGPTL3 Antisense Strand at 51.5 Umol Scale, with Wash Solvent Integration from One Cycle to the Next The ANGPTL3 Antisense strand is prepared using the fluidized bed method of the current invention and comprises deblocking, coupling, oxidizing (or sulfurization), and capping steps to sequentially install the phosphoramidites. Capping is not needed after cycle 21 MeMOP phosphoramidite is added. This example uses an alternative research scale synthesizer design. The new design does not have feed zones for reagents, other than amidites and activator. It uses fewer pumps with multiple heads in parallel, and it has integrated solvent re-use from one phosphoramidite cycle to the next, which reduces solvent wash volumes. The experiment is a baseline synthesis of a 22 mer single strand RNA (ANGPTL3 antisense strand) at 51.5 umol scale. The sequence of this RNA strand is shown in FIG. 10 and can be abbreviated as follows, where * indicates thiolation instead of oxidation:

5' MeMOP*fG*fU*fAfUmA fAmCmC fUmUmC fAmUmUmUmUmGmA*mG*mG3

Figure 7:
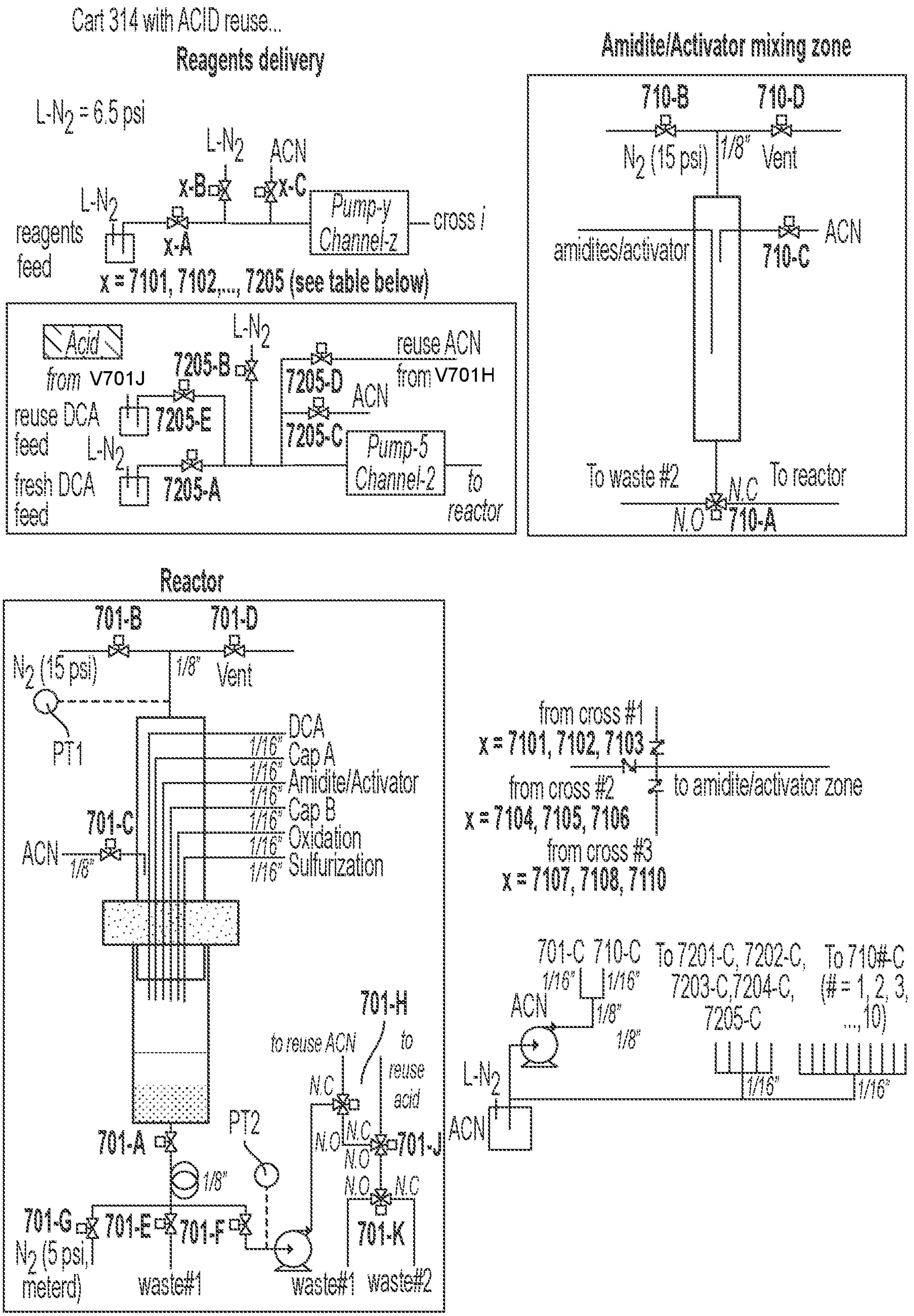
FIG. 7 is a schematic view of an alternative research scale fluidized bed oligonucleotide synthesizer setup.

A 0.63 cm i.d. by 10 cm tall PFA tube was used as the reactor. A summary of synthesis conditions is listed in Table 14. 0.2087 g of NittoPhase HL 250 2'OMeG(IBU) resin was used and yielded 0.6287 g of final resin mass. The crude mass gain was therefore 0.4200 g. Normalizing to one mmol scale gave 8.16 g/mmol. UPLC results showed 82.7% FLP. UPLC and yield results are shown in Table 17. Total OD normalized by synthesis scale gave 171 OD/umol. Solvent usage compared to a typical synthesis from Cytiva AKTA OP100 synthesizer is listed in Table 15. Compared to examples 1-4, Example 6 used significantly less ACN wash solvent per mmol. Table 31 is a guide to the various embodiments in the fluid bed reactor examples. Comparison of purity, yield, and impurity profiles between syntheses from cart 314 fluid bed reactor and from the AKTA synthesizer is shown in Table 17. A schematic diagram of the synthesizer is shown in FIG. 7. Automation procedures for the synthesizer are written in Table 18. Maximum pressure drop across the resin bed is 15 psig during the experiment, because that is the pressure of the supply nitrogen used to push liquid through the resin bed.

TABLE 14

Summary of synthesis conditions used in Example 6.

| Item | Condition |
|---|---|
| Detritylation reaction | 15~18 mL of 3% DCA<br>7~8 minutes of contact time |
| Acid wash ACN volume | 14 mL |
| Coupling pre-wash ACN volume | 3 mL |
| Coupling reaction | 10 minutes of coupling time for all 2'OMe- amidites<br>20 minutes of coupling time for all fluro amidites |
| Coupling wash ACN volume | 9 mL |
| Sulfurization reaction | 3.5 mL of 0.2M xanthane hydride in pyridine<br>5~6 minutes of contact time |
| Sulfurization wash ACN volume | 10 mL |
| Oxidation reaction | 2~2.6 mL of 0.05M iodine in pyridine/water (90/10 by volume)<br>2 minutes of contact time |
| Oxidation wash ACN | 10 mL |
| volume capping reaction | 1 mL of each Cap A and Cap B reagent<br>1 minutes of contact time |
| Capping wash ACN volume | 10 mL |

TABLE 15

Solvent usage compared to a typical synthesis from Cytiva AKTA OP100 synthesizer.

| | "AKTA Compare 3" values (Table 17), scaled down to 50 umol | Example 6 (Table 17), at 51.5 umol scale |
|---|---|---|
| Acid wash total | 14 | 10.44 |
| Coupling pre-wash | 4 | 3.8 |
| Coupling push | 2.33 | 0 |
| Coupling wash | 10 | 0 |
| Coupling total | 16.33 | 3.8 |
| Additional Reactor Wash A. | 0 | 8 |
| Thio push | 4.33 | 0 |
| Thio wash | 4.67 | 1.44 |
| Thio total | 9 | 1.44 |
| Ox push | 4.33 | 0 |
| Ox wash | 6 | 1.47 |
| OX total | 10.33 | 1.47 |
| Capping push | 4.33 | 0 |
| Capping wash | 7.33 | 2.93 |
| Capping Total | 11.67 | 2.93 |
| Additional Reactor Wash B. | 0 | 6 |
| Total ACN per OX cycle | 52.33 | 32.64 |
| Total ACN per SULF cycle | 51 | 32.62 |
| Average ACN use | 52.02 | 32.63 |
| Volume of ACN reduction compared to AKTA baseline (%) | 100% | 37% |

Four experiments were run in the AKTA OP100 synthesizer for comparison. These are represented in Table 17.

The materials and synthesizer conditions used for the four experiments were run in the AKTA OP100 are listed in Table 16.

All 4 experiments in Table 16 used:

Cytiva AKTA OP100

Kinnovate NittoPhase HL-2'-OMeG(iBu) 250 resin, lot G08004, 247 umol/g loading.

Deblocking, Dichloroacetic acid (DCA) in toluene

2CV ACN push after coupling, oxidation, thiolation, capping

Amidite equivalence=2 eq

Activator reagent, 0.5 M 5-(Ethylthio)-1H-tetrazole in ACN

Coupling time=10 min

Oxidization reagent, 0.05 M Iodine in pyridine/water (90/10 v/v)

Oxidization equivalence=4 eq

Oxidization contact time=3 min

Sulfurization reagent, 0.2 M Xanthane hydride in ACN/pyridine (70/30 v/v)

Xanthane hydride amount used, 2 CV

Xanthane hydride=13 eq

Sulfurization contact time=5.5 min

Capping solution A, 1-Methylimidazole/ACN (20/80 v/v)

Capping solution B, 1:1 Mixture B1 and B2

Capping solution B1, 40 vol % acetic anhydride in ACN

Capping solution B2, 60 vol % 2,6-lutidine in ACN

Total amount of capping solutions A and B in 50/50 v/v mixture=2 CV

Capping contact time=0.5 mc a

DEA, 2000 diethylamine in ACN (20/80 v/v)

DEA contact time=10 min

DEA volume=10 mL

TABLE 16

Cytiva AKTA experimental conditions.

| experiment | AKTA compare 1 | AKTA compare 2 | AKTA compare 3 | AKTA compare 4 |
|---|---|---|---|---|
| Synthesis scale, umol | 626 | 160.8 | 161.8 | 149.7 |
| Reactor volume, mL | 25 | 6.3 | 6.3 | 6.3 |
| Reactor diameter, cm | 2.54 | 2 | 2 | 2 |
| Reactor height, cm | 4.93 | 2 | 2 | 2 |
| Deblocking, vol % DCA | 10 | 3 | 3 | 3 |
| Deblocking solution, average amount per cycle, mL | 150.5 | 41.2 | 42.4 | 44.6 |
| Deblocking linear velocity, cm/h | 469 | 200 | 200 | 200 |

TABLE 16-continued

Cytiva AKTA experimental conditions.

| experiment | AKTA compare 1 | AKTA compare 2 | AKTA compare 3 | AKTA compare 4 |
|---|---|---|---|---|
| ACN volume for deblock wash, mL | 150 | 38 | 13 mL ACN, then 6 mL 20% Lutidine in ACN, then 25 mL ACN | 37.8 |
| Amidite concentration, M in ACN | 0.2 | 0.2 | 0.2 | 0.1 |
| Activator equivalence, eq | 7 | 7 | 7 | 10 |
| ACN volume for coupling wash, mL | 100 | 25 | 25 | 25.2 |
| ACN volume for oxidization wash, mL | 29 | 12 | 12 | 12.6 |
| ACN volume for sulfurization wash, mL | 38 | 10 | 10 | 9.45 |
| ACN volume for capping wash, mL | 75 | 19 | 19 | 18.9 |
| ACN volume for DEA wash (final wash), mL | 200 | 50 | 50 | 50.4 |

In each experiment listed in Table 16, after drying the resin bound oligonucleotide, about 20 mg of resin was suspended in 0.50 mL of NH4OH and shaken at 55 C for 4 hours or 38 C for 18 hours. The resin was filtered and the filtrate analyzed by UPLC (50 uL of filtrate diluted with 1.5 mL of water). UPLC purity is shown in Table 17.

TABLE 17

Comparison of purity, yield, and impurity profiles between syntheses from fluid bed synthesizers Examples 6-10 and from AKTA OP100 synthesizer.

a.

Figure 8:
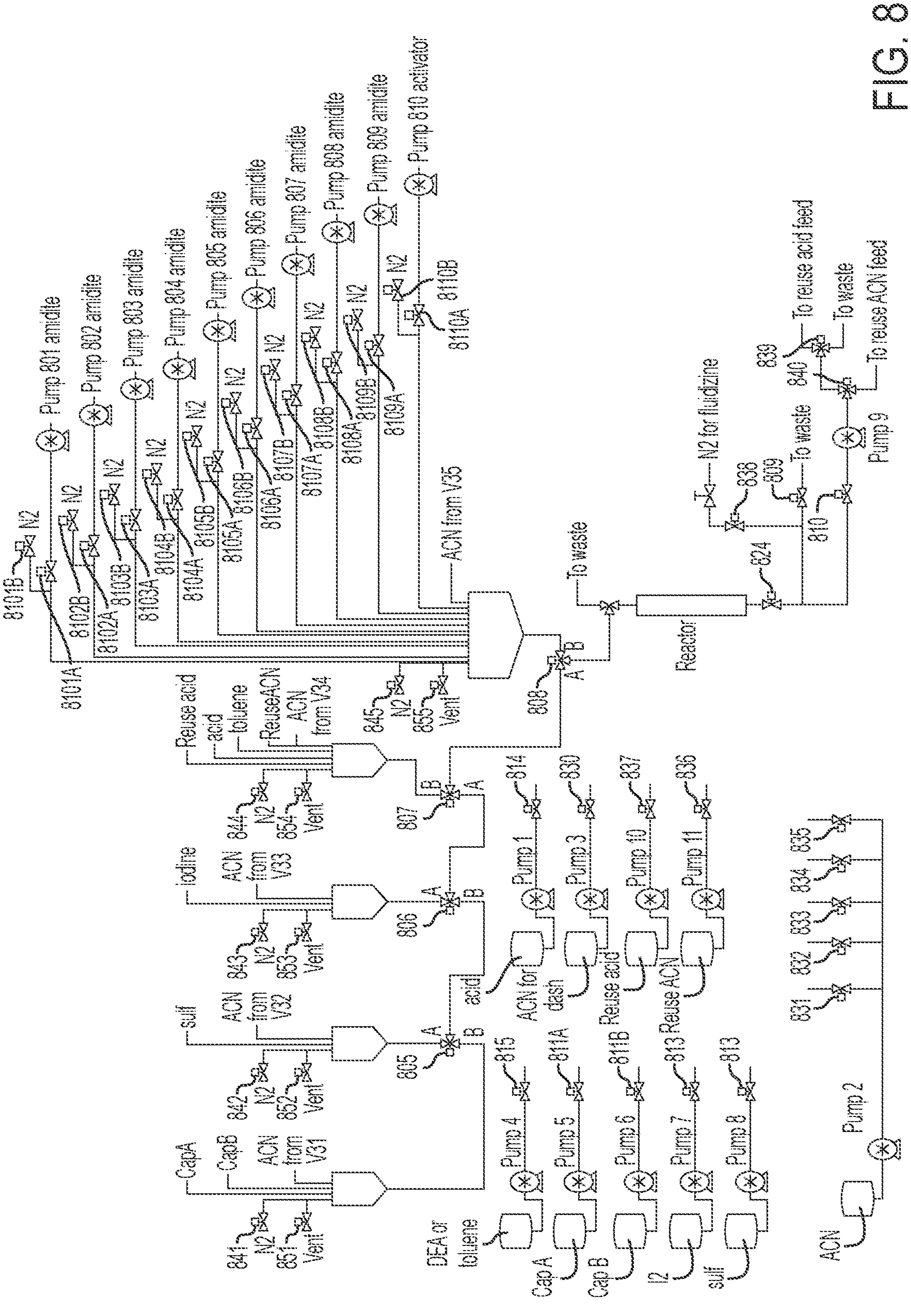
FIG. 8 is a schematic view of an alternative research scale fluidized bed oligonucleotide synthesizer setup.
Figure 9:
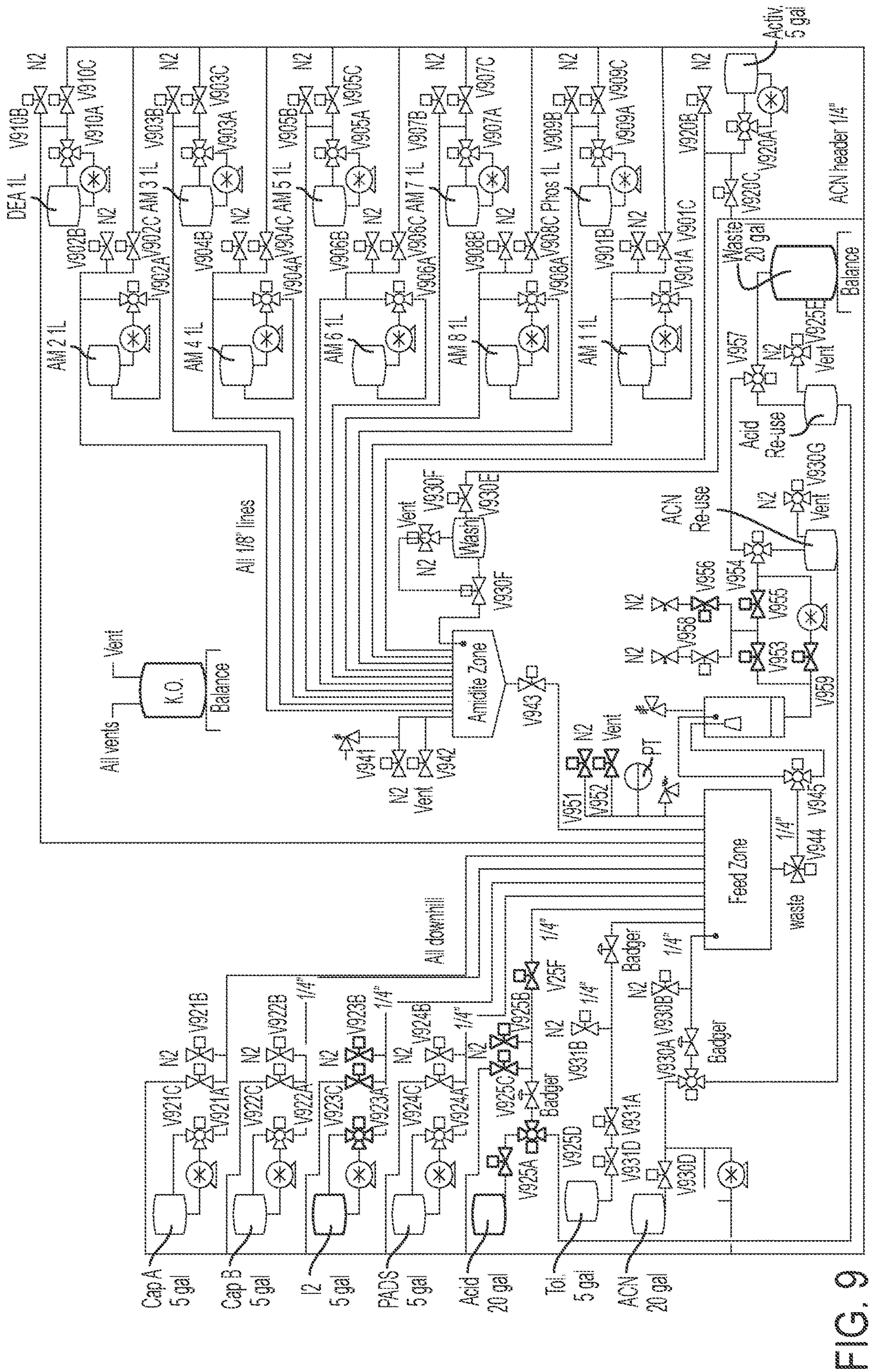
FIG. 9 is a schematic view of an alternative pilot scale fluidized bed oligonucleotide synthesizer setup.
Figure 11:
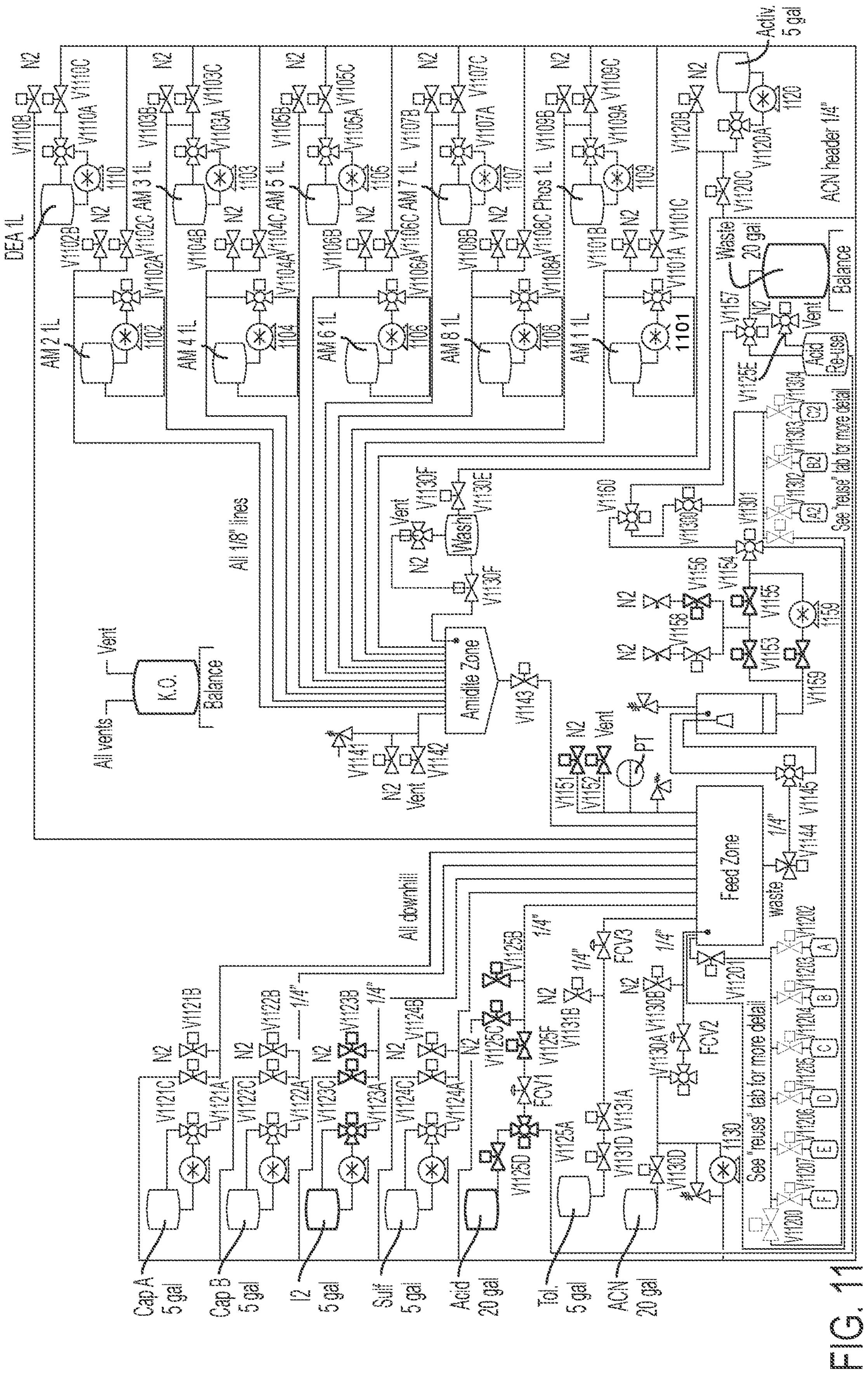
FIG. 11 is a schematic view of an alternative pilot scale fluidized bed oligonucleotide synthesizer setup.

| MeMOP antisense strand synthesis example | Example 6, FBR 50 umol, with reuse ACN | Example 7, FBR 100 umol, with reuse DCA | Example 8, FBR 10 mmol, with reuse ACN | Example 9, FBR 10 mmol, with reuse DCA and multi-pass washing | Example 10, FBR 10 mmol, lowest wash solvent |
|---|---|---|---|---|---|
| scale (mmol) | 0.0515 | 10042 | 10.00 | 10.06 | 10 |
| Synthesizer | FIG. 7 | FIG. 8 | FIG. 9 | FIG. 11 | FIG. 11 |
| resin lot | G08004 | H08023 | G08004 | H08023 | H08023 |
| resin loading (umol/g) | 247 | 249 | 247 | 249 | 249 |
| crude mass gain (g/mmol) | 8.16 | 8.13 | 7.99 | 7.55 | 7.61 |
| OD/umol | 171 | 181 | 161 | 166 | 179 |
| resin bed height final deblock, cm | 7 | 12 | 6 | 6 | 6 |
| reactor i.d. (cm) | 0.63 | 0.63 | 10 | 10 | 10 |

b.

| MeMOP antisense strand synthesis example | AKTA compare 1, 626 umol | AKTA compare 2, 161 umol | AKTA compare 3, 162 umol | AKTA compare 4, 150 umol |
|---|---|---|---|---|
| scale (mmol) | 0.626 | 0.1608 | 0.1618 | 0.1497 |
| Synthesizer | Cytiva AKTA OP100 | Cytiva AKTA OP100 | Cytiva AKTA OP100 | Cytiva AKTA OP100 |
| resin lot | G08004 | G08004 | G08004 | G08004 |
| resin loading (umol/g) | 247 | 247 | 247 | 247 |
| crude mass gain (g/mmol) | 8.26 | 7.06 | 6.16 | 7.54 |

TABLE 17-continued

| Comparison of purity, yield, and impurity profiles between syntheses from fluid bed synthesizers Examples 6-10 and from AKTA OP100 synthesizer. | | | | |
|---|---|---|---|---|
| OD/umol | 158.54 | 149 | 135.67 | 165 |
| resin bed height final deblock, cm | 5 | 2 | 2 | 2 |
| reactor i.d. (cm) | 2.54 | 2 | 2 | 2 |

c.

| | MeMOP antisense strand synthesis example | Example 6, FBR 50 umol, with reuse ACN | Example 7, FBR 100 umol, with reuse DCA | Example 8, FBR 10 mmol, with reuse ACN | Example 9, FBR 10 mmol, with reuse DCA and multi-pass washing | Example 10, FBR 10 mmol, lowest wash solvent |
|---|---|---|---|---|---|---|
| RRT | ID | area % | area % | area % | area % | |
| 0.387 | | | | | | |
| 0.483 | 7mer | | 0.35 | | | |
| 0.547 | 8mer | | 0.41 | | | |
| 0.627 | 9mer | | 0.28 | | | |
| 0.663 | 10mer | | 0.24 | | 0.27 | |
| 0.703 | 11mer | | | | 0.28 | |
| 0.743 | 12mer | | | | 0.34 | 0.24 |
| 0.778 | 13mer | | 0.55 | | 0.36 | |
| 0.807 | 14mer | | 0.27 | | 0.31 | 0.24 |
| 0.831 | 15mer | | 0.34 | 0.27 | 0.53 | 0.38 |
| 0.869 | 16mer | | 0.35 | 0.26 | 0.44 | 0.38 |
| 0.911 | 17mer | | 0.76 | 0.59 | 0.51 | 0.55 |
| 0.915 | 18mer | 0.22 | 0.53 | 0.63 | 0.63 | 0.61 |
| 0.937 | 19mer | 0.24 | 0.78 | 0.92 | 2.08 | 0.75 |
| 0.956 | 20mer | 0.33 | 0.62 | 1.05 | 0.84 | 0.79 |
| 0.963 | 21mer PO | | 0.57 | | 0.4 | 0.25 |
| 0.972 | 21mer | 0.38 | 2.02 | 1.64 | 1.88 | 0.96 |
| 0.979 | | | | | | |
| 0.984 | | 0.54 | | | 0.48 | |
| 0.986 | PS to PO and N-1 | 0.71 | 1.6 | 1.07 | 0.75 | 1.04 |
| 0.989 | PS to PO | | 1.98 | | | |
| 0.993 | PS to PO | 5.31 | 2.5 | 4.14 | 4.01 | 3.06 |
| 0.995 | related to PS to PO | | | 1.64 | | |
| 1 | FLP | 82.7 | 79.92 | 79.5 | 77.89 | 82.32 |
| 1.006 | | | | | | |
| 1.008 | | 0.67 | 1.18 | | 0.55 | 0.47 |
| 1.01 | | 0.58 | | 1.23 | 0.33 | 0.45 |
| 1.013 | | 1.36 | 0.76 | 0.85 | 0.46 | 0.42 |
| 1.016 | | | | | 0.45 | 0.47 |
| 1.023 | Plus 14.02 Da** | 3.06 | 2.77 | 3.26 | 3.2 | 3.04 |
| 1.03 | isobuteryls* | | | 0.24 | | |
| 1.04 | isobuteryls* | 0.21 | | 0.5 | 0.28 | 0.23 |
| 1.05 | isobuteryls* | | | 0.27 | 0.38 | 0.32 |
| 1.07 | isobuteryls* | | | | | |
| 1.1 | isobuteryls* | 0.22 | | | | |
| 1.13 | | 0.24 | | | | |
| 1.14 | | 0.25 | | | | |
| | total area % of peaks shown (not showing peaks <0.2% | 97.02 | 98.78 | 98.06 | 97.65 | 96.01 |
| | total area % before main | 7.73 | 14.15 | 12.21 | 14.11 | 8.29 |
| | total area % after main | 6.59 | 4.71 | 6.35 | 5.65 | 5.4 |
| | PS to PO related peaks, RRT 0.986, 0.989, 0.993, 0.995 | 6.020 | 6.080 | 6.850 | 4.760 | 4.100 |

TABLE 17-continued

Comparison of purity, yield, and impurity profiles between syntheses from fluid bed synthesizers Examples 6-10 and from AKTA OP100 synthesizer.

d.

| | MeMOP antisense strand synthesis example | AKTA compare 1, 626 umol | AKTA compare 2, 161 umol | AKTA compare 3, 162 umol | AKTA compare 4, 150 umol |
|---|---|---|---|---|---|
| RRT | ID | area % | area % | area % | area % |
| 0.387 | | | 0.22 | | |
| 0.547 | 8mer | 0.23 | 0.35 | 1.63 | |
| 0.627 | 9mer | 0.2 | | 0.31 | |
| 0.663 | 10mer | 0.22 | 0.29 | | |
| 0.703 | 11mer | 0.3 | 0.28 | 0.21 | |
| 0.743 | 12mer | 0.38 | 0.53 | 0.45 | |
| 0.778 | 13mer | 0.25 | | | |
| 0.807 | 14mer | 0.28 | | | |
| 0.831 | 15mer | 0.43 | 0.41 | 0.46 | 0.33 |
| 0.869 | 16mer | 0.32 | 0.29 | 0.45 | 0.22 |
| 0.911 | 17mer | 0.5 | 0.47 | 0.41 | 0.22 |
| 0.915 | 18mer | 0.62 | 0.56 | 0.47 | 0.39 |
| 0.937 | 19mer | 0.6 | 0.59 | 0.5 | 0.27 |
| 0.956 | 20mer | 1.29 | 0.95 | 0.75 | 0.45 |
| 0.963 | 21mer PO | 0.37 | | 0.23 | |
| 0.972 | 21mer | 0.78 | 0.6 | 0.58 | 0.42 |
| 0.979 | | 0.4 | 0.3 | | |
| 0.984 | | | | | |
| 0.986 | PS to PO and N-1 | 1.38 | 1.86 | 1.22 | 1.01 |
| 0.993 | PS to PO | 6.78 | 6.56 | 5.39 | 4.58 |
| 0.995 | related to PS to PO | | 2.63 | | |
| 1 | FLP | 74.91 | 77.42 | 80.67 | 83.96 |
| 1.006 | | 0.56 | 0.6 | 2.08 | |
| 1.008 | | 0.6 | 1.46 | | 2.49 |
| 1.01 | | | | | |
| 1.013 | | 1.96 | | | |
| 1.016 | | | | | |
| 1.023 | Plus 14.02 Da** | 2.680 | 2.39 | 2.79 | 3.04 |
| 1.03 | isobuteryls* | 0.25 | | | |
| 1.04 | isobuteryls* | 0.26 | | | |
| 1.05 | isobuteryls* | | | | |
| 1.07 | isobuteryls* | 0.26 | | | |
| 1.1 | isobuteryls* | 0.29 | | | |
| 1.13 | | 0.22 | | | |
| 1.14 | | | | | |
| | total area % of peaks shown (not showing peaks <0.2% | 97.32 | 98.76 | 98.6 | 97.38 |
| | total area % before main | 15.33 | 16.89 | 13.06 | 7.89 |
| | total area % after main | 6.52 | 3.85 | 2.79 | 5.53 |
| | PS to PO related peaks, RRT 0.986, 0.989, 0.993, 0.995 | 8.160 | 11.050 | 6.610 | 5.590 |

*isobuteryls indicating incomplete C/D

**The plus 14.02 Da was a methyl migration impurity related to the MeMOP amidite starting material, migrating to one of the fU amidites.

The area percent peaks identified in the 0.979-0.984 RRT region and the 1.006-1.016 RRT region in the table might lead one to think that there are differences between the synthesizers, but the chromatograms reveal that none of them are actually distinct peaks in these regions. For example, there are peaks identified at 0.979 RRT for the AKTA examples that are not in the fluid bed reactor examples. Likewise, there are peaks identified at 0.984 RRT for the fluid bed reactor examples that are not in the AKTA examples. However, inspection of the chromatograms in FIG. 17 reveals that these are similar far left shoulders on the main peak, and the identified peak times simply depend on where the lines were drawn by the automated integration. Similarly, there is an elevated region above the baseline in the between 1.006 RRT and 1.016 RRT which gets assigned differently depending on where the automated integration lines are drawn, but it is a similar region of elevated baseline in all the samples. The table might lead one to think that there are peaks at 1.006 RRT in the AKTA samples that are not in fluid bed reactor samples, and that there are peaks at 1.01 RRT in the fluid bed reactor samples that are not in AKTA samples, but the chromatogram in FIG. 17 reveals that there are really not significant differences between the samples from the different synthesizers in those RRT regions.

TABLE 18

| Automation procedures of cart 314 |
|---|
| Typical list of automation steps: |
| 1) ACID (performing detritylation reaction)<br>2) Wash of type DCA (wash acid/DCA feed line)<br>3) Wash of type Reactor (wash reactor)<br>4) Wash of type Amidite (wash amidite/activator mixing zone)<br>5) CPL purge (purge amidite and activator)<br>6) CPL (coupling reaction)<br>7) Wash of type Amidite (wash amidite/activator mixing zone)<br>8) Wash of type Reactor (wash reactor)<br>9) Oxidation or Sulfurization (performing Oxidation or Sulfurization reaction)<br>10) Wash of type I2 or SULF depending on step 9) (wash Oxidation or sulfurization feed line)<br>11) Wash of type Reactor (wash reactor)<br>12) CAP (performing capping reaction)<br>13) Wash of type CAP (wash Cap A and Cap B feed lines)<br>14) Wash of type Reactor (wash reactor) |
| Step name: ACID |
| Purpose: execute detritylation reaction<br>Open V701-D to vent reactor<br>Open V7205-B for 2 sec, close V7205-B<br>Open V7205-A, Open V7204-B<br>Read acid balance, waste balance.<br>Start Pump 5 at an INPUT FLOW RATE for a time duration calculated based on an INPUT VOLUME: VOL1<br>Close V7205-A, Open V7205-B<br>Run Pump 5 for an INPUT TIME DURATION to clear acid path<br>Close V7204-B, V7205-B.<br>Close V701-D. Open V701-A. Do fluidization for INPUT TIMES as follows:<br>Open V701-B for INPUT DURATION, then close V701-B.<br>Open V701-G, V701-D for INPUT DURATION, then close V701-D, V701-G.<br>Open V701-D to vent reactor<br>Open V7205-B for 2 sec, then close V7205-B.<br>Open V7205-A, Open V7204-B<br>Start timer count for INPUT TIME DELAY and at the same time start Pump 5 at INPUT FLOW RATE for a time duration determined by an INPUT FLOW RATE for Pump 5 and an INPUT VOLUME, VOL2, for acid amount.<br>When the timer is off, close V701-D, open V701-B, open V701-F, and start waste pump at INPUT RATE<br>When the volume of VOL2 of acid was charged, Close V7205-A, Open V7205-B, continue running Pump 5 for an INPUT TIME DURATION to clear acid path<br>Close V7204-B, V7205-B. Open V701-E.<br>Close V701-F, V701-B<br>Wait for PT1 < an INPUT PRESSURE to close V701-A, V701-E. |
| Step name: WASH with type DCA |
| Purpose: wash acid line with ACN<br>Open V701-D to vent reactor<br>Open V7205-C, Open V7204-B<br>Start Pump 5 at an INPUT FLOW RATE for a time duration calculated based on an INPUT VOLUME<br>Close V7205-C, Open V7205-B<br>Start Pump 5 for an INPUT TIME DURATION to clear acid path<br>Close V7204-B, V7205-B.<br>Open V701-C, start ACN pump P6 at INPUT FLOW RATE for time duration calculated based on an INPUT VOLUME<br>Close V701-C. Close V701-D. Open V701-A. Do fluidization for INPUT # TIMES as follows<br>Open V701-B for an INPUT TIME, then close V701-B.<br>Open V701-G, V701-D for INPUT DURATION, then close V701-D, V701-G.<br>If parameter WP TIME > 0, open V-701B, V701-F start waste pump at an INPUT RATE running for an INPUT TIME DURATION.<br>Close V701-F, open V701-E<br>keep V701-B, V701-A, V701-E open for an INPUT TIME<br>close V701-B and wait for PT1 < an INPUT PRESSURE<br>close V701-A and V701-E and complete this step. |

TABLE 18-continued

| Automation procedures of cart 314 |
|---|
| Step name: WASH type reactor |
| Purpose: directly wash the reactor<br>Open V701-D to vent reactor<br>Open V701-C, start ACN pump P6 at an INPUT FLOW RATE for time duration calculated based on an INPUT VOLUME<br>Close V701-C, open V701-A, close V701-D. Do fluidization for an INPUT # TIMES as follows<br>Open V701-B for an INPUT TIME, then close V701-B.<br>Open V701-G, V701-D for INPUT DURATION, then close V701-D, V701-G.<br>If parameter WP TIME > 0, open V701-B, V701-F, start waste pump at an INPUT RATE running for an INPUT TIME DURATION.<br>Close V701-F. Open V701-E.<br>keep V701-B, V701-A, V701-E open for an INPUT TIME<br>close V701-B and wait for PT1 < an INPUT PRESSURE<br>close V701-A and V701-E and complete this step. |
| Step name: CPL Purge source AM-x (x = 1, 2, . . . , 8) |
| Purpose: purge amidite solution to waste (optional, typically consumes 0.5 mL of amidite solution for each purge, only used at 50 umol scale to overcome moisture permeation issue through PFA tubings.)<br>Direct V710-A to waste<br>Open V710-D to vent amidite/activator zone.<br>Open V710x-B for 2 sec, close V710x-B.<br>Open V710x-A, open V710x2-B and V710x3-B where x, x2, and x3 are on the same pump.<br>Start Pump y at an INPUT RATE for time duration calculated from an INPUT VOLUME<br>close V710x-A, open V710x-B, continue Pump y for an INPUT TIME DURATION.<br>Open V7110-B for 2 sec, close V7110-B.<br>Open V7110-A, open V7107-B and V7108-B.<br>Start Pump y at an INPUT RATE for time duration calculated from an INPUT VOLUME<br>close V7110-A, open V7110-B, continue running Pump y for an INPUT TIME DURATION<br>Close V710-D, open V710-B for an INPUT TIME DURATION. Close V710-B. |
| Step name: CPL with source AM-x (x = 1, 2, . . . , 8) |
| Purpose: charge amidite and activator to execute CPL reaction and wash<br>Direct V710-A to reactor<br>Open V710-D to vent amidite/activator zone.<br>Open V710x-B for 2 sec, close V710x-B.<br>Open V710x-A, open V710x2-B and V710x3-B where x, x2, and x3 are on the same pump.<br>Start Pump y at an INPUT RATE for time duration calculated from an INPUT VOLUME<br>close V710x-A, open V710x-B, continue pump y for an INPUT TIME DURATION.<br>Open V7110-B for 2 sec, close V7110-B.<br>Open V7110-A, open V7107-B and V7108-B.<br>Start Pump y at an INPUT RATE for time duration calculated from an INPUT VOLUME<br>close V7110-A, open V7110-B, continue running Pump y for an INPUT TIME DURATION<br>Close V710-D, open V710-A, V701-D<br>open V710-B for an INPUT TIME DURATION.<br>Close V710-B, V710-A, and V701-D.<br>Open V701-A. Repeating fluidization for an INPUT TIME DURATION as follows<br>Open V701-B for an INPUT TIME, then close V701-B.<br>Open V701-G, V701-D for INPUT DURATION, then close V701-D, V701-G.<br>keep V701-B, V701-A, V701-E open for an INPUT TIME.<br>close V701-B and wait for PT1 < an INPUT PRESSURE.<br>close V701-A and V701-E and complete this step. |

TABLE 18-continued

| Automation procedures of cart 314 |
| --- |
| Step name: wash with type AMx (x = 1, 2, . . . , 8) |
| Purpose: wash amidite zone |
| Open V710-D to vent amidite/activator zone. |
| Open V710x-C for x=1, 2, . . . 10 |
| Run Pump 1, Pump 2, and Pump 3 at an INPUT RATE for an INPUT TIME DURATION |
| Close V710x-C for x=1, 2, . . . 10 |
| Open V710x-B for x=1, 2, . . . 10 |
| Run Pump 1, Pump 2, and Pump 3 at an INPUT RATE for INPUT TIME DURATION |
| Open V710-C, start ACN pump P6 at an INPUT RATE for an INPUT TIME DURATION to wash down the walls of the AMD/ACT zone |
| Close V710-C |
| Close V710-D, direct V710-A to reactor, open V701-D |
| Open V710-B for an INPUT TIME DURATION |
| Direct V710-A to waste, Close V701-D, Open V701-A. Do fluidization for an INPUT # TIMES as follows |
| Open V701-B for an INPUT TIME, then close V701-B. |
| Open V701-G, V701-D for INPUT DURATION, then close V701-D, V701-G. |
| If parameter WP time > 0, open V701-B, V701-F, start waste pump at an INPUT RATE running for an INPUT TIME DURATION. |
| keep V701-B, V701-A, V701-E open for an INPUT TIME |
| close V701-B and wait for PT1 < user input |
| close V701-A and V701-E and complete this step. |
| Step name: Oxidation |
| Purpose: performing Oxidation reaction |
| Open V701-D to vent reactor |
| Open V7203-B for 2 sec, close V7203-B |
| Open V7203-A, open V7201-B, V7202-B |
| Start Pump 4 at an INPUT FLOW RATE for a time duration calculated based on an INPUT VOLUME VOL1 |
| Close V7203-A, open V7203-B |
| Start Pump 4 for an INPUT TIME DURATION to clear tubing |
| Close V7201-B, V7202-B, V7203B |
| Close V701-D. Open V701-A. Do fluidization for an INPUT # TIMES as follows |
| Open V701-B for an INPUT TIME, then close V701-B. |
| Open V701-G, V701-D for INPUT DURATION, then close V701-D, V701-G. |
| If parameter WP time > 0, open V701-B, V701-F, start waste pump at an INPUT RATE running for an INPUT TIME DURATION. |
| Close V701-F. Open V701-E. |
| keep V701-B, V701-A, V701-E open for an INPUT TIME |
| close V701-B and wait for PT1 < an INPUT PRESSURE |
| close V701-A and V701-E and complete this step. |
| Step name: wash with type of I2 |
| Purpose: performing post Oxidation wash |
| Open V701-D to vent reactor |
| Open V7203-B for 2 sec, close V7203-B |
| Open V7203-C, open V7201-B, V7202-B |
| Start Pump 4 at an INPUT FLOW RATE for a time duration calculated based on an INPUT VOLUME VOL1 |
| Close V7203-C, open V7203-B |
| Start Pump 4 for an INPUT TIME DURATION to clear tubing |
| Close V7201-B, V7202-B, V7203B |
| Open V701-C |
| Run ACN pump P6 at an INPUT FLOW RATE for a time duration calculated based on an INPUT VOLUME to wash down the reactor walls. |
| Close V701-C. |
| Close V701-D. Open V701-A. Do fluidization for an INPUT # TIMES as follows |
| Open V701-B for an INPUT TIME, then close V701-B. |
| Open V701-G, V701-D for INPUT DURATION, then close V701-D, V701-G. |
| If parameter WP time > 0, open V701-B, V701-F, start waste pump at an INPUT RATE running for an INPUT TIME DURATION. |
| Close V701-F. Open V701-E. |
| keep V701-B, V701-A, V701-E open for an INPUT TIME |
| close V701-B and wait for PT1 < an INPUT PRESSURE |
| close V701-A and V701-E and complete this step. |

TABLE 18-continued

| Automation procedures of cart 314 |
|---|
| Step name: SULF |
| Purpose: performing sulfurization reaction<br>Open V701-D to vent reactor<br>Open V7204-B for 2 sec, close V7204-B<br>Open V7204-A, open V7205-B<br>Start Pump 5 at an INPUT FLOW RATE for a time duration calculated based on an INPUT VOLUME VOL1<br>Close V7204-A, open V7204-B<br>Start Pump 5 for an INPUT TIME DURATION to clear tubing<br>Close V7204-B, V7205-B.<br>Close V701-D. Open V701-A. Do fluidization for an INPUT # TIMES as follows<br>Open V701-B for an INPUT TIME, then close V701-B.<br>Open V701-G, V701-D for INPUT DURATION, then close V701-D, V701-G.<br>If parameter WP time > 0, open V701-B, V701-F, start waste pump at an INPUT RATE running for an INPUT TIME DURATION.<br>Close V701-F. Open V701-E<br>Keep V701-B, V701-A, V701-E open for an INPUT TIME<br>Close V701-B and wait for PT1 < user input<br>Close V701-A and V701-E and complete this step. |
| Step name: wash with type SULF |
| Purpose: performing sulfurization wash<br>Open V701-D to vent reactor<br>Open V7204-B for 2 sec, close V7204-B<br>Open V7204-C, open V7205-B<br>Start Pump 5 at an INPUT FLOW RATE for a time duration calculated based on an INPUT VOLUME VOL1<br>Close V7204-C, open V7204-B<br>Start Pump 5 for an INPUT TIME DURATION to clear tubing<br>Close V7204-B, V7205-B.<br>Open V701-C<br>Run ACN pump P6 at an INPUT FLOW RATE for time duration calculated based on an INPUT VOLUME.<br>Close V701-C.<br>Close V701-D. Open V701-A. Do fluidization for an INPUT # TIMES as follows<br>Open V701-B for an INPUT TIME, then close V701-B.<br>Open V701-G, V701-D for INPUT DURATION, then close V701-D, V701-G.<br>If parameter WP time > 0, open V701-B, V701-F, start waste pump at an INPUT RATE running for an INPUT TIME DURATION.<br>Close V701-F. Open V701-E<br>Keep V701-B, V701-A, V701-E open for an INPUT TIME<br>Close V701-B and wait for PT1 < user input<br>Close V701-A and V701-E and complete this step. |
| Step name: CAP |
| Purpose: performing capping reaction<br>Open V701-D to vent reactor<br>Open V7201-B, V7202-B for 2 sec<br>Close V7201-B, V7202-B<br>Open V7201-A, V7202-A, V7203-B<br>Start Pump 4 at an INPUT FLOW RATE for a time duration calculated based on an INPUT VOLUME VOL1<br>Close V7201-A, V7202-A. Open V7201-B, V7202-B.<br>Start Pump 4 for an INPUT TIME DURATION to clear tubing<br>Close V7201-B, V7202-B, V7203B<br>Close V1-D. Open V701-A. Do fluidization for an INPUT # TIMES as follows<br>Open V701-B for an INPUT TIME, then close V701-B.<br>Open V701-G, V701-D for INPUT DURATION, then close V701-D, V701-G.<br>If parameter WP time > 0, open V701-B, V701-F, start waste pump at an INPUT RATE running for an INPUT TIME DURATION.<br>Close V701-F. Open V701-E<br>keep V701-B, V701-A, V701-E open for an INPUT TIME<br>close V701-B and wait for PT1 < an INPUT PRESSURE<br>close V701-A and V701-E and complete this step. |

TABLE 18-continued

| Automation procedures of cart 314 |
|---|
| Step name: wash with type CAP |
| Purpose: performing post-capping wash<br>Open V701-D to vent reactor<br>Open V7201-B, V7202-B for 2 sec<br>Close V7201-B, V7202-B<br>Open V7201-C, V7202-C, 7V203-B<br>Start Pump 4 at an INPUT FLOW RATE for a time duration calculated based on an INPUT VOLUME VOL1<br>Close V7201-C, V7202-C. Open V7201-B, V7202-B.<br>Start Pump 4 for an INPUT TIME DURATION to clear tubing<br>Close V7201-B, V7202-B, V7203B<br>Open V701-C<br>Run ACN pump P6 at an INPUT FLOW RATE for time duration calculated based on an INPUT VOLUME.<br>Close V701-C.<br>Close V701-D. Open V701-A. Do fluidization for an INPUT # TIMES as follows<br>Open V701-B for an INPUT TIME, then close V701-B.<br>Open V701-G, V701-D for INPUT DURATION, then close V701-D, V701-G.<br>If parameter WP time > 0, open V701-B, V701-F, start waste pump at an INPUT RATE running for an INPUT TIME DURATION.<br>Close V701-F. Open V701-E.<br>keep V701-B, V701-A, V701-E open for an INPUT TIME<br>close V701-B and wait for PT1 < an INPUT PRESSURE<br>close V701-A and V701-E and complete this step. |

Example 7. ANGPTL3 Antisense Strand at 100 Umol Scale, with DCA Reagent Integration from One Cycle to the Next The same ANGPTL3 Antisense strand shown in FIG. 10 is prepared using the fluidized bed method of the current invention and comprises deblocking, coupling, oxidizing (or sulfurization), and capping steps to sequentially install the phosphoramidites. Example 7 demonstrated the lowest DCA reagent out of all the examples. Capping is not needed after cycle 21 MeMOP phosphoramidite is added. This example used less equivalents of DCA compared to Examples 1, 2, 3, 4, and 6. Table 31 is a guide to the various embodiments in the fluid bed reactor examples. One contributing factor to the reduction in DCA is that each phosphoramidite cycle reuses the cleaner portion of the acid effluent from the previous phosphoramidite cycle. The re-use acid accomplishes a portion of the deblocking. In addition, and perhaps more importantly, the re-use acid washes away the residual ACN in/on the wetted beads from the end of the previous cycle, and it swells the resin beads while fluidized. ACN is known to hinder the DCA deblocking. Previous embodiments accomplished the initial resin fluidization and ACN displacement with fresh DCA solution. The concept is to use the re-use acid instead, to save the need to use fresh acid for this operation stage. The re-use acid is free of ACN because it is the cleaner part of the acid effluent from the previous phosphoramidite cycle. Swelling the resin beads during the initial fluidization reduces the subsequent pressure drop during the ensuing downflow portion of deblocking, because it allows the resin bed to swell and expand while fluidized. Maximum pressure drop across the resin bed is 15 psig during the experiment, because that is the pressure of the supply nitrogen used to push liquid through the resin bed. Another difference compared to previous examples is the decreased volume of capping solutions, which was reduced by 50% to 1.75 mL each of Cap A and Cap B solutions, and third difference is the removal of large fluidized washes between reactions. The process in this example uses 29.2% of the standard amount of acid that is typically used by the Cytiva AKTA (mL acid/mmol starting resin). Refer to FIG. 8 for the synthesizer apparatus setup for acid reuse.

The reuse of acid is accomplished using a separate acid reuse feed bottle and pump. Each synthesis cycle to install a phosphoramidite has 2 acid deblock steps. For the first acid step of each cycle, acid is charged to the reactor from the acid reuse feed bottle. It is pumped through the resin bed more quickly, because the main reasons for using it are to swell the bed while fluidized and then displace ACN from the bed. When exiting the reactor, the acid from the first acid step is pumped to waste. The second acid step charges fresh acid from the fresh acid feed bottle. When exiting the reactor, the acid from the second acid step is pumped back to the acid reuse feed bottle for reuse in the next cycle. For the first cycle of the sequence, the reuse acid feed bottle is charged with enough fresh acid to use in the first acid step. All subsequent steps have reuse acid from the previous cycle in the reuse acid feed bottle. Pumping parameters are set such that all reuse acid from the previous cycle is charged to the reactor. Emptying the reuse bottle every time limits carryover to only one cycle and prevents accumulation in the reuse acid feed bottle.

The process in this example is run at 100 μmol scale with the resin bed height reaching 11 cm ACN solvent wet at the beginning of the last cycle. A maximum resin bed height of 12 cm is reached during downflow portion the final deblocking step. Maximum pressure drop across the resin bed is 15 psig during the experiment. The reactor has a 0.63 cm diameter bottom section 23 cm tall, and a 4.7 cm diameter cone bottom top section 25 cm tall. Prepare the reagent solutions the same as described in Example 6 (Xanthane hydride concentration was 0.2 M). Prime all pumps and feed lines. Place dry packs into the ACN bottle and all syringes. The amidites and activator use syringe pumps, and all other reagent and solvent feeds use peristaltic pumps and feed vessels.

Begin with mG coupled onto NittoPhase HL 2' OMeG (ibu) 250 resin, lot H08023 using known methods (herein referred to as "mG-resin"). Overall synthesis conditions are given in Table 19.

TABLE 19

Synthesis conditions and reagent concentrations for example 7.

| Item | Value | Unit |
|---|---|---|
| Resin loading | 249 | umol/g |
| Resin starting amount | 403.3 | mg |
| Synthesis scale | 100.42 | umol/g |
| Reuse deblocking solution per cycle from previous cycle | 7-18 | mL |
| Reuse acid deblocking time * | 1.83-2.67 | min |
| Fresh deblocking solution amount per cycle | 7-18 | mL |
| Fresh acid deblocking reaction time * | 5.17-8.33 | min |
| Amidite concentration | 0.1 | M in ACN |
| Amidite equivalence | 2 | eq |
| Activator concentration | 0.5 | M in ACN |
| Activator equivalence | 10 | eq |
| Amidite solution amount per cycle | 2 | mL |
| Activator solution amount per cycle | 2 | mL |
| Coupling reaction time | 10-15 | min |
| Iodine equivalence | 2.1 first two oxidation cycles, 2.65 all others | eq |
| Oxidation solution amount per cycle * | 4.2, 5.3 | mL |
| Oxidation time | 6.7-7 | min |
| Sulfurization equivalence | 13 | eq |
| Sulfurization solution amount per cycle | 6.5 | mL |
| Sulfurization time | 12-13 | min |
| Capping solution A amount per cycle | 1.75 | mL |
| Capping solution B amount per cycle | 1.75 | mL |
| Capping time * | 3.8-4 | min |

*this is the total time from when reagents first contact resin to the time that the first ACN wash contacts resin bed.

Final resin bound oligonucleotide mass was 1.220 gram dried. This corresponds to 0.817 gram of weight gain, or 8.13 g/mmol mass gain. Perform the cleavage and deprotection reaction with concentrated NH4OH solution at 55° C. for 5 hours. UPLC shows the cleaved and deprotected oligonucleotide product is 79.9200 pure by peak area percent, as shown in the Table of UPLC results for examples 6 through 9.

The process of using the apparatus of FIG. 8 will now be described. For each phosphoramidite added in the synthesis, perform the deblocking, coupling, oxidizing (or sulfurization where there is a P=S linkage in the sequence), and capping steps sequentially as described below. When this procedure states that liquid is pumped down through the resin bed, it means that the waste pump at the outlet of the reactor bottom runs at a target setpoint, while nitrogen pressure pushes on top of the resin bed to push the liquid down through. The purpose of the peristaltic pump is to meter the liquid flow through the bed at a controlled rate.

Deblock Reaction: The deblock process included reuse deblocking and fresh deblocking steps. The volumes and times increased as a function of the length of the oligonucleotide, are listed in Table 20.

TABLE 20

Increase in DCA solution volume and deblock reaction plug flow contact time from beginning to end of synthesis in example 7.

| cycle | amidite | Fresh DCA solution volume (mL) | plug flow DCA contact time (seconds) |
|---|---|---|---|
| 1 | MGS | 7 | 310 |
| 2 | MAS | 7 | 320 |
| 3 | MG | 8 | 320 |
| 4 | MU | 8 | 340 |
| 5 | MU | 9 | 340 |
| 6 | MU | 9 | 340 |
| 7 | MU | 10 | 360 |
| 8 | FA | 10 | 360 |
| 9 | MC | 11 | 380 |
| 10 | MC | 11 | 380 |
| 11 | MU | 12 | 400 |
| 12 | FU | 12 | 400 |
| 13 | MC | 13 | 420 |
| 14 | MC | 13 | 420 |
| 15 | FA | 14 | 440 |
| 16 | MA | 15 | 440 |
| 17 | FU | 16 | 460 |
| 18 | FA | 17 | 460 |
| 19 | FUS | 17 | 480 |
| 20 | FGS | 18 | 480 |
| 21 | MEMOPS | 18 | 500 |

Reuse deblocking: Turn valve 808 to A, valve 807 to B, and close valve 824. Charge the initial volume of the reuse deblocking solution (5 mL for cycles 1-3, 6 mL for cycles 4-9, 7 mL for cycles 10-21) into the acid feed zone, then push it into the reactor with nitrogen pressure for 6 seconds. The volume of reuse deblocking solution in each cycle matches the volume of fresh deblocking solution in the previous cycle. Open valve 824. The outlet valves to waste (valves 809 and 810 in FIG. 8) are closed. Vent the pressure from the top of the reactor for 15 seconds, while at the same time opening valve 38, causing nitrogen bubbling to agitate and fluidize the resin bed with the reagent solutions. Close the valve 854 vent and valve 838, and open valve 844 to push down with nitrogen for 3 seconds. Close valve 844 and repeat these fluidization steps 4 more times. Most of the resin swelling occurs during fluidization. Open the valve to waste (valve 810) and pump the deblocking solution through the resin bed with Pump 9 at a rate of 10 mL per minute. Pump 9 serves as a metering device to set the outlet rate, while nitrogen pressure in the top of the reactor supplies the driving force for liquid to flow down and out the bottom of the reactor. In parallel to Pump 9 pumping, open valve 837 and start Pump 10 feeding the reuse deblocking solution at 30 mL/min until the second volume of 2-11 mL (depending on the cycle) has been pumped (Pump 10 finishing before Pump 9). Liquid pumping into the acid feed zone from Pump 10 simultaneously flows into the reactor to maintain liquid level above the resin bed and keep the flow going for the entire duration of run time for Pump 9. Pump 9 runs continuously for 110-160 seconds (increasing throughout the experiment) to ensure that no reuse acid remains in the tubing between the reactor and Valve 839. This clears the waste tubing before fresh acid flows through the column and pumps back to the reuse acid bottle in the subsequent fresh acid deblocking step.

Fresh deblocking: Turn valve 808 to A, valve 807 to B, and close valve 824. Charge 5-7 mL of the fresh deblocking solution into the acid feed zone, then push it into the reactor with nitrogen pressure for 6 seconds. Open valve 824. The outlet valves to waste (valves 809 and 810) are closed. Open the valve to waste (valve 810) and pump the deblocking solution through the resin bed with Pump 9 4 mL/min. In parallel to Pump 9 pumping, open valve 814 and start Pump 1 feeding the deblocking solution at 30 mL/min until 2-11 mL has been pumped (Pump 1 finishing before Pump 9). Liquid pumping into the acid feed zone from Pump 1 simultaneously flows into the reactor to maintain liquid level above the resin bed and keep the flow going for the entire duration of run time for pump 9. Extra pumping time is used to clear all the lines from the reactor to the reuse acid feed bottle so that the entire volume of fresh acid can be used in the ensuing reuse acid step of the following cycle.

Perform the following ACN wash procedure 4 times. Open waste valve 809, charge ACN (4 mL) into the feed zone, then close valve 809 and push it into the reactor with nitrogen pressure for 2 seconds. Open the valve to waste (valve 810) and pump the ACN wash through the resin bed with Pump 9 at a rate of 10 mL per minute until the wash is through the resin. This is a large reduction in ACN wash solvent compared to examples 1, 2, and 4, which use the same synthesizer. During the first cycle only, additional fluidized washes are incorporated between plug flow washing steps.

Coupling Reaction: After deblocking wash, the next sequential phosphoramidite is coupled, installed in sequential steps from 3' to 5'. For each phosphoramidite to be coupled in the sequence, perform the coupling reaction procedure essentially as described as follows, using the amidite solution corresponding to the nucleotide in the sequence. Turn valve 808 to B. Pre-wash the amidite zone and flow path to the reactor twice, each time by pumping 4 mL ACN into the amidite feed zone with valve 809 closed, then open valve 810 and pump to waste for 15 seconds at a rate of 10 mL/min. Pump first the activator solution (2 mL, 10 equiv., Table 1), and then the appropriate amidite solution (2 mL, 2.0 equiv.) into the feed zone. Close valve 809 and open valves 855, 824, and 838 for 3 seconds to mix the amidite and activator solution with bubbling nitrogen. Close valves 855, 824 and 838. Push the mixture in the feed zone into the reactor with nitrogen pressure for 6 seconds by opening valve 845, then open valve 824 and continue nitrogen pressure for 8 seconds. With the amidite and activator solutions mixed with the resin, continuously fluidize the bed as follows with valve 824 open and valve 809 closed: apply nitrogen pressure to the top of the reactor for 3 seconds. Vent the pressure from the top of the reactor for 15 seconds, while at the same time opening valve 838, causing nitrogen bubbling to agitate and fluidize the resin bed with the reagent solutions. Repeat this process continually for 10 min (15 min for the fluoro amidites and the mA at cycle 16), then open valve 809 and apply nitrogen pressure for 8 seconds to the top of the reactor, draining liquid from the bottom of the reactor to waste. Pump ACN (4 mL) into the amidite feed zone and push it through the reactor with nitrogen pressure for 15 seconds. Repeat this wash once. This is a large reduction in ACN wash solvent compared to examples 1, 2, and 4, which use the same synthesizer. Furthermore, the larger version of the reactor (Examples 8, 9, and 10) uses a spray ball and even less ACN mL/mmol.

Oxidation reaction (when required instead of Sulfurization): After the coupling reaction wash, perform the oxidation reaction essentially as described as follows. Turn valves 806, 807, and 808 to A, and open valves 824, 809, and 853. Pump oxidation solution (Table 19, 4.2 mL for cycles 3&4, 5.3 mL for cycles 5-18) into the feed zone, close valve 809, and push the iodine solution into the reactor with nitrogen pressure for 10 seconds. Fluidize the reactor bed 11 times as follows: pressurize the top of the reactor with nitrogen pressure for 5 seconds. Vent the pressure from the top of the reactor for 15 seconds, while at the same time opening valve 838, causing nitrogen bubbling to agitate and fluidize the resin bed with the reagent solution. Open valve 810 and pump 5.3 mL of liquid volume with pump 9 over 30 seconds, then close valve 810. Open valve 843 and valve 809 to push any remaining reagent out of the reactor. Close valve 843 and open valve 853.

Perform the following ACN wash procedure 4 times. This is a large reduction in ACN wash solvent compared to examples 1, 2, and 4, which use the same synthesizer. Open waste valve 809, charge ACN (4 mL) into the iodine feed zone, then close valve 809 and push it into the reactor with nitrogen pressure for 2 seconds. Open the valve to waste (valve 810) and pump the ACN wash through the resin bed with Pump 9 at a rate of 10 mL per minute until the wash is through the resin.

Sulfurization (thiolation) reaction (when required instead of Oxidation): After the coupling reaction wash, perform the thiolation reaction essentially as described as follows. Turn valve 806 to B, valves 805, 807, and 808 to A, and open valves 824 and 809. Pump sulfurization solution (Table 19, 6.5 mL) into the feed zone, close valve 809, and push it into the reactor with nitrogen pressure for 6 seconds. Fluidize the reactor bed 22 times as follows: pressurize the top of the reactor with nitrogen pressure for 3 seconds. Vent the pressure from the top of the reactor for 15 seconds, while at the same time opening valve 838, causing nitrogen bubbling to agitate and fluidize the resin bed with the reagent solutions. Open valve 810 and pump 6.5 mL of liquid volume with Pump 9 over 30 seconds, then close valve 810. Wash as described above for the oxidation reaction, but the ACN comes into the reactor through the sulfurization feed zone.

Capping reaction: After the oxidation (or sulfurization) reaction wash, perform the capping reaction essentially as described as follows. Turn valves 805 and 806 to B, and valves 807 and 808 to A. Open valves 824 and 809. Simultaneously pump capping solution A and capping solution B, 1.75 mL each, into the feed zone and then close valve 809. Push the liquid into the reactor with nitrogen pressure for 6 seconds. Fluidize the reactor bed 3 times as follows: pressurize the top of the reactor with nitrogen pressure for 5 seconds. Vent the pressure from the top of the reactor for 15 seconds, while at the same time opening valve 838, causing nitrogen bubbling to agitate and fluidize the resin bed with the reagent solutions. Open valve 810 and pump 3.5 mL of liquid volume with Pump 9 over 35 seconds, then close valve 810. Wash as described above for the oxidation reaction, but the ACN comes into the reactor through the capping feed zone.

Perform the following ACN wash procedure 1 time. Open waste valve 809, charge ACN (4 mL) into the capping feed zone, then close valve 809 and push it into the reactor with nitrogen pressure for 2 seconds. Open the valve to waste (valve 810) and pump the ACN wash through the resin bed with Pump 9 at a rate of 3 mL per minute until the wash is through the resin.

The very last cycle uses a sulfurization step and then an ACN wash. After this, wash the resin with DEA solution (20% V/V in ACN) for 10 minutes. Set valve 808 to the open position (B), and open valves 815 and 824. Charge 9.3 mL of DEA into the feed zone using Pump 4. Fluidize 4 times, then open valve 810 and turn on Pump 9 for 60 seconds, pumping the DEA to waste at a rate of 8 mL per minute.

Repeat these steps 3 more times to do a total of four DEA washes. Wash 3 times with 4 mL of ACN through the amidite feed zone, followed by 2 fluidized washes with 12 mL of ACN.

Resin bed height throughout the experiment was as shown in Table 21.

TABLE 21

Resin bed height increases from beginning to end of synthesis for example 7.

| cycle | amidite | Resin bed height ACN wet at the start of the cycle (cm) | Resin bed height Toluene wet after deblocking (cm) |
|---|---|---|---|
| 1 | MGS | 4.3 | 7.1 |
| 2 | MAS | 5.1 | 7.7 |
| 3 | MG | 5.9 | 7.9 |
| 4 | MU | 6.3 | 8.1 |
| 5 | MU | 6.9 | 8.2 |
| 6 | MU | 6.8 | 8.4 |
| 7 | MU | 7.2 | 8.7 |
| 8 | FA | 7.4 | 8.9 |
| 9 | MC | 8 | 9.1 |
| 10 | MC | 8.1 | 9.5 |
| 11 | MU | 8.6 | 9.9 |
| 12 | FU | 8.9 | 9.9 |
| 13 | MC | 9 | 10 |
| 14 | MC | 9.3 | 10.1 |
| 15 | FA | 9.7 | 10.5 |
| 16 | MA | 10 | 10.9 |
| 17 | FU | 9.9 | 11.1 |
| 18 | FA | 10.2 | 11.4 |
| 19 | FUS | 10.8 | 11.7 |
| 20 | FGS | 11 | 11.9 |
| 21 | MEMOPS | 11 | 12 |

Dry with nitrogen blowing down through the resin bed for 120 minutes. Final mass was 1.220 gram of dry resin. This corresponds to 0.817 gram of weight gain, or 8.13 g/mmol. OD/umol is listed in Table 17. Cleavage and deprotection were performed on a 22.8 mg sample of the dried resin with oligonucleotide. To do this, the resin was added to an UPLC vial with 0.5 mL of ammonium hydroxide. The vial was placed on a shaker for cleavage and deprotection (55 degrees C. for 5 hours). After the allotted time, the vial was removed and allowed to cool to room temperature. The sample was placed in a 1.5 mL centrifuge tube containing a filter basket and centrifuged for 30 seconds to 1 minute. 1.5 mL of Milli Q water was added to another UPLC vial, and 50 uL of the sample liquid (containing the oligonucleotide) was added. The spent resin was discarded. The UPLC tube was inverted repeatedly to mix the sample, then placed in the UPLC. UPLC shows the cleaved and deprotected oligonucleotide product is 79.92% pure by peak area percent, as shown in Table 17, UPLC results for examples 6 through 10 and comparison to Cytiva AKTA. LCMS analysis confirmed that the main product peak represents the correct strand. There was only one significant truncation (>1% area) observed, a peak of 2.02% area corresponding to incomplete coupling of the final amidite MeMOP. Due to the high purity and yield, these results indicate that an ACN wash followed by reuse acid is an acceptable wash method after capping, and that removal of the fluidized washes is not detrimental compared to examples 2 and 4. Total fresh acid used was 263 mL as calculated from the feed bottle mass before and after, therefore about 2630 mL/mmol. This is 29.2% of the Cytiva AKTA typical amount, which is typically about 9000 mL/mmol.

Example 8—Preparation of AngPTL3 Antisense Strand at 10 Mmol Scale in 4" i.d. Reactor A single antisense strand of AngPTL3 was synthesized at pilot scale in a fluidized bed reactor. (This is the same sequence shown in FIG. 10). 5' MeMOP*fG*fU*fAfUmA fAmCmC fUmUmC mCfAmUmUmUmUmGmA*mG*mG3

The synthesis of this molecule using the fluidized bed method of the current invention is herein described, and comprises deblocking, coupling, oxidizing (or sulfurization), and capping steps to sequentially install the remaining phosphoramidites. One of the main differences in this example is that it is done at larger scale (10 mmol) and in a larger fluid bed reactor that is the same diameter from bottom to top, 10.16 cm inside diameter and 61 cm tall. The reactor has a filter frit flat bottom. In this larger diameter reactor, the fluidization is sufficient without the wider funnel zone at the top. The larger the reactor diameter, the less the wall effects, so the easier it is to completely fluidize and redistribute solids and liquid without an upper wide diameter section. The fluidization at the start of each reaction step typically only expands the height of the slurry in the reactor by about 2-4 cm. The apparatus for this synthesis is shown in FIG. 9. Another difference in this example is that it uses toluene for washing prior to deblocking. Also, like example 6, example 8 has integrated solvent re-use from one phosphoramidite cycle to the next, which reduces solvent wash volumes. The cleaner washes after deblock are pumped into a re-use ACN vessel, and it is used in the first portion of washes after deblock on the next phosphoramidite cycle. Table 31 is a guide to the various embodiments in the fluid bed reactor examples.

Resin bed height reaches 5 cm ACN solvent wet and 4 cm dry by the end of the experiment. Maximum resin bed height of 6 cm is reached during downflow portions of the final deblocking step. Maximum pressure drop across the resin bed is 15 psig during the experiment, because that is the pressure of the supply nitrogen used to push liquid through the resin bed. Two equivalents of amidite are used for the couplings, like in Examples 6 and 7. Overall synthesis conditions are given in Table 22.

TABLE 22

Synthesis conditions for example 8.

| Item | Value | Unit |
|---|---|---|
| Resin loading | 247 | μmol/gram |
| Resin starting amount | 40.50 | gram |
| Synthesis scale | 10 | mmol |
| Deblocking solution 3% DCA, amount per cycle | 3100 (bases 1 to 5)<br>3300 (bases 6 to 10)<br>3500 (bases 11 to 21) | mL |
| Deblocking reaction time | 8 (bases 1 to 5)<br>9 (bases 6 to 10)<br>10 (bases 11 to 21) | min |
| Amidite concentration | 0.1 | M in ACN |
| Amidite equivalence | 2 | eq |
| Activator concentration | 0.5 | M in ACN |
| Activator equivalence | 10 | eq |
| Amidite solution, amount per cycle | 200 | mL |
| Activator solution, amount per cycle | 200 | mL |
| Coupling reaction time | 15 (bases 8, 12, 15 to 21)<br>10 (all other bases) | min |

TABLE 22-continued

| Synthesis conditions for example 8. | | |
|---|---|---|
| Item | Value | Unit |
| Iodine equivalence | 2.1 (bases 3 to 4)<br>2.65 (bases 5 to 18) | eq |
| Oxidation solution, amount per cycle | 420 (bases 3 to 4)<br>530 (bases 5 to 18) | mL |
| Oxidization time | 5 | min |
| Sulfurization equivalence | 13 | eq |
| Sulfurization solution, amount per cycle | 650 | mL |
| Sulfurization time | 10 | min |
| Capping solution A, amount per cycle | 350 | mL |
| Capping solution B, amount per cycle | 350 | mL |
| Capping time | 4 | min |

Begin with mG coupled onto NittoPhase HL 2' OMeG (iBu) 250 resin (247 μmol/g) using known methods (herein referred to as "mG-resin"), and refer to FIG. 9 for the setup of the synthesizer apparatus. Use ACN to slurry 40.50 g (10.0 mmol) of the mG-resin into a 10.16 cm inside diameter reactor with a 40 micron sintered mesh filter frit at the bottom. The initial resin depth is about 1 cm tall.

Prepare the reagent solutions as follows:

All amidite solutions were prepared with ACN from Fisher Lot #212215. Dissolve amidites into ACN solvent as follows. Mixed until in solution. Add molecular sieve dry packs to sealed bottle.

| Amidites needed: | | Solvent required: |
|---|---|---|
| mA | 50.79 g | 572 mL |
| mC | 81.15 g | 1012 mL |
| mG | 49.76 g | 572 mL |
| mU | 93.73 g | 1232 mL |
| fA | 69.37 g | 792 mL |
| fG | 30.20 g | 352 mL |
| fU | 59.30 g | 792 mL |
| MeMOP, 19.59 g | | 352 mL |

Cap B1:
- Acetic Anhydride: Macron Fine Chemicals Lot #0000239131
- Acetonitrile: Fisher Lot #206496
- Charged 1657 mL of Acetic Anhydride and 2486 mL of ACN to feed vessel.

Cap B2:
- 2,6—Lutidine: Acros Lot #A0428332
- Acetonitrile: Fisher Lot #206496
- Charged 2486 mL of Lutidine and 1657 mL of ACN to feed vessel.

Cap A:
- 1-Methylimidazole: Acros Lot #A0425789
- ACN: Fisher Lot #206496
- Charged 1657 mL of Imidazole. Charged 6628 mL of ACN.

0.2M Xanthane Hydride Sulfurization Solution:
- Xanthane Hydride: TCI Lot #QLXKC-RI
- Pyridine: Fishers Lot #208059
- Charged 3775 mL of Pyridine. Charged 114 g of XH to Pyridine bottle. Mixed until in solution.

Oxidation Solution:
- Iodine solution (0.05M)
- Honeywell Lot #EA702-US
- Charged 10Kg of keg stock to feed can.

Activator Solution:
- Honeywell Lot #EA952-US
- Charged 5 Kg of keg stock solution to feed can.

3% DCA in Toluene Solution:
- DCA: Supelco Lot #61069116
- Toluene: Superior Lot #FH11313266
- Lot #1
  1. Charged 18,201 mL of Toluene to a carboy
  2. Charged 563 mL of DCA to carboy
  3. Charged carboy to feed can
- Lot #2
  1. Charged 18,428 mL of Toluene to a carboy
  2. Charged 570 mL of DCA to carboy
  3. Charged carboy to feed can
- Lot #3
  1. Charged 18,483 mL of Toluene to a carboy
  2. Charged 572 mL of DCA to carboy
  3. Charged carboy to feed can
- Lot #4
  1. Charged 18,575 mL of Toluene to a carboy
  2. Charged 575 mL of DCA to carboy
  3. Charged carboy to feed can Prime all pumps and feed lines. ACN was passed over a bed of molecular sieves on the way into an inerted feed can. ACN, toluene, and DCA in toluene are fed from feed cans via pressure push and controlled with automated flow control valves. All other feeds use peristaltic pumps and feed vessels. The amidite solutions are contained separately in feed vessels labeled "AM. 1 L" and connected to peristaltic pumps attached to valves V901A through V908A in FIG. 9. The MeMOP phosphoramidite used one of the AM. feed vessels. The activator and DEA solutions are contained feed vessels labeled "Activ. 5 gal" and "DEA," respectively in FIG. 9.

For each phosphoramidite added in the synthesis, perform the deblocking, coupling, oxidizing (or sulfurization where there is a P=S linkage in the sequence), and capping steps sequentially as described below. Capping is not needed after cycle 21 MeMOP phosphoramidite is added.

During the coupling, oxidation, sulfurization, and capping reactions, the fluidization continued its on/off cycle for the majority of the designated reaction time. It should be noted that the fluidization does not need to be done with an on/off cycle.

Fluidization can be bubbling the entire time without the up and downs push. The procedure is a carry-over from the research scale experiments. At research scale, in the small diameter reactor, there is some benefit in pushing up and down during fluidization, because it helps to get all the resin beads initially wetted and fluidized, after which time the up and down pushing does not provide further benefit. At larger diameters, for example this 4-inch diameter reactor, the up/down pushing via the on/off cycle is not needed.

During the deprotection reaction, the resin bed fluidized with 200-250 mL of DCA solution at the beginning, and then the deprotection reaction continued to the end plug flow reaction style without fluidization. The fluidization is done by blowing nitrogen gas up through the bottom filter screen by opening either valve 956 or 958 (V956, V958) and valve 953 the same time the feed zone vent valve opens (V952). When this procedure states that liquid is pumped down through the resin bed, it means that the waste pump at the outlet of the reactor bottom runs at a target setpoint, while nitrogen pressure pushes on top of the resin bed to push the liquid down through. The purpose of the peristaltic pump is to meter the liquid flow through the bed at a controlled rate.

Toluene wash: Charge toluene (300 mL) into the feed zone. Chase the toluene into the feed zone with nitrogen to clear the feed tubing. Push the toluene into the reactor. Fluidize the resin bed 4 times for 2 seconds each to achieve complete liquid-solid contacting, swell the resin beads, and re-set the resin bed. Start the waste pump and apply nitrogen pressure on top of the feed zone with valve 951 so that toluene starts flowing down through the resin bed and out the bottom of the reactor. Charge 200 mL more toluene to the feed zone, which flows into the top of the reactor the same time that toluene is pumped out the bottom. The outlet pump rate is set so that it takes 2 minutes to pump out 500 mL toluene. Any residual wash solvent is pushed to waste out the filter bottom.

Deblocking reaction: Charge deblocking solution (Table 22, 200 mL) into the feed zone. Chase the deblocking solution into the feed zone with nitrogen to clear the feed tubing. Push the deblocking solution into the reactor. Fluidize the resin bed for 7 seconds to achieve complete liquid-solid contacting and re-set the resin bed. Start the waste pump and apply nitrogen pressure on top of the feed zone with valve 951 so that the DCA solution starts flowing down through the resin bed and out the bottom of the reactor. Simultaneously feed more DCA solution to the feed zone, which flows into the top of the reactor the same time that it is pumped out the bottom. Pumping out of the deblock solution starts 5-30 seconds before the start of the second feed. The time is adjustable. The goal is to pump out until the deblock solution liquid level is just above the top of the resin bed when the fresh deblock solution starts to flow into the reactor, so that there is less back-mixing above the resin bed. The outlet pump rate is set to achieve total pump out in the desired reaction times stated in Table 22. The deblock solution is added to the reactor at about the same rate that it is pumping out by setting % open for the feed control valve. Any residual solution is pushed to waste out the filter bottom.

Wash #1: Charge ACN solvent into feed zone through the acid feed line (200 mL). Chase wash solvent into feed zone with nitrogen to clear the feed tubing. Push solvent into the resin bed reactor. Solvent sprays the walls of the reactor when it enters. Fluidize one time for 5 seconds. Push out reactor to waste.

Wash #2,3,4,5: Charge ACN solvent, from the ACN re-use can, into feed zone through solvent feed line (200 mL). Chase wash solvent into feed zone with nitrogen to clear the feed tubing. Push the solvent into the reactor via spray cone to enable even distribution of the solvent without disrupting the resin bed. Pump the ACN solvent through the resin bed at 300 mL/min. Push residual ACN solvent to waste out the filter bottom. Repeat the same wash 3 more times.

Wash #6,7,8: Charge fresh ACN solvent into feed zone (200 mL). Chase wash solvent into feed zone with nitrogen to clear the feed tubing. Push the solvent into the reactor via spray cone to enable even distribution of the solvent without disrupting the resin bed. Pump the ACN solvent through the resin bed at 300 mL/min. Push residual ACN solvent out the filter bottom to the reuse ACN can. Repeat the same wash 2 more times.

Wash #9: Charge ACN solvent into feed zone (200 mL). Chase wash solvent into feed zone with nitrogen to clear the feed tubing. Push solvent into the resin bed reactor. Solvent sprays the walls of the reactor when it enters. Fluidize one time for 5 seconds. Push ACN solvent out the filter bottom to the reuse ACN can.

Coupling reaction: Pump the specified amidite (200 mL) into the amidite activation zone and chase it in with nitrogen. Pump the activator solution (200 mL) into the amidite activation zone and chase in with nitrogen. Mix the two together by bubbling nitrogen into the bottom of the amidite zone for about 2 seconds. Push this mixture into the feed zone, and then into the reactor to start the coupling reaction on the resin. Fluidize the resin reactor intermittently throughout the coupling time (10 minutes or 15 minutes), about once every 45 seconds, bubbling with nitrogen into the bottom of the resin reactor for 15 seconds each time. Constant fluidization for the entire reaction time is also acceptable rather than intermittent. Push the coupling solution to waste out the filter bottom after the reaction time.

Solvent Wash: Charge ACN solvent into the amidite activation zone (200 mL) through the amidite feed tube to chase any residual drops out of the inlet tubing, then push it to the feed zone, then push into the resin reactor. Solvent sprays on walls when entering reactor. Push through reactor to waste without fluidizing.

Oxidation reaction (when required instead of Sulfurization): Charge ACN (200 mL) into the amidite activator mixing zone so that it is ready to wash the resin immediately at the end of the oxidation reaction. Solvent enters the amidite activator mixing zone through a spray ball to wash all the walls. Charge 0.05 M iodine solution (530 mL) into the feed zone, chasing it with nitrogen to clear the feed tubing. Push the solution into the reactor to start the oxidation reaction on the resin. Fluidize the resin reactor intermittently throughout the oxidation time (~4 minutes), about once every 30 seconds, bubbling with nitrogen into the bottom of the resin reactor for 12 seconds each time. Constant fluidization for the entire reaction time is also acceptable rather than intermittent. Start pumping the oxidation solution out through the resin bed at 540 mL/min for 65 seconds. Push the residual oxidation solution to waste out of the filter bottom.

Wash #1: Push the 200 mL ACN wash solvent (from the amidite activator mixing zone) into the feed zone, and then push it into the reactor to wash the resin. Solvent enters the reactor through the cone spray onto the resin, to evenly spray on top of the resin bed and keep the resin bed flat, which makes the plug flow wash more efficient. Pump the ACN solvent through the resin bed at 300 mL/min. Push residual ACN solvent out the filter bottom to waste.

Wash #2: Charge ACN (200 mL) into feed zone through the oxidation solution feed line, chasing it with nitrogen to clear the feed tubing. Push the solvent into reactor. Solvent sprays on walls when entering reactor. Pump the ACN solvent through the resin bed at 300 mL/min. Push residual ACN solvent out the filter bottom to waste.

Wash #3,4,5: Charge ACN solvent into feed zone (200 mL). Chase wash solvent into feed zone with nitrogen to clear the feed tubing. Push the solvent into the reactor via spray cone to enable even distribution of the solvent without disrupting the resin bed. Pump the ACN solvent through the resin bed at 300 mL/min. Push residual ACN solvent out the filter bottom to waste. Repeat the same wash 2 more times.

Wash #6: Charge ACN solvent into feed zone (200 mL). Chase wash solvent into feed zone with nitrogen to clear the feed tubing. Push solvent into the resin bed reactor. Solvent sprays the walls of the reactor when it enters. Fluidize one time for 5 seconds. Push ACN solvent out the filter bottom to waste.

Sulfurization (thiolation) reaction (when required instead of Oxidation): Charge ACN (200 mL) into the amidite activator mixing zone so that it is ready to wash the resin immediately at the end of the sulfurization reaction. Charge 0.2 M xanthane hydride solution (650 mL) into the feed zone, chasing it with nitrogen to clear the feed tubing. Push the solution into the reactor to start the sulfurization reaction on the resin. Fluidize the resin reactor intermittently throughout the oxidation time (~8 minutes), about once every 30 seconds, bubbling with nitrogen into the bottom of the resin reactor for 12 seconds each time. Constant fluidization for the entire reaction time is also acceptable rather than intermittent. Start pumping the xanthane hydride solution out through the resin bed at a pump setpoint of 700 mL/min for 60 seconds. Push the residual xanthane hydride solution to waste out of the filter bottom.

Wash #1: Push the 200 mL ACN wash solvent (from the amidite activator mixing zone) into the reactor to wash the resin. Solvent enters the reactor through the cone spray onto the resin. Pump the ACN solvent through the resin bed at 300 mL/min. Push residual ACN solvent out the filter bottom to waste.

Wash #2: Charge ACN (200 mL) into feed zone through the xanthane hydride solution feed line, chasing it with nitrogen to clear the feed tubing. Push the solvent into reactor. Solvent sprays on walls when entering reactor. Pump the ACN solvent through the resin bed at 300 mL/min. Push residual ACN solvent out the filter bottom to waste.

Wash #3,4,5: Charge ACN solvent into feed zone (200 mL). Chase wash solvent into feed zone with nitrogen to clear the feed tubing. Push the solvent into the reactor via spray cone to enable even distribution of the solvent without disrupting the resin bed. Pump the ACN solvent through the resin bed at 300 mL/min. Push residual ACN solvent out the filter bottom to waste. Repeat the same wash 2 more times.

Wash #6: Charge ACN solvent into feed zone (200 mL). Chase wash solvent into feed zone with nitrogen to clear the feed tubing. Push solvent into the resin bed reactor. Solvent sprays the walls of the reactor when it enters. Fluidize one time for 5 seconds. Push ACN solvent out the filter bottom to waste.

Capping reaction: Charge capping solution A and capping solution B (350 mL each) into the feed zone, chasing them with nitrogen to clear the feed tubing. Push the solution into the reactor to start the capping reaction on the resin. Fluidize the resin reactor 2 times, bubbling with nitrogen into the bottom of the resin reactor for 12 seconds each time. Total time for both fluidizations is about 1 minute. Start pumping the reaction solution out through the resin bed at 400 mL/min for 70 seconds. Push the residual reaction solution to waste out of the filter bottom.

Wash #1,2: Charge ACN (100 mL) into feed zone through the capping A solution feed line, chasing it with nitrogen to clear the feed tubing, and charge ACN (100 mL) into feed zone through the capping B solution feed line, chasing it with nitrogen to clear the feed tubing. Push the solvent into reactor. Solvent sprays on walls when entering reactor. Pump the ACN solvent through the resin bed at 300 mL/min. Push residual ACN solvent out the filter bottom to waste. Repeat the same wash 1 more time.

Wash #3,4: Charge ACN solvent into feed zone (200 mL). Chase wash solvent into feed zone with nitrogen to clear the feed tubing. Push the solvent into the reactor via spray cone to enable even distribution of the solvent without disrupting the resin bed. Pump the ACN solvent through the resin bed at 300 mL/min. Push residual ACN solvent out the filter bottom to waste. Repeat the same wash 1 more time.

Wash #5: Charge ACN solvent into feed zone (200 mL). Chase wash solvent into feed zone with nitrogen to clear the feed tubing. Push solvent into the resin bed reactor. Solvent sprays the walls of the reactor when it enters. Fluidize one time for 5 seconds. Push ACN solvent out the filter bottom to waste.

Timing: The overall timing of a typical complete amidite cycle was as following, starting at 9:22 a.m.:

- 9:22 a.m. toluene wash fluidize four times,
- 9:28 acid reagent solution in, fluidization one time,
- 9:35 acid reagent solution out,
- 9:37 fluidized wash, solvent sprays on walls when entering reactor
- 9:39 plug flow wash with re-use ACN, solvent enters the reactor through the cone spray onto the resin
- 9:41 plug flow wash with re-use ACN, solvent enters the reactor through the cone spray onto the resin,
- 9:43 plug flow wash with re-use ACN, solvent enters the reactor through the cone spray onto the resin,
- 9:44 plug flow wash with re-use ACN, solvent enters the reactor through the cone spray onto the resin,
- 9:46 plug flow wash, solvent enters the reactor through the cone spray onto the resin,
- 9:48 plug flow wash, solvent enters the reactor through the cone spray onto the resin,
- 9:50 plug flow wash, solvent enters the reactor through the cone spray onto the resin,
- 9:52 fluidized wash, solvent sprays on walls when entering reactor,
- 9:57 coupling reagent solution in,
- 10:14 coupling reagent solution out,
- 10:16 plug flow wash, solvent sprays on walls when entering reactor
- 10:21 XH reagent solution in,
- 10:30 XH reagent solution out,
- 10:32 plug flow wash, solvent enters the reactor through the cone spray onto the resin,
- 10:35 plug flow wash, solvent sprays on walls when entering reactor,
- 10:37 plug flow wash, solvent enters the reactor through the cone spray onto the resin,
- 10:39 plug flow wash, solvent enters the reactor through the cone spray onto the resin,
- 10:41 plug flow wash, solvent enters the reactor through the cone spray onto the resin,
- 10:43 fluidized wash, solvent sprays on walls when entering reactor,
- 10:48 capping reagent solution in,
- 10:52 capping reagent solution out,
- 10:54 fluidized wash, solvent sprays on walls when entering reactor,
- 10:56 fluidized wash, solvent sprays on walls when entering reactor,
- 10:59 plug flow wash, solvent enters the reactor through the cone spray onto the resin,
- 11:01 plug flow wash, solvent enters the reactor through the cone spray onto the resin,
- 11:03 fluidized wash, solvent sprays on walls when entering reactor
- The process was run on 4 consecutive days, with 5, 5, 6, and 5 amidite cycles per day.
- Resin was held in the reactor overnight submerged in ACN and under nitrogen each night.

Final cycle: The final amidite (MeMOP) does not have a DMT protecting group at the 5' position, so it does not need a final deblocking. After the final MeMOP coupling, wash, sulfurization, and wash are complete, wash with DEA solution. Charge DEA solution (500 mL) into the feed zone. Chase the DEA solution into the feed zone with nitrogen to clear the feed tubing. Push the solution into the reactor.

Fluidize the resin bed two times to achieve complete liquid-solid contacting and re-set the resin bed. Total time for both fluidizations is about 1 minute. Start pumping the DEA solution through the resin bed at 100 mL/min for 600 seconds. Simultaneously pump more DEA solution (500 mL) into the feed zone in parallel, so that it enters the top of the reactor at about the same rate that it is pumping out. Chase the DEA solution into the feed zone with nitrogen to clear the feed tubing. A total of 1 L pumps through the resin bed during the 600 seconds. Push the residual DEA solution to waste out of the filter bottom. Repeat this DEA treatment one more time.

Wash #1,2: Charge ACN solvent into feed zone (200 mL). Chase wash solvent into feed zone with nitrogen to clear the feed tubing. Push the solvent into the reactor via spray cone to enable even distribution of the solvent without disrupting the resin bed. Pump the ACN solvent through the resin bed at 300 mL/min. Push residual ACN solvent out the filter bottom to waste. Repeat the same wash 1 more time.

Wash #3: Charge ACN solvent into feed zone (200 mL). Chase wash solvent into feed zone with nitrogen to clear the feed tubing. Push solvent into the resin bed reactor. Solvent sprays the walls of the reactor when it enters. Fluidize one time for 5 seconds. Push ACN solvent out the filter bottom to waste.

Wash #4,5: Charge ACN solvent into feed zone (200 mL). Chase wash solvent into feed zone with nitrogen to clear the feed tubing. Push the solvent into the reactor via spray cone to enable even distribution of the solvent without disrupting the resin bed. Pump the ACN solvent through the resin bed at 300 mL/min. Push residual ACN solvent out the filter bottom to waste. Repeat the same wash 1 more time.

Wash #6: Charge ACN solvent into feed zone (200 mL). Chase wash solvent into feed zone with nitrogen to clear the feed tubing. Push solvent into the resin bed reactor. Solvent sprays the walls of the reactor when it enters. Fluidize one time for 5 seconds. Push ACN solvent out the filter bottom to waste.

Drying: Slurry the resin out of the reactor. Filter it on a laboratory filter. Dry with nitrogen blowing down through the resin bed for 5-6 hours. 2.5 g of resin bound material was removed for samples, which includes 2 g washed from the reactor and 0.5 g from the bulk after drying. Crude mass gain was 7.99 g/mmol including samples.

Do bulk cleavage and deprotection (C/D) on about half of the resin bound crude product at a time. C/D was accomplished by combining the resin with 28% aq. ammonium hydroxide (30 mL/g of resin) and heating to 38° C. in a sealed vessel for 18-20 h. To the 1.85 L Ace-thread pressure vessel equipped with pressure gauge, 25 psig pressure relief safety valve, thermocouple, heating mantle and magnetic stir bar was charged ANGPTL3 AS protected (56.1 g, 6.798 mmol) and AMMONIUM HYDROXIDE (28 mass %) in WATER (1.68 L, 2000 g, 10000 mmol). The thin slurry was sealed and stirred while heating to 38° C. overnight.

After 18 hours at 38° C., turn off heat and add an ice water bath to cool the reactor to less than room temperature. The resin was allowed to settle and weighed aliquot of the supernatant liquid was diluted into a weighed amount of mill-Q water.

mass of aliquot=0.1754 g mass of milli-Q water=20.2768 g

Once C/D is complete, proceed with workup of bulk reaction mixture.

Filter the bulk solution to remove the spent resin. Wash the spent resin with 3×150 mL of 1:1 EtOH:H2O. Combine the filtrate and the washes and concentrate on the rotavapor (40° C. bath) to remove as most of the ammonia. Repeat the same procedure for the second half of the resin bound material. UPLC results showed 75.3% FLP for a sample from the first half and 78.9% for a sample from the first half. Details can be seen in Table 17, UPLC results for examples 6 through 10 and comparison to Cytiva AKTA. OD/umol was determined, as recorded in Table 23. Purity corrected crude yield was about 58% on the first half and 62% on the second half of the material. In comparison, the purity corrected crude yield was 57% in a previous 1 kg cGMP campaign.

TABLE 23

Summary of yield and purity for 10 mmol scale synthesis in example 8.

| | First half of batch from synthesizer | Second half of batch from synthesizer |
|---|---|---|
| scale | 5 mmol | 5 mmol |
| FLP % (homogenized sample) after crude ultrafiltration | 75.32% | 78.92% |
| OD/μmol | 155 | 157 |
| Crude % yield by OD | 77% | 78% |
| Purity corrected yield by OD | 58% | 62% |
| Mass product. | 27.04 g | 26.97 g |

The material was forward processed through chromatographic purification, which is beyond the scope of this document.

Example 9: Pilot Scale Fluid Bed Synthesizer with in-Process Integrated

Multi-Pass Washing.

A same antisense strand of AngPTL3 (FIG. 10) was synthesized in a modified version of the fluidized bed reactor system from Example 8.

5' MeMOP*fG*fU*fAfUmA fAmCmC fUmUmC mCfAmUmUmUmUmGmA*mG*mG3,

The synthesis of this molecule using the fluidized bed method of the current invention is herein described, and comprises deblocking, coupling, oxidizing (or sulfurization), and capping steps to sequentially install the remaining phosphoramidites. The main differences between example 8 and example 9 is that the system was modified to include in-process integrated multi-pass washing, and there was no capping for cycles 2 through 9 (phosphoramidites 3 through 10). Capping is not needed after cycle 21 MeMOP phosphoramidite is added.

Resin bed height reaches 5 cm acetonitrile solvent wet and 4 cm dry by the end of the experiment. Maximum resin bed height of 6 cm is reached during downflow portions of the final deblocking step. Maximum pressure drop across the resin bed is 15 psig during the experiment, because that is the pressure of the supply nitrogen used to push liquid through the resin bed. Two equivalents of amidite are used for the couplings, like in Examples 6, 7, and 8. Overall synthesis conditions are given in Table 24. Deblocking time and volume fresh DCA solution from beginning to end of synthesis are given in Table 25.

TABLE 24

| synthesis conditions for example 9. | | |
|---|---|---|
| Item | Value | Unit |
| Resin loading | 249 | μmol/gram |
| Resin starting amount | 40.30 | gram |
| Synthesis scale | 10 | mmol |
| Amidite concentration | 0.1 | Min acetonitrile |
| Amidite equivalence | 2 | eq |
| Activator concentration | 0.5 | Min acetonitrile |
| Activator equivalence | 10 | eq |
| Amidite solution, amount per cycle | 200 | mL |
| Activator solution, amount per cycle | 200 | mL |
| Coupling reaction time | 15 (cycles 8, 12, 15 to 21) 10 (all other cycles) | Min |
| Iodine equivalence | 2.1 (cycles 3 to 4) 2.65 (cycles 5 to 18) | Eq |
| Oxidation solution, amount per cycle | 420 (cycles 3 to 4) 530 (cycles 5 to 18) | mL |
| Oxidization time | 5 | Min |
| Sulfurization equivalence | 13 | Eq |
| Sulfurization solution, amount per cycle | 650 | mL |
| Sulfurization time | 10 | Min |
| Capping solution A, amount per cycle | 100 | mL |
| Capping solution B, amount per cycle | 100 | mL |
| Capping time | 4 | Min |

KF of ACN used for amidite solution preparation: 56 ppm water

TABLE 25

| Deblocking time and volume fresh DCA solution from beginning to end of synthesis for example 9. | | | |
|---|---|---|---|
| cycle | amidite | volume of 3% DCA solution (mL) | deblocking plug flow pumping time (minutes) |
| 1 | MGS | 1400 | 8.3 |
| 2 | MAS | 1500 | 8.3 |
| 3 | MG | 1570 | 8.3 |
| 4 | MU | 1640 | 8.3 |
| 5 | MU | 1710 | 9 |
| 6 | MU | 1780 | 9 |
| 7 | MU | 1850 | 9 |
| 8 | FA | 1920 | 9 |
| 9 | MC | 1990 | 9 |
| 10 | MC | 2060 | 9.7 |
| 11 | MU | 2130 | 9.7 |
| 12 | FU | 2200 | 9.7 |
| 13 | MC | 2270 | 9.7 |
| 14 | MC | 2340 | 9.7 |
| 15 | FA | 2410 | 9.7 |
| 16 | MA | 2480 | 9.7 |
| 17 | FU | 2550 | 9.7 |
| 18 | FA | 2620 | 9.7 |
| 19 | FUS | 2690 | 9.7 |
| 20 | FGS | 2760 | 9.7 |
| 21 | MEMOPS | 2830 | 9.7 |

Reagents and lot numbers used for Example 9 are shown in Table 26.

TABLE 26

| Reagent lots used for Example 9. | |
|---|---|
| Reagent | Lot |
| ACN | Fisher 214141 |
| Capping solution A, 1-Methylimidazole/ACN (20/80 v/v) | see below |
| Capping solution B, 1:1 Mixture B1 and B2. B1 is 40 vol % acetic anhydride in ACN. B2 is 60 vol % 2,6-lutidine in ACN | see below |
| 0.2M Xanthane hydride in ACN/pyridine (70/30 v/v) | see below |
| 0.05M Iodine in pyridine/water (90/10 v/v) | see below |
| Deblocking, Dichloroacetic acid (3% DCA/toluene v/v) | see below |
| DEA, 20% diethylamine in ACN (20/80 v/v) | see below |
| Activator reagent, 0.5M 5-(Ethylthio)-1H-tetrazole in ACN | DW336-US |
| Kinovate Nittophase HL 2'OMeG(iBu) 250, 249 umol/g | H08023 |

All amidite solutions were prepared with ACN from Fisher Lot #212215. Dissolve amidites into ACN solvent as follows. Mix until solution. Add molecular sieve dry packs to sealed bottle.

ACN lots used: EMD Lot #52261, EMD Lot #52261, Fisher #214141 Amidites needed: Solvent required:

| Amidites needed: | | Solvent required: |
|---|---|---|
| mA | 45.91 g | 517 mL |
| mC | 76.74 g | 957 mL |
| mG | 44.98 g | 517 mL |
| mU | 89.55 g | 1177 mL |
| fA | 64.56 g | 737 mL |
| fG | 25.48 g | 297 mL |
| fU | 55.19 g | 737 mL |
| MeMOP, 16.53 g | | 297 mL |

Amidite molecular weights were as follows:

mA DMT-2'-O-MeA(bz) phosphoramidite, MW 887.97 mC DMT-2'-O-MeC(Ac) phosphoramidite, MW 801.87 mG DMT-2'-O-MeG(iBu) phosphoramidite, MW 869.95 mU DMT-2'-O-MeU-CE phosphoramidite, MW 760.82 fA DMT-2'-F-dA(bz) phosphoramidite, MW 875.93 fC DMT-2'-F-dC(Ac) phosphoramidite, MW 789.84 fG DMT-2'-F-dG(iBu) phosphoramidite, MW 857.9 fU DMT-2'-F-dU-CE phosporamidite, MW 748.8

MeMOP, MW 556.5

Prepare the reagent solutions as follows:

Cap B1:

Acetic Anhydride: Macron Fine Chemicals Lot #0000239131

Acetonitrile: Fisher Lot #214141

Charge 481 mL of Acetic Anhydride and 722 mL of ACN to bottle.

Cap B2:

2,6—Lutidine: Acros Lot #A0428332

Acetonitrile: EMD Lot #52261

Charge 722 mL of Lutidine and 481 mL of ACN to bottle.

Cap A:

1-Methylimidazole: Alfa Aesar Lot #5009J24W

Acetonitrile: Fisher Lot #214141

Charge 481 mL of Imidazole. Charge 1924 mL of ACN.

0.2M Xanthane Hydride Sulfurization Solution:

Xanthane Hydride: TCI Lot #QLXKC-LI

Pyridine: Fishers Lot #208059

Charge 3775 mL of Pyridine. Charge 114 g of XH to Pyridine bottle. Mix until solution.

Oxidation Solution:

Iodine solution (0.05M)

Honeywell Lot #EA702-US

Charged ~9 Kg of keg stock to feed can.

Activator Solution:

Honeywell Lot #EA713-US

Charge ~5 Kg of keg stock solution to feed can.

20% DEA in Acetonitrile:

DEA: Sigma-Aldrich Lot #STBJ5069

Acetonitrile: Fisher Lot #214141

Charge 400 mL of DEA to bottle. Charge 1600 mL of ACN to bottle.

3% DCA in Toluene Solution:

DCA: Sigma Aldritch Lot #MKCQ92

Toluene: Superior Lot #HX11315122

Lot #1

1. Charged 19,240 mL of Toluene to a carboy
2. Charged 595 mL of DCA to carboy
3. Charged carboy to feed can Lot #2

1. Charged 20,311 mL of Toluene to a carboy
2. Charged 628 mL of DCA to carboy
3. Charged carboy to feed can Lot #3

1. Charged 12,272 mL of Toluene to a carboy
2. Charged 380 mL of DCA to carboy
3. Charged carboy to feed can Begin with mG coupled onto NittoPhase HL 2' OMeG (iBu) 250 resin (249 μmol/g) using known methods (herein referred to as "mG-resin"), and refer to FIG. 11 for the setup of the synthesizer apparatus. Use ACN to slurry 40.40 g (10.06 mmol) of the mG-resin into a 10.16 cm inside diameter reactor with a 40 micron sintered mesh filter frit at the bottom. The initial resin depth is about 1 cm tall.

Prime all pumps and feed lines. ACN is pushed through a bed of molecular sieves on the way into an inerted feed can. ACN and DCA in toluene are fed from feed cans via pressure push and controlled with automated flow control valves. All other feeds use peristaltic pumps and feed vessels. The amidite solutions are contained separately in feed vessels labeled "AM. 1 L" and connected to peristaltic pumps attached to valves V1101A through V1108A in FIG. 11. The MeMOP phosphoramidite used one of the AM. feed vessels. The activator and DEA solutions are contained in feed vessels labeled "Activ. 5 gal" and "DEA 1 L", respectively in FIG. 11.

For each phosphoramidite added in the synthesis, perform the deblocking, coupling, oxidizing (or sulfurization where there is a P=S linkage in the sequence), and capping steps sequentially as described below. There is no capping for cycles 2 through 9 (nucleosides 3 through 10). Capping is not needed after cycle 21 MeMOP is added.

During the coupling, oxidation, sulfurization, and capping reactions, the fluidization continued its on/off cycle for the majority of the designated reaction time. It should be noted that the fluidization does not need to be done with an on/off cycle. Fluidization can be bubbling the entire time without the up and downs push. The procedure is a carry-over from the research scale experiments. At research scale, in the small diameter reactor, there is some benefit in pushing up and down during fluidization, because it helps to get all the resin beads initially wetted and fluidized, after which time the up and down pushing does not provide further benefit. At larger diameters, for example this 4-inch diameter reactor, the up/down pushing via the on/off cycle is not needed.

As in previous examples, the fluidization is done by blowing nitrogen gas up through the bottom filter screen by opening either valve 1156 or 1158 (V1156, V1158, in FIG. 11.) the same time the feed zone vent valve opens (V1152, in FIG. 11).

Figure 12:
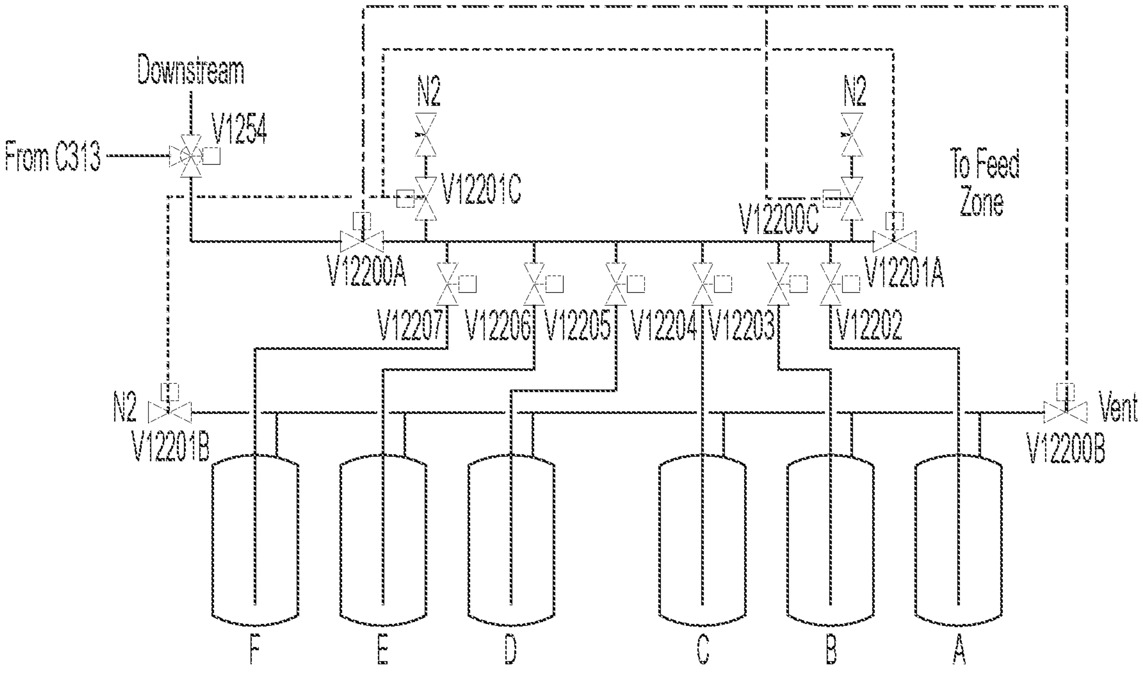
FIG. 12 is a schematic view of an in-process integrated multi-pass washing system for post deblock.
Figure 13:
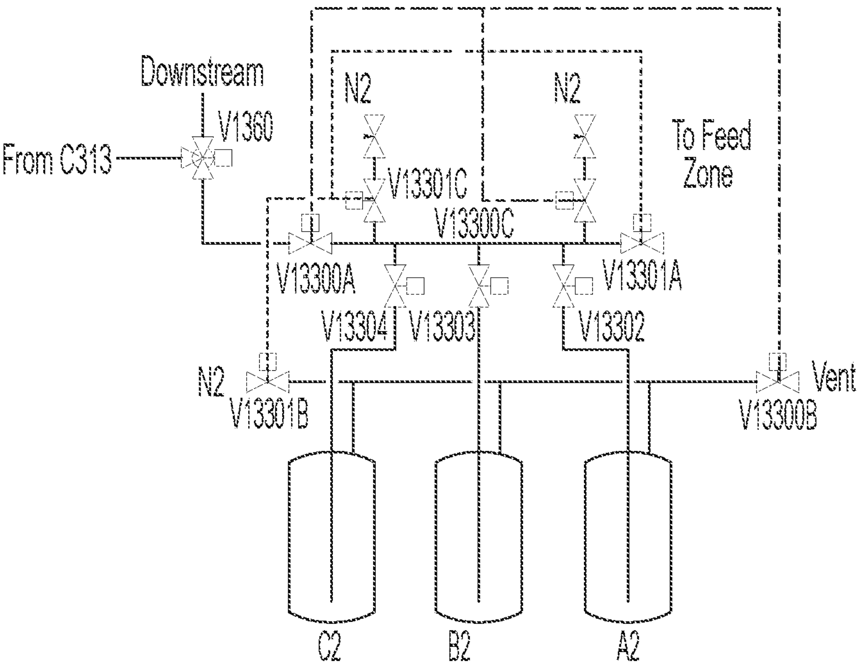
FIG. 13 is a schematic view of an in-process integrated multi-pass washing system for post oxidation/thiolation.

Refer to FIG. 11, FIG. 12, and FIG. 13 throughout this procedure. At the beginning, manually charge all six reuse bottles A through F and all 3 reuse bottles A2 to C2 with about 400 mL ACN.

When this procedure states that liquid is pumped down through the resin bed, it means that the waste pump at the outlet of the reactor bottom runs at a target setpoint, while nitrogen pressure pushes on top of the resin bed to push the liquid down through. The purpose of the peristaltic pump is to meter the liquid flow through the bed at a controlled rate.

Deblocking:

First use the reuse acid from the previous step to fluidize the resin, swell the resin bed, and wash away the ACN solvent. This step was done using fresh DCA/toluene solution on the first amidite cycle, but then it was done with the re-use DCA/toluene solution for the rest of the amidites. Set valve 1125A toward reuse acid, open valve 1125F, open valve 1152 vent, open FCV1 to charge the first portion of the reused acid (250 mL). The controller uses the feed can balance weight to measure out the correct mass. Close FCV1, open valve 1125B nitrogen to Chase the feed line with nitrogen into the feed zone, Close valve 1125B nitrogen. Close valve 1152 vent, open valve 1151 nitrogen, and push the acid solution into the reactor through the spray cone. Close valve 1151 nitrogen, open valve 1152 vent, open valve 1153, and open valve 1156 metered nitrogen. This blows nitrogen into the bottom of the reactor to fluidize the resin with the acid solution for user set time (20 seconds). Close valves 1156 metered nitrogen, 1153, 1152 vent, open valve 1151 nitrogen to push back down. After fluidization is done, open valve 1159 and start pump 1159, direct valve 1154 to valve 1160, direct valve 1160 to valve 1157, direct valve 1157 to waste. Open valve 1125F, open FCV1. This pushes the reuse acid through the feed zone and into the reactor at the same time that it is pumping out the bottom. Empty the contents of the reuse acid can completely. The amount ranged from about 1150 mL for cycle 1 to 2600 mL for cycle 21. Refer to Table 25. The amount of fresh acid for cycle 1 became the amount of reuse acid for cycle 2, and so on. Therefore, the amount of second charge reuse acid for cycle 2 was 1400 minus 250 mL, because 250 mL was used for the first fluidized portion, and so on. The step thoroughly flushes all of the ACN solvent out of the resin to waste. When all of the reuse acid is emptied from the vessel, close FCV1. Chase the feed line into the feed zone with nitrogen by opening 1125B nitrogen. Finish pumping all the reuse acid to waste. Total pumping time to waste ranged from about 3 minutes for cycle I to 4 minutes for cycle 21, gradually increasing because the volume was gradually increasing from one cycle to the next.

Charge the first portion of fresh acid into the feed zone (150 mL) by directing valve 1125A to the fresh acid source, open valve 1125F, open valve 1152 vent, open FCV1 to charge specified mass of fresh acid. The controller uses the feed can balance weight to deliver the correct mass. Close valve 1152 vent, open valve 1151 nitrogen to push acid into reactor through spray cone to evenly spray on top of the resin bed and keep the resin bed flat. Open valve 1159, valve 1154 toward valve 1160, valve 1160 toward valve 1157, valve 1157 toward reuse acid can, and start pump 1159. Pumping out of the deblock solution starts 5-30 seconds before the start of the second feed. The time is adjustable. The goal is to pump out until the deblock solution liquid level is just above the top of the resin bed when the fresh deblock solution starts to flow into the reactor, so that there is minimum back-mixing above the resin bed. The outlet pump rate is set to achieve total pump out in the desired reaction times stated in Table 25. The deblock solution is added to the reactor at about the same rate that it is pumping out by setting % open for the feed control valve 1. Feed acid solution into the top of the reactor at the same time that you are pumping it out the bottom of the reactor by opening valve 1125F, open valve 1125B nitrogen, open FCV1 to a value that balances with the flow of pump 1159 so that you keep a liquid level of acid on top of the resin bed while it flows through the resin plug flow. FCV1 closes after user specified total mass acid is reached. The total amount of acid charged, including the 150 mL used for the first charge, is listed for each cycle in Table 25. For example, total acid for cycle 1 was 1400 mL, which consisted of 150 mL for the first charge and 1250 mL for the second charge. The amount increased linearly each cycle and reached 2830 mL by cycle 21. At the end of the pumping time, open valve 1153 and valve 1155, and close nitrogen supply to feed zone. This pushes the residual acid to the reuse acid can until pressure in the feed zone drops below user setpoint (for example the pressure drops from 15 psig to 9 psig), which verifies that the reactor emptied before the automation moves on to the next step in the sequence.

In-Process Integrated Multi-Pass Washing after Deblocking

The first step in the In-process integrated multi-pass washing after acid is to use the solvent from bottle A to wash the resin and push to waste. The next step is to use the solvent from bottle B to pump through the resin and pump back to refill bottle A. Then the solvent from bottle C washes the resin in the reactor and pumps out to refill bottle B. And so on. Refer to FIG. 11 and FIG. 12. Overall, for the experiment, the wash schedule is detailed in Table 27. In the table, "w2" is the second wash portion after deblock. It washes through the resin bed and then pumps out the bottom of the reactor into bottle A. As shown in the table, "w2" becomes the first wash portion after deblock for cycle 2. "w3" is the 3rd wash portion after deblock for cycle 1, and it becomes the 2nd wash portion after deblock for cycle 2, then the 1 st wash portion after deblock for cycle 3. And so on, as listed in the table. The seventh wash portion is split up into 3 parts, for example w7a, w7b, and w7c in cycle 1 in the table. All three are pumped through the reactor and back to bottle F individually, so that pooled together the combined solvent becomes the $6^{th}$ wash portion in cycle 2, and so on.

TABLE 27

In-process integrated multi-pass wash schedule for washing after deblock reaction.

| wash portion after deblock | 1st | 2nd | 3rd | 4th | 5th | 6th | 7th | 8th | 9th |
|---|---|---|---|---|---|---|---|---|---|
| cycle1 | w1 | w2 | w3 | w4 | w5 | w6 | w7A | W7b | w7c |
| cycle2 | w2 | w3 | w4 | w5 | w6 | w7 | w8A | W8b | w8c |
| cycle3 | w3 | w4 | w5 | w6 | w7 | w8 | w9A | W9B | w9c |
| cycle4 | w4 | w5 | w6 | w7 | w8 | w9 | w10A | w10b | w10c |
| cycle5 | w5 | w6 | w7 | w8 | w9 | w10 | w11A | W11b | w11c |
| cycle6 | w6 | w7 | w8 | w9 | w10 | w11 | w12A | w12b | w12c |
| cycle7 | w7 | w8 | w9 | w10 | w11 | w12 | w13A | w13b | w13c |
| cycle8 | w8 | w9 | w10 | w11 | w12 | w13 | w14A | w14B | w14c |
| cycle9 | w9 | w10 | w11 | w12 | w13 | w14 | w15A | w15B | w15c |
| cycle10 | w10 | w11 | w12 | w13 | w14 | w15 | w16A | w16B | w16c |
| cycle11 | w11 | w12 | w13 | w14 | w15 | w16 | w17A | w17b | w17c |
| cycle12 | w12 | w13 | w14 | w15 | w16 | w17 | w18A | w18b | w18c |

TABLE 27-continued

In-process integrated multi-pass wash schedule for washing after deblock reaction.

| wash portion after deblock | 1st | 2nd | 3rd | 4th | 5th | 6th | 7th | 8th | 9th |
|---|---|---|---|---|---|---|---|---|---|
| cycle13 | w13 | w14 | w15 | w16 | w17 | w18 | w19A | w19b | w19c |
| cycle14 | w14 | w15 | w16 | w17 | w18 | w19 | w20A | w20b | w20c |
| cycle15 | w15 | w16 | w17 | w18 | w19 | w20 | w21A | w21b | w21c |
| cycle16 | w16 | w17 | w18 | w19 | w20 | w21 | w22A | w22b | w22c |
| cycle17 | w17 | w18 | w19 | w20 | w21 | w22 | w23A | w23b | w23c |
| cycle18 | w18 | w19 | w20 | w21 | w22 | w23 | w24A | w24b | w24c |
| cycle19 | w19 | w20 | w21 | w22 | w23 | w24 | w25A | w25b | w25c |
| cycle20 | w20 | w21 | w22 | w23 | w24 | w25 | w26A | w26b | w26c |
| cycle21 | w21 | w22 | w23 | w24 | w25 | w26 | w27A | w27b | w27c |

Valves 12201A (to feed zone), and valves 12201B and 12201C nitrogen supplies (FIG. 12), share the same actuator air line; therefore, when valve 12201 is opened, it pushes from the bottle to the feed zone. Likewise, valves 12200A (return from reactor) and valve number 12200B vent, share the same actuator air line; therefore, when valve 12200 is opened, the designated bottle receives used wash solvent from the reactor.

Start by opening valve 1152 vent, open valve 11201, open valve 11202. Nitrogen pushes the contents of bottle A into the feed zone. Bottle A completely empties. The automation system knows when it is completely empty by closing valve 1152 vent and waiting until pressure in the feed zone increases to a user specified value, which means that all of the solvent is transferred over from the bottle to the feed zone, and is chased by nitrogen into the feed zone. Open valve 1151 nitrogen to push solvent from the feed zone into the reactor through the spray cone by directing valve 1145 to the spray cone, to evenly spray on top of the resin bed and keep the resin bed flat, which makes the wash more efficient. Open valve 1159, valve 1154 toward 1160, valve 1160 toward 1157, valve 1157 toward waste. Turn on pump 1159 and pump the wash through the resin bed to waste. At the end of the pump time, close valve 1151, open valve 1153 and open valve 1155 to push residual wash to waste until pressure in the zone gets below a user specified value (example pressure drops from 15 psig to 9 psig). This ensures that all of the liquid is pushed out of the reactor to waste. Run pump 1159 at the same time so that all of the liquid is cleared from the pump to waste as well. That is the only wash from bottles A through F that goes to waste. It removes a large portion of the toluene and acid from the resin and pushes it to waste. The rest of the washes go back to the bottles A through E. This written procedure will describe taking solvent from bottle B and pushing it through the reactor and then back to bottle A, and the rest are similar. Open valve 1152 vent, valve 11201, valve 11203, to push wash solvent from bottle B into feed zone, pushing until the bottle is empty. This is verified by the automation system by closing valve 1152 vent and waiting until the pressure in the feed zone increases above a user setpoint (9 psig) which indicates that all of the liquid is transferred and chased with nitrogen. Close valve 11201 and valve 11203, open valve 1151 nitrogen, direct valve 1145 to the spray cone, and push wash solvent from the feed zone into the reactor through the spray cone onto the top of the resin to evenly spray on top of the resin bed and keep the resin bed flat. Open valve 1159, direct valve 1154 to valve 11200, open valve 11200, open valve 11202. Turn on pump 1159 so that the solvent washes through the resin bed and returns to bottle A. At the end of the user specified pumping time, open valve 1153 and valve 1155 and Close valve 1151 nitrogen, and wait until feed zone pressure drops below user setpoint (drops from 15 psig to 9 psig). This makes sure that all of the solvent is transferred through the reactor and into bottle A. Repeat this procedure to use the solvent in bottle C to wash the resin bed and return it bottle B, then from bottle D to C, and so on. The user has the option to specify whether or not any of the washes is fluidized. If the user chooses to fluidize one of the washes, then nitrogen blows up through the bottom of the reactor with valve 1152 open after transferring the wash into the reactor and before stating pump 1159. In this experiment, none of the in-process integrated multi-pass washes were fluidized. The user has the option to specify which of these washes for the system to do the automated Chase of the acid feed line, and which of these washes the system does the automated wash of feed zone walls and reactor walls. For example, suppose the user selects to do the feed line chase wash during the second wash. In this case, after the wash solvent from bottle B is pushed from the feed zone into the reactor, it sits there and waits before pumping through the reactor so that the system can chase the feed line. This is done by opening valve 1125C and using pump number 1130 to pump the specified volume of ACN (50 mL) solvent into the feed zone through the acid feed line. The solvent is chased forward by closing valve 1125C and opening valve 1125B nitrogen. Then, the chase solvent is pushed from the feed zone into the reactor by opening valve 1151 nitrogen. Then the combined solvents in the reactor pump through the resin and out to the destination bottle A as described above. Also, for example, suppose the user specifies to do the reactor wall wash during the ACN solvent wash from bottle F. In this case, after the solvent from bottle F pushes into the reactor, it sits there and waits for the reactor wall wash before pushing through the resin, the reactor wall wash is done as follows. Open valve 1152 vent, open valve 1130B, and open FCV2 until the specified mass pushes into the feed zone through the spray ball which washes the walls (50 mL). Valve 1130B opens during the charging because that helps the spray ball to work better at this scale, and nitrogen through valve 1130B also chases the solvent into the feed zone. Then, FCV2 closes, valve 1130B closes, valve 1152 vent closes, valve 1151 nitrogen opens, and valve 1145 is directed toward the wall spray device into the reactor. This procedure is repeated one more time to spray the walls of the feed zone one more time and the walls of the reactor one more time. Now the combined wash solvent from bottle F and from both reactor wall washes is pumped through the resin in the reactor back to bottle number E via pump 1159 as described above. At the end of these counter current washes, bottle F is empty.

Plug Flow Wash after Deblocking:

The next step is to wash the resin in the reactor with fresh ACN solvent and pump it out of the reactor to bottle F. This is done using the plug flow wash program and specifying the destination as bottle F. There are three destinations that the user can select for the plug flow wash program; bottle F, bottle C2, or waste. Plug flow wash is accomplished as follows. Open valve 1152 vent, open valve 1130B, and open FCV2 until the specified ACN solvent mass pushes into the feed zone through the spray ball which washes the walls (150 mL). Valve 1130B opens during the charging because that helps the spray ball to work better at this scale, and nitrogen through valve 1130B chases the solvent into the feed zone. Then, FCV2 closes, valve 1130B closes, valve 1152 vent closes, valve 1151 nitrogen opens, and valve 1145 is directed toward the spray cone into the reactor to evenly spray on top of the resin bed and keep the resin bed flat. Then the wash solvent is pumped through the resin bed by opening valve 1159 and starting pump 1159, and setting downstream valves V1154, V1160, V1157, V11200, V11300 into positions according to the destination (bottle F, bottle C2, or waste). In this case, the destination is bottle F. Run this step 2 more times, for a total of three 150-mL plug flow washes through the reactor and into bottle F.

By cycle number 7, counter current wash from bottle A contained about 600 mL (450 mL fresh ACN for the three plug flow wash steps, 100 mL for the reactor wall washes, and 50 mL for the feed line chase wash). The second wash from bottle B plus the 50 mL chase contained 600 mL. The third through $6^{th}$ washes from bottles C, D, E, F were 550 mL (the reactor wall wash 100 mL combined with the 450 mL from bottle F). Total wash solvent volumes flowing through the resin for all washes after deblock was about 4 L. However, only 600 mL of fresh ACN was charged to the system. The rest was re-use ACN from bottles A through F. This in-process integrated multi-pass wash strategy (Table 27) makes washing more efficient. Samples were taken from the final wash throughout the run, from cycle 1 through cycle 21, and all samples measured by NMR to be >99.9% ACN. The Cytiva AKTA synthesizer also achieves 99.9% ACN solvent at the end of the wash, but it requires 7× more wash solvent per mmol to achieve the same wash endpoint. There are several reasons for the improved efficiency of washing in the fluid the reactor that makes it superior to solvent washing in the packed bed reactors. (1) The reagents drain before the washing starts which eliminates the bulk liquid back mixing with the previous liquid, besides what holds up on the resin after draining. (2) the resin bed is fluidized during the reaction so that it is set flat and free of channels at the start of washing. (3) The reactor is not completely liquid filled therefore gravity forces complete radial distribution of the solvent on top of the resin bed. (4) The washes are split up into multiple smaller wash charges which allows them to be more plug flow with less back-mixing. (5) In-process integrated multi-pass washing allows a much more efficient use of the washer solvent. Only the "dirtiest" wash solvent exits the system to waste after each reaction, and the new clean solvent feed is only required for the final wash segments.

Coupling:

The coupling step pumps the phosphoramidite and the activator into the amidite zone, mixes them in the zone, pushes the coupling solution into the feed zone and then into the reactor, fluidizes the coupling solution in the reactor for the user specified amount of time, for example 10 minutes, then pushes the reaction solution out of the reactor so that it is completely drained to waste. More specifically, pump the specified amidite (200 mL) into the amidite activation zone and chase it in with nitrogen. Pump the activator solution (200 mL) into the amidite activation zone and chase in with nitrogen. Mix then push this mixture into the feed zone, and then into the reactor to start the coupling reaction on the resin. Fluidize the resin reactor intermittently throughout the coupling time (10 minutes or 15 minutes), about once every 45 seconds, bubbling with nitrogen into the bottom of the resin reactor for 15 seconds each time. For example, if we are using amidite number 4, then the automation does the following. Open valve 1142 vent, open valve 1104A, turn on pump number 1104. Pump the user specified mass (200 mL). The control system is monitoring the change in mass on the feed vessel weigh scale to measure out the correct amount. At the end of pumping, close valve 1104A and open valve 1104B to chase the amidite feed solution into the amidite zone with nitrogen. Do the same thing for the activator. Open valve 1142 vent, open valve 1120A, turn on pump 1120 to charge the user specified mass (200 mL), then close valve 1120A and open valve 1120B to chase forward with nitrogen into the amidite zone. Open valve 1143 to blow nitrogen backwards from the feed zone into the amidite zone to mix the activator in the amidite. Push the coupling solution into the feed zone by opening valve 1141 and opening valve 1143, closing valve 1142 vent, and opening valve 1152 vent. Push coupling solution from feed zone into the reactor by closing valve 1152 vent, closing valve 1143, opening valve 1151 nitrogen. Valve 1145 is directed to the spray cone. Completely mix the batch reaction by opening valve 1152 vent, opening valve 1153, opening valve 1158, and allowing the nitrogen to bubble into the bottom of the reactor and out the vent from the feed zone. Alternate pushing down to push the liquid down through the resin and then blowing nitrogen up the fluid out of the resin at user specified frequencies. Constant fluidization for the entire reaction time is also acceptable rather than intermittent. When pushing down, Valve 1152 vent is closed, valve 1151 nitrogen is opened, and valve 1153 is closed. When pushing up, valves are in the opposite position so that nitrogen can flow in the bottom of the reactor and out through the vent. At the end of coupling, push out to waste. This means that the system closes valve 1152, opens valve 1151 nitrogen, opens valve 1153, opens valve 1155. Valve 1154 directed toward valve 1160, valve 1160 directed toward valve 1157, valve 1157 directed toward waste. Then, open valve 1104A and run peristaltic pump number 1104 in reverse direction for about 1 mL to clear reagent solution from a dead leg and minimize the likelihood of dripping amidite 4 into the amidite zone during a different cycle.

Chase Feed Line Wash after Coupling:

This is a continuation of the example where we used amidite valve 1104. Open valve 1104C, open valve 1142 vent, pump the user specified amount of ACN solvent with pump 1130 (100 mL). Then, close valve 1104C and open valve 1104B to chase the solvent into the amidite zone with nitrogen. Close valve 1142 vent, open valve 1141, open valve 1143, open valve 1152 vent, and push the chase wash solvent into the feed zone. Then, push the chase wash into the reactor through the spray cone, pressurize reactor by closing valves 1143 and 1152, opening valve 1151, and pumping the wash solvent out the bottom of the reactor to waste.

Oxidation: (when Required Instead of Sulfurization):

Charge 0.05 M iodine solution (530 mL) into the feed zone, chasing it with nitrogen to clear the feed tubing. Push the solution into the reactor to start the oxidation reaction on the resin. Fluidize the resin reactor intermittently throughout the oxidation time (~4 minutes), about once every 30 seconds, bubbling with nitrogen into the bottom of the resin reactor for 12 seconds each time. Constant fluidization for the entire reaction time is also acceptable rather than intermittent. Start pumping the oxidation solution out through the resin bed at 540 mL/min for 65 seconds. Push the residual oxidation solution to waste out of the filter bottom. More specifically, charge iodine solution into the feed zone by opening valve 1152 vent, opening valve 1123A, and pumping with pump 1123 until reaching the user specified mass of iodine solution. The control system uses the weight of the balance for the iodine feed vessel to deliver the correct amount. After reaching the correct iodine deliver mass, close valve 1123A and open valve 1123B, so that nitrogen chases the iodine from the feed line into the feed zone. Close valve 1152 vent, Open valve 1151 nitrogen, direct valve 1145 to the spray cone, and wait user specified time to push the iodine from the feed zone into the reactor on top of the resin (about 10 seconds). Open valve 1159 and turn on pump 1159 for long enough time to pump out about 20 mL of ACN that was displaced out the bottom of the reactor when iodine pushed down through the resin. Proceed to run the oxidation reaction batch style by repeatedly fluidizing the resin bed in the iodine solution similar to how it was done in the coupling reaction. Use more vigorous nitrogen bubbling, however, by opening valve 1156 metered nitrogen in addition to valve 1158 during fluidization. Note that valve 1156 is higher flow nitrogen and valve 1158 is lower flow nitrogen, by the settings and CVs of the metering valves. Alternate between pushing down iodine through the resin and bubbling nitrogen up through the resin for fluidization for user specified times and use of specified frequency, for the desired duration of the oxidation reaction, for example 4 minutes. Constant fluidization for the entire reaction time is also acceptable rather than intermittent. At the end of the fluidized oxidation time, pump out the iodine solution to waste. To do this, open valve 1151 nitrogen, open valve 1159, direct valve 1154 to valve 1160, direct valve 1160 to valve 1157, direct valve 1157 to waste. Turn on pump 1159 to pump out to waste. After the designated pumping time, close valve 1151 nitrogen, open valve 1153, open valve 1155, and wait until pressure in the feed zone drops below our user specified value (drops from 15 psig to 9 psig), which ensures that all of the liquid is pushed out to waste and chased with nitrogen. Open valve 1123A and run pump number 1123 backwards for about 1 mL. This will help to clear reagent from a dead leg and ensure a clean subsequent chase of the feed line so that there will be no iodine left in the feed line and no possibility of iodine dripping into the feed zone during any of the other steps.

In-Process Integrated Multi-Pass Wash after Oxidation:

The in-process integrated multi-pass wash after oxidation is very similar to the in-process integrated multi-pass wash after acid deblocking, except that it uses only three bottles, A2, B2, and C2. Details of the equipment are shown in FIG. 13. Bottle A2 is used first, and that wash solvent is pushed through the reactor resin bed to waste. Then, solvent from bottle B2 is used to wash the reactor, and that solvent pushes through the resin bed and into bottle A2. And so on. At the end of the in-process integrated multi-pass washing, bottle A2 and B2 are filled, but bottle C2 is empty. Bottle C2 is refilled by the reactor wall wash, chase wash, and amidite zone wash as described next.

By cycle number 9, counter current wash from bottles A2, B2, C2 contained about 450 mL (450 mL fresh ACN going into bottle C2 from 100 mL post-coupling chase, 100 mL for the reactor wall washes, and 50 mL for the feed line chase wash, 100 mL amidite zone wash, and 100 mL plug flow wash). Total wash solvent volumes flowing through the resin for all washes after oxidation was about 1800 mL. However, only 450 mL of fresh ACN was charged to the system. The rest was re-use ACN from bottles A2, B2, C2. This in-process integrated multi-pass wash strategy makes washing more efficient. Samples were taken from the final wash throughout the run, from cycle 1 through cycle 21, and all samples measured by NMR to be >99.9% ACN, which is about the same as the Cytiva synthesizer gets at the end of the wash, but the Cytiva uses 7× more wash solvent per mmol, comparing to the Cytiva wash used after coupling plus oxidation summed. Final washes after sulfurization were also measured by NMR to be >99.9% ACN.

Reactor Wall Wash after Oxidation:

Open valve 1152 vent, open valve 1130B, open FCV2 until desired mass of solvent is in feed zone (50 mL). Solvent enters the feed zone through a spray ball so the walls of the feed zone are sprayed. Close valve 1130B, open valve 1151 nitrogen, direct valve 1145 toward wall spray, which sprays the walls of the reactor. Close valve 1151 nitrogen, open valve 1152 vent, repeat the steps to charge more wash solvent (50 mL) while spraying the walls of the feed zone and the walls of the reactor. Fluidization of solvent and resin in the reactor is optional on this step, as selected by the user; fluidization was not done here in this experiment. Open valve 1151 nitrogen, open valve 1159. Valve 1154 is directed to valve 1160, valve 1160 is directed to valve 11300. Open valve 11304, turn on Pump 1159, and pump the wash solvent through the reactor and into bottle C2. At the end of the pumping time, open valve 1153, open valve 1155, and close valve 1151 nitrogen. Push until user defined pressure in feed zone (drops from 15 psig to 9 psig) to make sure that all of the solvent clears from the reactor into bottle C2.

Chase Feed Line Wash after Oxidation:

Open valve 1152 vent, open valve 1123C, start pump 1130, pump specified mass of solvent into the feed zone (50 mL). Close valve 1123C, open valve 1130B to blow the solvent forward into the feed zone. Valve 1145 is directed toward the spray cone to evenly spray on top of the resin bed and keep the resin bed flat. Open valve 1151 nitrogen to push the wash solvent into the reactor. Open valve 1159, valve 11300, and valve 11304. Direct valve 1154 to 1160, direct valve 1160 toward valve 11300. Pump the wash solvent through the reactor into bottle C2. At the end of pump time, close valve 1151 nitrogen, open valve 1153, open valve 1155, and let the residual solvent push out of the reactor to bottle C2 until the feed zone pressure gets below her user setpoint (drops from 15 psig to 9 psig).

Amidite Zone Wash.

This is done after oxidation (or sulfurization) to get double value out of the wash solvent, because it washes the small residual drips off the walls of amidite zone and it also stores up more iodine-free, pyridine free, and water-free wash solvent in bottle C2 for the next phosphoramidite cycle. Open valve 1130E and start pump 1130 ACN into the wash bottle (100 mL). Stop pump 1130 and close valve 1130E. Open valve 1142 vent and open valve 1130F, push solvent into amidite zone through spray ball to thoroughly spray all surfaces inside the zone and wash away the previous amidite drips. The air from the solenoid to valve 1130F also supplies the actuator for a nitrogen supply valve on top of the wash vessel, so that nitrogen pressurizes the wash vessel the same time valve 1130F opens. Valve 1130F is a 3-way valve that is fail open to vent. Close valve 1142 vent, close valve 1130F (Closing valve 1130F also switches the N2 supply valve on the top of the wash vessel back to vent), open valve 1141, open valve 1143, open valve 1152 vent. This pushes all of the wash solvent into the feed zone for user specified time (example 5 seconds). Close valves 1141, 1143, 1152, and open valve 1151 nitrogen. Open valve 1159, set valve 1154 toward valve 1160, valve 1160 toward valve 11300, open valve 11300, and open valve 11304. Start pump 1159, pump the wash solvent through the resin bed and into bottle C2 for a user specified time. At the end of the pumping, open valve 1153 and valve 1155, close valve 1151 nitrogen, let the nitrogen pressure push the residual solvent from the reactor into bottle C2. Wait until pressure in feed zone gets below user specified value which confirms that all of the solvent is pushed out of the reactor and into bottle C2.

Plug Flow Wash after Oxidation:

Do a plug flow wash as described previously but push the wash solvent into bottle C2 (100 mL).

Capping Reaction:

Charge capping solution A and capping solution B (100 mL each) into the feed zone, chasing them with nitrogen to clear the feed tubing. Push the solution into the reactor to start the capping reaction on the resin. Fluidize the resin reactor 2 times, bubbling with nitrogen into the bottom of the resin reactor for 12 seconds each time. Total time for both fluidizations is about 1 minute. Constant fluidization for the 1 minute is also acceptable rather than intermittent. Start pumping the reaction solution out through the resin bed at 200 mL/min for about 1 minute. Push the residual reaction solution to waste out of the filter bottom. Specific automation sequences for the capping step are similar to the automation for the oxidation step, except that the capping reagents come in through valve 1121A and valve 1122A, using valves 1121B, 1122B, 1121C, 1122C for nitrogen chasing and solvent chasing as described in the oxidation step.

Another embodiment of the synthesizer uses three in-process integrated multi-pass wash bottles, A, B, and C, for the wash after capping as well. In this experiment however, the washes after capping were sent directly to waste.

Sulfurization (Thiolation) Reaction (when Required Instead of Oxidation):

Charge 0.2 M xanthane hydride solution (650 mL) into the feed zone, chasing it with nitrogen to clear the feed tubing. Push the solution into the reactor to start the sulfurization reaction on the resin. Fluidize the resin reactor intermittently throughout the sulfurization fluidizing time (~8 minutes), about once every 30 seconds, bubbling with nitrogen into the bottom of the resin reactor for 12 seconds each time. Constant fluidization for the entire reaction time is also acceptable rather than intermittent. Start pumping the xanthane hydride solution out through the resin bed at 700 mL/min for 60 seconds. Push the residual xanthane hydride solution to waste out of the filter bottom. Detailed automation sequences for sulfurization step are similar to automation for oxidation step, except that xanthane hydride solution is pumped in with pump number 1124 and using valves 1124A, 1124B, and 1124C. The first two cycles and the last three cycles used sulfurization. After the first two cycles, bottles A2, B2, and C2 were removed and replaced with new A2, B2, and C2 bottles each filled with about 400 mL fresh ACN. Then, before the last three cycles, bottles A2, B2, and C2 were removed and replaced with the old A2, B2, and C2 bottles still filled with xanthane hydride containing ACN wash solvent from the first two cycles. This was because chose not to use the xanthane hydride containing ACN wash solvent for the washes after oxidation, and vice versa, in this experiment.

Similar to washing after oxidation, total wash solvent volumes flowing through the resin for all washes after sulfurization was about 1800 mL. However, only 450 mL of fresh ACN was charged to the system. The rest was re-used ACN from bottles A2, B2, C2. Again, this in-process integrated multi-pass wash strategy makes washing more efficient.

Final Cycle:

The final amidite (MeMOP) does not have a DMT protecting group at the 5' position, so it does not need a final deblocking. After the final MeMOP coupling, wash, sulfurization, and wash are complete, wash with DEA solution. Charge DEA solution (500 mL) into the feed zone. Chase the DEA solution into the feed zone with nitrogen to clear the feed tubing. Push the solution into the reactor. Fluidize the resin bed two times to achieve complete liquid-solid contacting and re-set the resin bed. Total time for both fluidizations is about 1 minute. Constant fluidization for 1 minute is also acceptable rather than intermittent. Start pumping the DEA solution through the resin bed at 100 mL/min for 600 seconds. Simultaneously pump more DEA solution (500 mL) into the feed zone in parallel, so that it enters the top of the reactor at about the same rate that it is pumping out. Chase the DEA solution into the feed zone with nitrogen to clear the feed tubing. A total of 1 L pumps through the resin bed during the 600 seconds. Push the residual DEA solution to waste out of the filter bottom. Repeat this DEA treatment one more time.

Wash thoroughly with ACN as follows. All of these ACN washes after DEA used fresh ACN from the feed can and pushed out the reactor to waste. Use 200 mL ACN to chase the DEA feed line and do a plug flow wash of the resin bed, similar to the other chase washes described earlier in this procedure. Do three plug flow washes with 150 mL ACN each, using the same procedure as the plug flow washes described previously. Wash the wall of the reactor with 50 mL ACN as described previously ("reactor wall wash"). Do two plug flow washes with 150 mL ACN each, using the same procedure as the plug flow washes described previously.

Drying: Slurry the resin out of the reactor. Transfer onto a single plate filter. Dry with nitrogen blowing down through the resin bed for 5-6 hours. Total weight of recovered dry resin after removing a −3 g sample was 115.7 g.

A small sample was taken for cleavage and deprotection and UPLC. Results are included in Table 17, UPLC results for examples 6 through 10 and comparison to Cytiva AKTA. Purity was 77.89% FLP. This is slightly lower than the other fluid bed reactor examples in the table, but there is a specific reason. We accidentally got a small amount of acid in the coupling feed lines on cycle 19. This caused a larger than normal truncation at the 19 mer, as shown in the table. FLP was about 1.5% lower because of this mishap. Otherwise, we suppose that FLP would have been 79-80% for the run. Yield and purity data for this experiment are listed in Table 17.

Do bulk cleavage and deprotection (C/D) in two lots, with about half of the resin bound crude product in each lot. For each of the two lots, C/D was accomplished by combining the resin with 28% aq. ammonium hydroxide (30 mL/g of resin) and heating to 38° C. in a sealed vessel for 18-20 h. To the 1850 mL Ace-thread pressure vessel equipped with pressure gauge, 25 psig pressure relief safety valve, thermocouple, heating mantle and magnetic stir bar was charged ANGPTL3 AS protected and AMMONIUM HYDROXIDE (28 mass %) in WATER (1.68 L, 2000 g, 10000 mmol). The thin slurry was sealed and stirred while heating to 38° C. overnight. 58.43 g resin bound product was charged in the first lot, and 56.91 g resin bound product was charged in the second lot. After 18 hours at 38° C., turn off heat and add an ice water bath to cool the reactor to less than room temperature. The resin was allowed to settle and a weighed aliquot of the supernatant liquid was diluted into a weighed amount of mill-Q water. Each lot was analyzed by UPLC. Lot 1 had 77.6% FLP and lot 2 had 78.4% FLP. The 19 mer truncation was 2% in both lots, as explained earlier. Filter the bulk solution to remove the spent resin. Wash the spent resin from each lot with 3×150 mL of 1:1 EtOH:$H_2O$. This time ammonia was not stripped off in a rotovap, instead it was removed with the C/D byproducts by TFF. Crude masses obtained were 27.52 g from lot 1 and 28.07 g from lot 2. The material was forward processed through chromatographic purification, which is beyond the scope of this document.

Example 10: Pilot Scale Fluid Bed Synthesizer with in-Process Integrated Multi-Pass Washing Example 10 was very similar to Example 9. In Example 10, however, the in-process integrated multi-pass wash was done after capping as well. Example 10 demonstrated the lowest ACN solvent wash in mL/mmol, out of all the examples.

A same antisense strand of AngPTL3 (FIG. 10) was synthesized in a modified version of the fluidized bed reactor system from Example 10.

5' MeMOP*fG*fU*fAfUmA fAmCmC fUmUmC mCfAmUmUmUmUmGmA*mG*mG3,

The synthesis of this molecule using the fluidized bed method of the current invention is herein described, and comprises deblocking, coupling, oxidizing (or sulfurization), and capping steps to sequentially install the remaining phosphoramidites.

Resin bed height reaches 5 cm acetonitrile solvent wet and 4 cm dry by the end of the experiment. Maximum resin bed height of 6 cm is reached during downflow portions of the final deblocking step. Maximum pressure drop across the resin bed is 15 psig during the experiment, because that is the pressure of the supply nitrogen used to push liquid through the resin bed. Two equivalents of amidite are used for the couplings, except for the final cycle. 2.1 eq was used for MeMOP amidite coupling. Overall synthesis conditions are given in Table 28. Deblocking time and volume fresh DCA solution from beginning to end of synthesis are given in Table 29.

TABLE 28

Synthesis conditions for example 10.

| Item | Value | Unit |
|---|---|---|
| Resin loading | 249 | μmol/gram |
| Resin starting amount | 40.18 | gram |
| Synthesis scale | 10.00 | mmol |
| Amidite concentration | 0.1 | Min acetonitrile |
| Amidite equivalence | 2 all but MeMOP, 2.1 eq MeMOP | eq |
| Activator concentration | 0.5 | Min acetonitrile |
| Activator equivalence | 10 | eq |
| Amidite solution, amount per cycle | 200 | mL |
| Activator solution, amount per cycle | 200 | mL |
| Coupling reaction time | 15 (cycles 8, 12, 15 to 21)<br>10 (all other cycles) | Min |
| Iodine equivalence | 2.1 (cycles 3 to 4)<br>2.65 (cycles 5 to 18) | Eq |
| Oxidation solution, amount per cycle | 420 (cycles 3 to 4)<br>530 (cycles 5 to 18) | mL |
| Oxidization time | 5 | Min |
| Sulfurization equivalence | 13 | Eq |
| Sulfurization solution, amount per cycle | 650 | mL |
| Sulfurization time | 10 | Min |
| Capping solution A, amount per cycle | 100 | mL |

TABLE 28-continued

| Synthesis conditions for example 10. | | |
|---|---|---|
| Item | Value | Unit |
| Capping solution B, amount per cycle | 100 | mL |
| Capping time | 4 | Min |

TABLE 29

Deblocking time and volume fresh DCA solution from beginning to end of synthesis for example 10.

| cycle | amidite | volume of 3% DCA solution (mL) | deblocking plug flow pumping time (minutes) |
|---|---|---|---|
| 1 | MG-S | 1080 | 8.3 |
| 2 | MA-S | 1200 | 8.3 |
| 3 | MG | 1256 | 8.3 |
| 4 | MU | 1312 | 8.3 |
| 5 | MU | 1368 | 9 |
| 6 | MU | 1424 | 9 |
| 7 | MU | 1480 | 9 |
| 8 | FA | 1536 | 9 |
| 9 | MC | 1592 | 9 |
| 10 | MC | 1648 | 9.7 |
| 11 | MU | 1704 | 9.7 |
| 12 | FU | 1760 | 9.7 |
| 13 | MC | 1816 | 9.7 |
| 14 | MC | 1872 | 9.7 |
| 15 | FA | 1928 | 9.7 |
| 16 | MA | 1984 | 9.7 |
| 17 | FU | 2040 | 9.7 |
| 18 | FA | 2096 | 9.7 |
| 19 | FU-S | 2152 | 9.7 |
| 20 | FG-S | 2208 | 9.7 |
| 21 | MEMOP-S | 2264 | 9.7 |

Reagents and lot numbers used for Example 9 are shown in Table 30.

TABLE 30

Reagent lots used for Example 10.

| Reagent | Lot |
|---|---|
| ACN | Fisher 214141 |
| Capping solution A, 1-Methylimidazole/ACN (20/80 v/v) | see below |
| Capping solution B, 1:1 Mixture B1 and B2. B1 is 40 vol % acetic anhydride in ACN. B2 is 60 vol % 2,6-lutidine in ACN | see below |
| 0.2M Xanthane hydride in ACN/pyridine (70/30 v/v) | see below |
| 0.05M Iodine in pyridine/water (90/10 v/v) | see below |
| Deblocking, Dichloroacetic acid (3% DCA/toluene v/v) | see below |
| DEA, 20% diethylamine in ACN (20/80 v/v) | see below |
| Activator reagent, 0.5M 5-(Ethylthio)-1H-tetrazole in ACN | DW336-US |
| Kinovate Nittophase HL 2'OMeG(iBu) 250, 249 umol/g | H08023 |

All amidite solutions were prepared with ACN from Fisher Lot #212215. Dissolve amidites into ACN solvent as follows. Mix until solution. Add molecular sieve dry packs to sealed bottle.

ACN lots used: EMD Lot #52261, EMD Lot #52261, Fisher #214141

| Amidites needed: | | Solvent required: |
|---|---|---|
| mA | 45.91 g | 517 mL |
| mC | 76.74 g | 957 mL |
| mG | 44.98 g | 517 mL |
| mU | 89.55 g | 1177 mL |
| fA | 64.56 g | 737 mL |
| fG | 25.48 g | 297 mL |
| fU | 55.19 g | 737 mL |
| MeMOP, 16.53 g | | 297 mL |

Amidite molecular weights were as follows:

mA DMT-2'-O-MeA(bz) phosphoramidite, MW 887.97
mC DMT-2'-O-MeC(Ac) phosphoramidite, MW 801.87
mG DMT-2'-O-MeG(iBu) phosphoramidite, MW 869.95
mU DMT-2'-O-MeU-CE phosphoramidite, MW 760.82
fA DMT-2'-F-dA(bz) phosphoramidite, MW 875.93
fC DMT-2'-F-dC(Ac) phosphoramidite, MW 789.84
fG DMT-2'-F-dG(iBu) phosphoramidite, MW 857.9
fU DMT-2'-F-dU-CE phosporamidite, MW 748.8
MeMOP, MW 556.5

Prepare the reagent solutions as follows:

Cap B1:
Acetic Anhydride: Macron Fine Chemicals Lot #0000239131
Acetonitrile: Fisher Lot #214141
Charge 481 mL of Acetic Anhydride and 722 mL of ACN to bottle.

Cap B2:
2,6—Lutidine: Acros Lot #A0428332
Acetonitrile: EMD Lot #52261
Charge 722 mL of Lutidine and 481 mL of ACN to bottle.

Cap A:
1-Methylimidazole: Alfa Aesar Lot #5009J24W
Acetonitrile: Fisher Lot #214141
Charge 481 mL of Imidazole. Charge 1924 mL of ACN.

0.2M Xanthane Hydride Sulfurization Solution:
Xanthane Hydride: TCI Lot #QLXKC-LI
Pyridine: Fishers Lot #212147
Charge 3775 mL of Pyridine. Charge 114 g of XH to Pyridine bottle. Mix until solution.

Oxidation Solution:
Iodine solution (0.05M)
Honeywell Lot #EA702-US
Charged ~8 Kg of keg stock to feed can.

Activator Solution:
Honeywell Lot #EA713-US
Charge ~4.3 Kg of keg stock solution to feed can.

20% DEA in Acetonitrile:
DEA: Sigma-Aldrich Lot #STBJ5069
DEA: Sigma-Aldrich Lot #SHBK7197
Acetonitrile: Fisher Lot #214141
Charge 400 mL of DEA to bottle. Charge 1600 mL of ACN to bottle.

3% DCA in Toluene Solution:
DCA: Sigma Aldritch Lot #MKCQ92
Toluene: Superior Lot #HX11315122

Lot #1
1. Charged 18,664 mL of Toluene to a carboy
2. Charged 577 mL of DCA to carboy
3. Charged carboy to feed can Lot #2
1. Charged 19,516 mL of Toluene to a carboy
2. Charged 604 mL of DCA to carboy
3. Charged carboy to feed can Begin with mG coupled onto NittoPhase HL 2' OMeG (iBu) 250 resin (249 μmol/g) using known methods (herein referred to as "mG-resin"), and refer to FIG. 11 and for the setup of the synthesizer apparatus. Use ACN to slurry 40.18 g (10.00 mmol) of the mG-resin into a 10.16 cm inside diameter reactor with a 40 micron sintered mesh filter frit at the bottom. The initial resin depth is about 1 cm tall.

Prime all pumps and feed lines. ACN is pushed through a bed of molecular sieves on the way into an inerted feed can. ACN and DCA in toluene are fed from feed cans via pressure push and controlled with automated flow control valves. All other feeds use peristaltic pumps and feed vessels. The amidite solutions are contained separately in feed vessels labeled "AM. 1 L" and connected to peristaltic pumps attached to valves V1101A through V1108A in FIG. 11. The MeMOP phosphoramidite used one of the AM. feed vessels. The activator and DEA solutions are contained in feed vessels labeled "Activ. 5 gal" and "DEA 1 L", respectively in FIG. 11.

There is no capping for cycles 2 through 9 (nucleosides 3 through 10). Capping is not needed after cycle 21 MeMOP is added. For each phosphoramidite added in the synthesis, perform the deblocking, coupling, oxidizing (or sulfurization where there is a P=S linkage in the sequence), and capping steps sequentially as described in Example 9, except for the following differences.

Three additional 1-L bottles, bottles A3, B3, and C3, were used along with sequenced automated block valves to accomplish the in-process integrated multi-pass washing after capping as well. These are not shown in FIG. 11, but they are similar to the FIG. 11 section with bottles A2, B2, and C2 and the FIG. 13 description of A2, B2, and C2. All the valves for bottles A3, B3, and C3 were the same as those shown in FIG. 13, but they were labeled as the 400 series, i.e. valves 400A, 400B, 400C, 401A, 401B, 401C, 402, 403, 404. The multi-pass washing procedure was similar to what was described for washing after oxidation/thiolation in Example 9. All the solvent from bottle A3 wash was pumped through the resin bed and to waste, then bottle B3 wash was pumped through the resin bed and to bottle A3, and bottle C3 wash was pumped through the resin bed and to bottle B3. Then, two 150 mL virgin ACN washes were done, each pumping through the resin bed and pumping back to bottle C3. The first 150 mL cleaned the reagent feed tubing into the feed zone, then washed the resin bed plug flow. The second 150 mL wash sprayed the feed zone walls, then sprayed the walls of the reactor, then washed the resin bed plug flow. Overall, after the multi-pass wash bottles were prefilled with 300 mL each, a total of 1.3 L fresh ACN was used for washing each cycle.

This includes 550 mL after deblocking, 100 mL after coupling, 350 mL after oxidation, and 300 mL after capping. In comparison, at the 10 mmol scale, the packed bed synthesizers typically use about 8-10 L fresh ACN for solvent pushes and solvent washes during each cycle. Samples proved that each of the washing endpoints were the same as what is typically achieved using packed bed synthesizers, i.e. ~99.9% ACN in the final portion of the wash solvent exiting the reactor. The reasons for the ~85% solvent reduction of ACN wash solvent versus packed bed reactors are: the regents are drained from the reactor prior to washing, the resin bed is set flat and channel-free by the fluidizations during reaction, the wash solvent is distributed effectively on the resin by the cone spray distributor, the washes are split up into multiple plug flow segments, and most importantly, the in-process integrated multi-pass washing makes the use of wash solvent much more efficient. For example, only 550 mL virgin ACN is used for washing after deblocking, but total volumes of wash solvent passing through the reactor during wash after deblocking is 3500 mL. Likewise, only 350 mL virgin ACN is used for washing after oxidation/thiolation, but total volumes of wash solvent passing through the reactor during wash after oxidation/thiolations 1700 mL, given that the 100 mL wash after coupling gets pumped to bottle C2. Likewise, only 300 mL virgin ACN is used for washing after capping, but total volumes of wash solvent passing through the reactor during wash after capping is 1200 mL. Most importantly, the reduced washing does not change the wash endpoints. The wash endpoints are 99.9% ACN in packed bed synthesizer experiments using 800-1000 mL/mmol total ACN wash solvent per cycle, and the wash endpoints are 99.9% ACN in the fluidized bed synthesizers using 130 mL/mmol total ACN wash solvent per cycle. The difference is that the wash solvent is used much more efficiently in the fluid bed reactor with in-process integrated multi-pass washing.

Another difference compared to Example 9, is that wash solvent after coupling is reused in the wash solvent after oxidation/thiolation in Example 10. The procedure is run as follows for chase wash after coupling:

Chase Feed Line Wash after Coupling:

This is a continuation of the example where we used amidite valve 1104 (FIG. 11).

Open valve 1104C, open valve 1142 vent, pump the user specified amount of ACN solvent with pump 1130 (100 mL). Then, close valve 1104C and open valve 1104B to chase the solvent into the amidite zone with nitrogen. Close valve 1142 vent, open valve 1141, open valve 1143, open valve 1152 vent, and push the chase wash solvent into the feed zone. Then, push the solvent into the reactor on top of the resin through the spray cone, pump through the resin out the bottom of the reactor and into bottle C2. To do this, close valve 1152 vent, close valve 1143, open valve 1151 nitrogen, direct valve 1145 to spray cone, open valve 1159, direct valve 1154 to valve 1160, direct valve 1160 to valve 11300, open valve 11300, open valve 11304, and pump with pump 1159. At the end of the user specified pumping time, close valve 1159, open valve 1153, open valve 1155, and let the residual wash push with nitrogen into bottle C2 until the feed zone pressure drops below or user specified value (drops from 15 psig to 9 psig).

All other parts of the procedure are the same as written in Example 9, except that the multi-pass wash is also done after capping.

Drying: After the final cycle, DEA treatment, and washing, slurry the resin out of the reactor. Transfer onto a single plate filter. Dry with nitrogen blowing down through the resin bed for 6 hours. Total weight of recovered dry resin including small sample was 116.24 g.

A small sample was taken for cleavage and deprotection and UPLC. Results are included in Table 17 (UPLC results for examples 6 through 10 and comparison to Cytiva AKTA).

Examples 6-9 all synthesized the same strand. As described above, Example 6 demonstrates an alternative research scale synthesizer design. The new design does not have feed zones for reagents, other than amidites and activator. It uses fewer pumps with multiple heads in parallel, and it has integrated solvent re-use from one phosphoramidite cycle to the next, which reduces solvent wash volumes.

Example 7 demonstrates an alternative research scale synthesizer design, with integrated re-use of excess deblocking reagent solution from one phosphoramidite cycle to the next, which helps to reduce acid volumes needed for the deblocking reaction. This example used 29% of the DCA solution that is typically used in the Cytiva packed bed synthesizers per mmol.

Example 8 demonstrates a new reactor design for scale up. The new 10 mmol scale reactor design uses a different wash strategy, with larger number of smaller washes. The washes are a combination of plug flow and fluidized, designed for efficiency of reagent removal. A cone spray distributor is used to keep the resin bed flat and enable efficient plug flow washes. The example demonstrates 40% less wash solvent compared to Cytiva AKTA synthesizers per mmol. Toluene is used as the wash solvent prior to deblocking reaction to pre-swell the resin and eliminate ACN, which makes the deblocking reaction more efficient.

Example 9 had no toluene washes before deblocking. Toluene was replaced with reuse acid. The cleanest part of the acid deblocking solution from one cycle is used to pre-swell the resin and wash the ACN from the resin at the beginning of the next cycle. Example 9 had no capping for cycles 2 through 9. Example 9 had in-process integrated multi-pass washing after deblocking, oxidation, and thiolation.

Example 10 was like example 9, but it also had in-process integrated multi-pass washing after capping, and the wash after coupling is re-used in the wash after oxidation/thiolation. Example 10 had the lowest ACN wash solvent compared to all other examples in this document, which was about 850 less wash solvent compared to Cytiva AKTA synthesizers per mmol.

A guide to all the fluid bed reactor embodiments is given in Table 31.

UPLC chromatogram overlays for examples 1-5 are shown in FIGS. 14 and 15, and UPLC chromatogram overlays for examples 6-10, and "AKTA compare 1-4" examples are shown in FIGS. 16 and 17. These show that impurity profiles from the fluid bed synthesizer experiments are similar to impurity profiles from the Cytiva AKTA OP100 experiments. There are no new impurities in the fluid bed synthesizer experiments that are not also in the Cytiva AKTA OP100 experiments. However, the AKTA synthesizer resin bed height was maximum 2 cm on the high purity experiments, while the fluid bed reactor resin bed height was up to 30 cm. Also, besides purity consideration, the fluid bed synthesizer achieved higher yield, -85% lower solvent wash volumes, and lower DCA equivalents versus the AKTA.

Summary of Ion-Pairing UPLC Method Conditions for Purity Analysis of Anti-Sense Strands in examples 1-9.

- Instrument: Waters I-Class Acquity UPLC with binary pump
- Column: 50×2.1 mm Waters BEH C18, 1.7 mm, 130 A (pn 186003949)
- Column Temp.: 55 C
- Mobile Phase A: 10 mM DIPEA, 100 mM HFIP in water
- Mobile Phase B: Acetonitrile
- Gradient
  - Initial conditions: 99% A/1% B
  - Increase 1% to 24.3% B in 25 min
  - Increase 24.3-100% B in 0.1 min
  - Hold 100% B for 1.9 min
  - Decrease 100% to 1% B in 0.1 min
  - Hold 1% B for 2.9 min
  - Total run time 30 min
- Flow Rate: 0.6 mL/min
- Wavelength: 260 nm

TABLE 31

Guide to fluid bed reactor embodiments.

| Example | 1 | 2 | 3 | 4 | 6 | 7 | 8 | 9 | 10 |
|---|---|---|---|---|---|---|---|---|---|
| low DCA reagent use | | | | | | X | | | |
| low ACN solvent use | | | | | X | | X | X | X |
| tall resin bed height | | X | | | | | | | |
| the cleaner portion of deblocking reagent solution is reused from one cycle to the next | | | | | | X | | X | X |
| the cleaner portion of wash solvent is reused from one cycle to the next | | | | | | | X | X | X |
| in-process integrated multi-pass washing | | | | | | | | X | X |
| pilot scale | | | | | | | X | X | X |
| cone spray distributor | | | | | | | X | X | X |
| fluidize with no inert gas bubbling | X | | | | | | | | |
| reactor expands into a larger diameter upper section | | X | | X | X | X | | | |
| initial portions of the solvent wash and or reagent charges are fluidized to mitigate the otherwise high pressure drop | | X | X | X | | | | | |
| deblock reaction is done with no fluidization at all when the fresh acid solution enters the reactor, only plug flow | | | | | | X | | X | X |
| reagent charges other than coupling are split up into 2 portions, a fluidized portion followed by a plug flow portion | | | X | | | | | | |
| capping is omitted from some of the cycles | | | | | | X | | X | X |
| reagents are charged to individual feed zones before pushing into the reactor | X | X | | X | | X | | | |
| reagents are charged to a common feed zone before pushing into the reactor | | | X | | | | X | X | X |
| amidite and activator are mixed in the amidite feed zone by bubbling with nitrogen prior to transfer into the reactor | | | X | | | X | X | X | X |
| reagents are pushed directly into the reactor rather than a feed zone | | | | | X | | | | |
| reactor, feed zone, and amidite zone have spray devices for washing walls | | | | | | | X | X | X |
| wash solvent after coupling is reused in the wash solvent after oxidation/thiolation | | | | | | | | | X |

Exemplary Embodiments

Embodiment 1. A method of adding an oligonucleotide to a solid phase resin within a bed reactor, the method comprising:

removing a protecting group from the 5' position of an oligonucleotide that is attached to the solid phase resin;

adding an activated amidite solution to the bed reactor, wherein the activated amidite solution comprises an amidite and flows up and down within the bed reactor or fluidizes with nitrogen bubbling or other agitation and reacts at the 5' position of the oligonucleotide, wherein the phosphorous linkage found within the amidite comprises a P atom that is in an oxidation state of III; and converting the P atom from an oxidation state of III to an oxidation state of V.

Embodiment 2. The method of Embodiment 1, further comprising the step of adding a capping solution before or after converting the P atom from an oxidation state of III to an oxidation state of V, wherein if the coupling moiety did not react with the amidite solution, the capping solution caps the coupling moiety such that no additional amidite can be coupled to the coupling moiety, wherein the capping solution flows up and down within the bed reactor or fluidizes with the resin beads using inert gas bubbling or other agitation, or flows down through the resin bed without fluidizing/mixing, or a fluidized portion of the reaction followed by a plug flow portion.

Embodiment 3. The method of Embodiment 1, further comprising the step of removing the activated amidite solution from the from the bed reactor by passing the amidite solution through a filter located at the bottom of the bed reactor.

Embodiment 4. The method of Embodiment 1, further comprising the step of adding a first washing solution to the bed reactor, wherein the adding of the first washing solution occurs after removing the protecting group.

Embodiment 5. The method of Embodiment 4, further comprising the step of adding a second washing solution to the bed reactor, wherein the adding of the second washing solution occurs after the activated amidite solution has been added to the bed reactor.

Embodiment 6. The method of Embodiment 5, wherein the first and second washing solutions flow up and down within the bed reactor and wherein the method further comprises the step of individually removing the first and second washing solutions from the bed reactor by passing the first and second washing solutions through a filter located at the bottom of the bed reactor.

Embodiment 7. The method of Embodiment 5, wherein the adding of the second washing solution occurs before the step of converting the P atom from an oxidation state of III to an oxidation state of V.

Embodiment 8. The method of Embodiment 5, further comprising the step of adding a third washing solution to the bed reactor, wherein the adding of the third washing solution occurs after converting the P atom from an oxidation state of III to an oxidation state of V.

Embodiment 9. The method of Embodiment 8, wherein the third washing solution flows up and down within the bed reactor and wherein the method further comprises the step of removing the third washing solution from the bed reactor by passing the third washing solution through a filter located at the bottom of the bed reactor.

Embodiment 10. The method of Embodiment 1, wherein the protecting group is a DMT group and wherein the removing the protecting group comprises reacting the 5' position of an oligonucleotide with an activating solution comprising an acid in solvent.

Embodiment 11. The method of Embodiment 10, wherein the method further comprises the step of removing the activating solution from the bed reactor by passing the activating solution through a filter located at the bottom of the bed reactor.

Embodiment 12. The method of Embodiment 1, wherein the upward and downward flow within the bed reactor is accomplished by adding pressure to the top of the reactor for the downward push and then releasing pressure from the top of the reactor for the upward push.

Embodiment 13. The method of Embodiment 1, wherein the solid and liquid fluidized bed mixing within the bed reactor is accomplished by adding nitrogen or another gas to the bottom of the reactor or some other type of agitation.

Embodiment 14. A system for adding an oligonucleotide to a solid phase resin comprising a bed reactor and an activated amidite solution, wherein the activated amidite solution comprises an amidite and flows up and down within the bed reactor or fluidizes with inert gas bubbling or other agitation.

Embodiment 15. The system of Embodiment 14, wherein the bed reactor comprises an inlet that allows pressurized gas to enter the bed reactor, wherein the pressurized gas or some other type of agitation causes the amidite solution to mix with the solids within the bed reactor.

Embodiment 16. The system of Embodiment 15, wherein the inlet is positioned at the bottom of the bed reactor.

Embodiment 17. The system of Embodiment 14, wherein the bed reactor is pressurized from the top of the bed reactor, wherein the pressure causes the amidite flows up and down within the bed reactor.

Embodiment 18. The method of Embodiment 5, wherein the first and second washing solutions mix within the bed reactor and wherein the method further comprises the step of individually removing the first and second washing solutions from the bed reactor by passing the first and second washing solutions through a filter located at the bottom of the bed reactor.

Embodiment 19. The method of Embodiment 5, wherein the wash solvent is drained out the bottom of the filter reactor prior to charging the next reagent; the reagent is drained out the bottom of the filter reactor prior to charging the next wash solvent; the resin bed is mixed to suspend the resin particles in the reagents and/or wash solvents by inert gas bubbling or up and down flow of the liquid at selected times during selected reactions and/or washes in each cycle.

Embodiment 20. The method of Embodiment 19, wherein a first portion of the reagents are charged into the reactor, the first portion is fluidized at the start of the reaction for a target amount of time to achieve complete contacting and achieve resin swelling, then the first portion is pumped through the resin bed plug flow style while simultaneously charging the second portion of the reagents to the top of the reactor so that remaining reagents pump through plug flow. This embodiment was demonstrated in examples 1,2,3,4,7,8,9,10.

Embodiment 21. The method of Embodiment 19, wherein final segment of deblocking reagent solution is reused from one phosphoramidite cycle to the next, which reduces acid volumes needed for the deblocking reaction, swells the resin and re-sets the bed with no channels at the beginning of deblocking, and washes away the ACN prior to plug flow reaction with virgin deblocking reagent solution. This embodiment was demonstrated in examples 7, 9, and 10.

Embodiment 22. The method of Embodiment 19, wherein each wash is split up into a series of multiple smaller wash portions that completely drain, which can minimize back mixing compared to one large continuous wash. This embodiment was demonstrated in examples 1, 2, 3, 4, 6, 7, 8, 9, 10.

Embodiment 23. The method of Embodiment 19, wherein some or all of the solvent washes are not fluidized, the wash begins with a fluidized portion followed by a plug flow portion, or the wash has a fluidized portion somewhere in the middle or end of plug flow washing, custom designed for efficiency of reagent removal and depending on when fluidization is needed to overcome pressure drop. This embodiment was demonstrated in examples 1, 2, 3, 4, 6, 7, 8, 9, 10.

Embodiment 24. The method of Embodiment 19, wherein the incoming reagents and wash solvents are distributed evenly radially on top of the resin bed with a spray cone or other distributor, to keep the resin bed flat and enable efficient plug flow reactions and washes. This embodiment was demonstrated in examples 8, 9, 10.

Embodiment 25. The method of Embodiment 19, wherein the cleaner fraction of the wash solvent is recycled and reused from one phosphoramidite cycle to the next. This embodiment was demonstrated in examples 6, 8, 9, 10.

Embodiment 26. The method of Embodiment 19, wherein in-process integrated multi-pass washing is used after reactions, as described herein. Solvent portions are passed through the reactor multiple times. For example, the sixth solvent wash portion after deblocking on cycle 1 becomes the fifth wash portion after deblocking on cycle 2, then it becomes the fourth wash portion after deblocking on cycle 3, and so on. In-process integrated multi-pass washing allows a much more efficient use of the wash solvent because only the "dirtiest" segments of wash solvent exit the system to waste after each reaction, and the virgin solvent feed is only required for the final wash segments. This embodiment was demonstrated in example 9, 10.

Embodiment 27. The method of Embodiment 19, wherein the reactor has a smaller diameter lower section that expands into a larger diameter upper section to facilitate fluidization when the reagents or wash solvents initially enter the reactor. The upflow inert gas pushes some or all of the resin beads up into the larger diameter section where the liquid and solid are able to interact with less wall effects. This embodiment was demonstrated in examples 2, 4, 6, 7.

Embodiment 28. The method of Embodiment 19, wherein the resin bed is fluidized/mixed with reagent liquid during deblocking, coupling, oxidation, sulfurization, and capping reaction steps in each cycle to achieve complete contacting and also to mitigate the otherwise high pressure drop when flowing down through the resin bed during reaction. This embodiment was demonstrated in examples 1, 2, 3, 4, 6, 7, 8, 9, 10.

Embodiment 29. The method of Embodiment 19, wherein initial portions of the solvent wash are fluidized to mitigate the otherwise high pressure drop when flowing down through the resin bed during the wash. This embodiment was demonstrated in examples 2, 3, 4.

Embodiment 30. The method of Embodiment 19, wherein the resin swelling is allowed to happen primarily during fluidization, which mitigates pressure drop when liquid subsequently flows down through the bed and out the bottom of the reactor. This embodiment was demonstrated in examples 1, 2, 3, 4, 6, 7, 8, 9, 10.

Embodiment 31. The method of Embodiment 19, wherein capping is omitted from some of the cycles. This embodiment was demonstrated in examples 9, 10.

Embodiment 32. The method of Embodiment 19, wherein some of the reactions are not fluidized at any point in the reaction, only plug flow contacting, for example deblocking with no fluidization when the virgin DCA solution is charged. This embodiment was demonstrated in examples 7, 9, 10.

Embodiment 33. The method of Embodiment 19, wherein inert gas pushes liquid down through the resin bed and a pump or other metering device at the outlet of the reactor controls the flow rate of liquid through the bed. This embodiment was demonstrated in examples 1, 2, 3, 4, 6, 7, 8, 9, 10.

Embodiment 34. The method of Embodiment 19, wherein amidite and activator solutions are charged into a separate zone, optionally mixed with inert gas bubbling in the zone, then pushed into the reactor. This embodiment was demonstrated in examples 1, 2, 4, 6, 7.

Embodiment 35. The method of Embodiment 19, wherein amidite and activator solutions are charged into a separate zone, optionally mixed with inert gas bubbling in the zone, and then pushed into a feed zone before pushing into the reactor. This embodiment was demonstrated in examples 3, 8, 9, 10.

Embodiment 36. The method of Embodiment 19, wherein reagents are charged to individual feed zones before pushing into the reactor. This embodiment was demonstrated in examples 1, 2, 4, 7.

Embodiment 37. The method of Embodiment 19, wherein reagents are charged to a common feed zone before pushing into the reactor. This embodiment was demonstrated in examples 3, 8, 9, 10.

Embodiment 38. The method of Embodiment 19, wherein reagents are pushed directly into the reactor rather than a feed zone. This embodiment was demonstrated in example 6.

Embodiment 39. The method of Embodiment 19, wherein wash solvent after coupling is reused in the wash solvent after oxidation/thiolation. This embodiment was demonstrated in example 10.

There are a variety of embodiments that may be make in which a product (including a oligonucleotide) is made via any of the methods and/or processes and/or embodiments outlined herein. For example, a product could be made using the following method:

A method of adding an oligonucleotide to a solid phase resin within a bed reactor, the method comprising:

- removing a protecting group from the 5' position of an oligonucleotide that is attached to the solid phase resin;
- adding an activated amidite solution to the bed reactor, wherein the activated amidite solution comprises an amidite and flows up and down within the bed reactor or fluidizes with nitrogen bubbling or other agitation and reacts at the 5' position of the oligonucleotide, wherein the phosphorous linkage found within the amidite comprises a P atom that is in an oxidation state of III; and
- converting the P atom from an oxidation state of III to an oxidation state of V.

The product made the above-recited method may be made with a process that further comprises the step of adding a capping solution before or after converting the P atom from an oxidation state of III to an oxidation state of V, wherein if the coupling moiety did not react with the amidite solution, the capping solution caps the coupling moiety such that no additional amidite can be coupled to the coupling moiety, wherein the capping solution flows up and down within the bed reactor or fluidizes with the resin beads using inert gas bubbling or other agitation, or flows down through the resin bed without fluidizing/mixing, or a fluidized portion of the reaction followed by a plug flow portion.

The product made the above-recited method may be made with a process that further comprises the step of removing the activated amidite solution from the from the bed reactor by passing the amidite solution through a filter located at the bottom of the bed reactor.

The product made the above-recited method may be made with a process that further comprises the step of adding a first washing solution to the bed reactor, wherein the adding of the first washing solution occurs after removing the protecting group.

The product made the above-recited method may be made with a process that further comprises the step of adding a second washing solution to the bed reactor, wherein the adding of the second washing solution occurs after the activated amidite solution has been added to the bed reactor.

The product made the above-recited method may be made with a process wherein the first and second washing solutions flow up and down within the bed reactor and wherein the method further comprises the step of individually removing the first and second washing solutions from the bed reactor by passing the first and second washing solutions through a filter located at the bottom of the bed reactor.

The product made the above-recited method may be made with a process wherein the adding of the second washing solution occurs before the step of converting the P atom from an oxidation state of III to an oxidation state of V.

The product made the above-recited method may be made with a process that further comprises the step of adding a third washing solution to the bed reactor, wherein the adding of the third washing solution occurs after converting the P atom from an oxidation state of III to an oxidation state of V.

The product made the above-recited method may be made with a process wherein the third washing solution flows up and down within the bed reactor and wherein the method further comprises the step of removing the third washing solution from the bed reactor by passing the third washing solution through a filter located at the bottom of the bed reactor.

The product made the above-recited method may be made with a process wherein the protecting group is a DMT group and wherein the removing the protecting group comprises reacting the 5' position of an oligonucleotide with an activating solution comprising an acid in solvent.

The product made the above-recited method may be made with a process that further comprises the step of removing the activating solution from the bed reactor by passing the activating solution through a filter located at the bottom of the bed reactor.

The product made the above-recited method may be made with a process wherein the upward and downward flow within the bed reactor is accomplished by adding pressure to the top of the reactor for the downward push and then releasing pressure from the top of the reactor for the upward push.

The product made the above-recited method may be made with a process wherein the solid and liquid fluidized bed mixing within the bed reactor is accomplished by adding nitrogen or another gas to the bottom of the reactor or some other type of agitation.

The product made the above-recited method may be made with a process wherein the first and second washing solutions mix within the bed reactor and wherein the method further comprises the step of individually removing the first and second washing solutions from the bed reactor by passing the first and second washing solutions through a filter located at the bottom of the bed reactor.

The product made the above-recited method may be made with a process wherein the wash solvent is drained out the bottom of the filter reactor prior to charging the next reagent; the reagent is drained out the bottom of the filter reactor prior to charging the next wash solvent; the resin bed is mixed to suspend the resin particles in the reagents and/or wash solvents by inert gas bubbling or up and down flow of the liquid at selected times during selected reactions and/or washes in each cycle.

The product made the above-recited method may be made with a process wherein a first portion of the reagents are charged into the reactor, the first portion is fluidized at the start of the reaction for a target amount of time to achieve complete contacting and achieve resin swelling, then the first portion is pumped through the resin bed plug flow style while simultaneously charging the second portion of the reagents to the top of the reactor so that remaining reagents pump through plug flow.

The product made the above-recited method may be made with a process wherein final segment of deblocking reagent solution is reused from one phosphoramidite cycle to the next, which reduces acid volumes needed for the deblocking reaction, swells the resin and re-sets the bed with no channels at the beginning of deblocking, and washes away the ACN prior to plug flow reaction with virgin deblocking reagent solution.

The product made the above-recited method may be made with a process wherein each wash is split up into a series of multiple smaller wash portions that completely drain, which can minimize back mixing compared to one large continuous wash.

The product made the above-recited method may be made with a process wherein some or all of the solvent washes are not fluidized, the wash begins with a fluidized portion followed by a plug flow portion, or the wash has a fluidized portion somewhere in the middle or end of plug flow washing, custom designed for efficiency of reagent removal and depending on when fluidization is needed to overcome pressure drop.

The product made the above-recited method may be made with a process wherein the incoming reagents and wash solvents are distributed evenly radially on top of the resin bed with a spray cone or other distributor, to keep the resin bed flat and enable efficient plug flow reactions and washes.

The product made the above-recited method may be made with a process wherein the cleaner fraction of the wash solvent is recycled and reused from one phosphoramidite cycle to the next.

The product made the above-recited method may be made with a process wherein in-process integrated multi-pass washing is used after reactions, as described herein. Solvent portions are passed through the reactor multiple times. For example, the sixth solvent wash portion after deblocking on cycle 1 becomes the fifth wash portion after deblocking on cycle 2, then it becomes the fourth wash portion after deblocking on cycle 3, and so on. In-process integrated multi-pass washing allows a much more efficient use of the wash solvent because only the "dirtiest" segments of wash solvent exit the system to waste after each reaction, and the virgin solvent feed is only required for the final wash segments.

The product made the above-recited method may be made with a process wherein the reactor has a smaller diameter lower section that expands into a larger diameter upper section to facilitate fluidization when the reagents or wash solvents initially enter the reactor. The upflow inert gas pushes some or all of the resin beads up into the larger diameter section where the liquid and solid are able to interact with less wall effects.

The product made the above-recited method may be made with a process wherein the resin bed is fluidized/mixed with reagent liquid during deblocking, coupling, oxidation, sulfurization, and capping reaction steps in each cycle to achieve complete contacting and also to mitigate the otherwise high pressure drop when flowing down through the resin bed during reaction.

The product made the above-recited method may be made with a process wherein initial portions of the solvent wash are fluidized to mitigate the otherwise high pressure drop when flowing down through the resin bed during the wash.

The product made the above-recited method may be made with a process wherein the resin swelling is allowed to happen primarily during fluidization, which mitigates pressure drop when liquid subsequently flows down through the bed and out the bottom of the reactor.

The product made the above-recited method may be made with a process wherein capping is omitted from some of the cycles.

The product made the above-recited method may be made with a process wherein some of the reactions are not fluidized at any point in the reaction, only plug flow contacting, for example deblocking with no fluidization when the virgin DCA solution is charged.

The product made the above-recited method may be made with a process wherein inert gas pushes liquid down through the resin bed and a pump or other metering device at the outlet of the reactor controls the flow rate of liquid through the bed.

The product made the above-recited method may be made with a process wherein amidite and activator solutions are charged into a separate zone, optionally mixed with inert gas bubbling in the zone, then pushed into the reactor.

The product made the above-recited method may be made with a process wherein amidite and activator solutions are charged into a separate zone, optionally mixed with inert gas bubbling in the zone, and then pushed into a feed zone before pushing into the reactor.

The product made the above-recited method may be made with a process wherein reagents are charged to individual feed zones before pushing into the reactor.

The product made the above-recited method may be made with a process wherein reagents are charged to a common feed zone before pushing into the reactor.

The product made the above-recited method may be made with a process wherein reagents are pushed directly into the reactor rather than a feed zone.

The product made the above-recited method may be made with a process wherein wash solvent after coupling is reused in the wash solvent after oxidation/thiolation.

Or other products may be made using other methods as well.

The invention claimed is:

1. A method of assembling an oligonucleotide that is attached to a solid support within a bed reactor, the method comprising:

removing a protecting group from the 5' position of an oligonucleotide that is attached to the solid support;

adding an activated amidite solution to the bed reactor, wherein the activated amidite solution comprises an amidite and flows up and down within the bed reactor or fluidizes with nitrogen bubbling or other agitation and reacts at the 5' position of the oligonucleotide, wherein the phosphorous linkage found within the amidite comprises a P atom that is in an oxidation state of III; and converting the P atom from an oxidation state of III to an oxidation state of V, the upward and downward flow within the bed reactor is accomplished by adding pressure to the top of the reactor during the downward push and then releasing pressure from the top of the reactor during the upward push.

2. The method of claim 1, further comprising the step of adding a capping solution before or after converting the P atom from an oxidation state of III to an oxidation state of V, wherein if the coupling moiety did not react with the amidite solution, the capping solution caps the coupling moiety such that no additional amidite can be coupled to the coupling moiety, wherein the capping solution flows up and down within the bed reactor or fluidizes with nitrogen bubbling or other agitation, or flows down through the resin bed without fluidizing/mixing, or a fluidized portion of the reaction followed by a plug flow portion.

3. The method of claim 1, further comprising the step of removing the activated amidite solution from the bed reactor by passing the amidite solution through a filter located at the bottom of the bed reactor.

4. The method of claim 1, further comprising the step of adding a first washing solution to the bed reactor, wherein the adding of the first washing solution occurs after removing the protecting group.

5. The method of claim 4, further comprising the step of adding a second washing solution to the bed reactor, wherein the adding of the second washing solution occurs.

6. The method of claim 5, wherein the first and second washing solutions flow up and down within the bed reactor and wherein the method further comprises the step of individually removing the first and second washing solutions from the bed reactor by passing the first and second washing solutions through a filter located at the bottom of the bed reactor.

7. The method of claim 5, wherein the adding of the second washing solution occurs before the step of converting the P atom from an oxidation state of III to an oxidation state of V.

8. The method of claim 5, further comprising the step of adding a third washing solution to the bed reactor, wherein the adding of the third washing solution occurs after converting the P atom from an oxidation state of III to an oxidation state of V.

9. The method of claim 8, wherein the third washing solution flows up and down within the bed reactor and wherein the method further comprises the step of removing the third washing solution from the bed reactor by passing the third washing solution through a filter located at the bottom of the bed reactor.

10. The method of claim 5, wherein the first and second washing solutions mix within the bed reactor and wherein the method further comprises the step of individually removing the first and second washing solutions from the bed reactor by passing the first and second washing solutions through a filter located at the bottom of the bed reactor.

11. The method of claim 5, wherein:

the wash solvent is drained out the bottom of the filter reactor prior to charging the next reagent; or the reagent is drained out the bottom of the filter reactor prior to charging the next wash solvent; or a resin bed of the bed reactor is mixed to suspend resin particles in the reagents and/or wash solvents by inert gas bubbling or up and down flow of the liquid at selected times during selected reactions and/or washes in each cycle.

12. The method of claim 11, wherein a first portion of the reagents are charged into the reactor, the first portion is fluidized at the start of the reaction for a target amount of time to achieve complete contacting and achieve resin swelling, then the first portion is pumped through the resin bed plug flow style while simultaneously charging the second portion of the reagents to the top of the reactor so that remaining reagents pump through plug flow.

13. The method of claim 11, wherein a final segment of deblocking reagent solution is reused from one phosphoramidite cycle to the next, which reduces acid volumes needed for the deblocking reaction, swells the resin and re-sets the bed with no channels at the beginning of deblocking, and washes away ACN prior to plug flow reaction with virgin deblocking reagent solution.

14. The method of claim 11, wherein each wash is split up into a series of multiple smaller wash portions that completely drain, which can minimize back mixing compared to one large continuous wash.

15. The method of claim 11, wherein one or more of the solvent washes are not fluidized, the wash begins with a fluidized portion followed by a plug flow portion, or the wash has a fluidized portion somewhere in the middle or end of plug flow washing, custom designed for efficiency of reagent removal and depending on when fluidization is needed to overcome pressure drop.

16. The method of claim 11, wherein the incoming reagents and wash solvents are distributed evenly radially on top of the resin bed with a spray cone or other distributor, to keep the resin bed flat and enable efficient plug flow reactions and washes.

17. The method of claim 11, wherein one or more fractions of the wash solvent is recycled and reused from one phosphoramidite cycle to the next.

18. The method of claim 11, wherein in-process integrated multi-pass washing is used one or more times.

19. The method of claim 11, wherein the reactor has a smaller diameter lower section that expands into a larger diameter upper section to facilitate fluidization when the reagents or wash solvents initially enter the reactor.

20. The method of claim 11, wherein the resin bed is fluidized/mixed with reagent liquid during the other reaction steps in each cycle to achieve complete contacting and also to mitigate the otherwise high pressure drop when flowing down through the resin bed during reaction.

21. The method of claim 11, wherein initial portions of the solvent wash are fluidized to mitigate the otherwise high pressure drop when flowing down through the resin bed during the wash.

22. The method of claim 11, wherein capping is omitted from one or more of the cycles.

23. The method of claim 11, wherein one or more of the reactions are not fluidized at any point in the reaction.

24. The method of claim 11, wherein inert gas pushes liquid down through the resin bed and a pump or other metering device at the outlet of the reactor controls the flow rate of liquid through the bed.

25. The method of claim 11, wherein amidite and activator solutions are charged into a separate zone, optionally mixed with inert gas bubbling in the zone, then pushed into the reactor.

26. The method of claim 11, wherein amidite and activator solutions are charged into a separate zone, mixed with inert gas bubbling in the zone, and then pushed into a feed zone before pushing into the reactor.

27. The method of claim 11, wherein reagents are charged to individual feed zones before pushing into the reactor.

28. The method of claim 11, wherein reagents are charged to a common feed zone before pushing into the reactor.

29. The method of claim 11, wherein reagents are pushed directly into the reactor rather than a feed zone.

30. The method of claim 11, wherein wash solvent after coupling is reused in the wash solvent after oxidation/thiolation.

31. The method of claim 1, wherein the protecting group is a DMT group and wherein the removing the protecting group comprises reacting the 5' position of an oligonucleotide with an activating solution comprising an acid in solvent.

32. The method of claim 31, wherein the method further comprises the step of removing the activating solution bed reactor by passing the activating solution through a filter located at the bottom of the bed reactor.

* * * * *